(12) United States Patent
Tee

(10) Patent No.: US 12,428,681 B2
(45) Date of Patent: Sep. 30, 2025

(54) MARKERS OF TOTIPOTENCY AND METHODS OF USE

(71) Applicant: AGENCY FOR SCIENCE, TECHNOLOGY AND RESEARCH, Singapore (SG)

(72) Inventor: Wee Wei Tee, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 1165 days.

(21) Appl. No.: 16/616,523

(22) PCT Filed: May 30, 2018

(86) PCT No.: PCT/SG2018/050268
§ 371 (c)(1),
(2) Date: Nov. 25, 2019

(87) PCT Pub. No.: WO2018/222139
PCT Pub. Date: Dec. 6, 2018

(65) Prior Publication Data
US 2021/0139982 A1  May 13, 2021

(30) Foreign Application Priority Data
May 29, 2017  (SG) .......................... 10201704380R

(51) Int. Cl.
| G01N 31/00 | (2006.01) |
| C12N 5/0735 | (2010.01) |
| C12Q 1/6881 | (2018.01) |
| G01N 33/53 | (2006.01) |
| G01N 33/68 | (2006.01) |

(52) U.S. Cl.
CPC ......... C12Q 1/6881 (2013.01); C12N 5/0606 (2013.01); G01N 33/68 (2013.01); C12Q 2600/158 (2013.01); G01N 2333/4704 (2013.01)

(58) Field of Classification Search
None
See application file for complete search history.

(56) References Cited

U.S. PATENT DOCUMENTS

2016/0299141 A1  10/2016  Kraus et al.

FOREIGN PATENT DOCUMENTS

| WO | WO-2012129342 A1 * | 9/2012 | ............. C07K 14/47 |
| WO | WO-2013/181641 A1 | 12/2013 | |
| WO | WO-2014/096800 A1 | 6/2014 | |

OTHER PUBLICATIONS

Ko, Minoru (NIH, Expression profiling of mouse embryonic and tissue stem cells, Fiscal year 2011, Project #1ZIAAG000662-11, Application #8335887). (Year: 2011).*
Neidhardt et al. (Mechanisms of Development, 98 (2000) pp. 77-930) (Year: 2000).*
Hendrickson et al. (Nat Genet. Jun. 2017; 49(6); 925-934) published online May 1, 2017. (Year: 2017).*
Carter et al. (Gene Expr. Patterns, Nov. 4, 2007, vol. 8, No. 3, pp. 181-198) (Year: 2007).*
Akiyama et al., "Transient Bursts of Zscan4 Expression are Accompanied by the Rapid Derepression of Heterochromatin in Mouse Embryonic Stem Cells", DNA Research, 22(5), 2015, pp. 307-318.
Hendrickson et al., "Conserved Roles for Murine DUX and Human DUX4 in Activating Cleavage Stage Genes and MERVL/HERVL Retrotransposons", Nat Genet., 49(6), Jun. 2017, 30 pages.
Lu et al., "Cell Totipotency: Molecular Features, Induction, and Maintenance", Natl Sci Rev, vol. 2, No. 2, Jun. 1, 2015, pp. 217-225.
Biswas et al., "Chemically Induced Reprogramming of Somatic Cells to Pluripotent Stem Cells and Neural Cells", International Journal of Molecular Sciences, vol. 17, No. 2, Feb. 6, 2016, 13 pages.
Narita et al., "NELF Interacts With CBC and Participates in 3' End Processing of Replication-dependent Histone mRNAs", Mol Cell, vol. 26, No. 3, May 11, 2007, pp. 349-365.
Luo et al., "A Conserved Protein Motif is Required for Full Modulatory Activity of Negative Elongation Factor Subunits NELF-A and NELF-B in Modifying Glucocorticoid Receptor-regulated Gene Induction Properties", J. Biol Chem, vol. 288, No. 47, Oct. 6, 2013, pp. 34055-34072.

(Continued)

*Primary Examiner* — Lisa V Cook
(74) *Attorney, Agent, or Firm* — MARSHALL, GERSTEIN & BORUN LLP

(57) ABSTRACT

The present invention relates to methods of determining a potency state of an embryonic stem cell (ESC) in culture, comprising detecting the expression level of Negative Elongation Factor Complex Member A (Nelfa) in the ESC, and correlating the expression level of Nelfa with that of a reference sample to determine the potency state of the ESC. The present invention also provides methods of selecting totipotent-like ESCs from a population of ESCs in culture using an anti-Nelfa antigen binding protein, methods of inducing totipotency in an ESC in culture, methods of improving the reprogramming efficiency of a somatic cell into an induced pluripotent stem cell and methods of reprogramming a somatic cell into a totipotent stem cell by inducing Nelfa expression. Cells comprising an expression vector encoding Nelfa and kits for use in the methods of the invention are also provided.

20 Claims, 40 Drawing Sheets
Specification includes a Sequence Listing.

(56) References Cited

OTHER PUBLICATIONS

Carter et al., "An In Situ Hybridization-based Screen for Heterogeneously Expressed Genes in Mouse ES Cells", Gene Expr Patterns, vol. 8, No. 3, Nov. 4, 2007, 24 pages.
Yamaguchi et al., "NELF, a Multisubunit Complex Containing RD, Cooperates With DSIF to Repress RNA Polymerase II Elongation", Cell, vol. 97, No. 1, Apr. 2, 1999, pp. 41-51.
Wang et al., "NELF Potentiates Gene Transcription in the *Drosophila* Embryo", PLoS One, vol. 9, No. 7, Jul. 9, 2010, 8 pages.
Search Report and Written Opinion in International Application No. PCT/SG2018/050268 dated Aug. 17, 2018, 11 pages.
https://www.r-project.org.
https://cran.r-project.org/web/packages/amap/index.html.
https://www.bioinformatics.babraham.ac.uk/projects/trim_galore.
Luo et al., "A Conserved Protein Motif is Required for Full Modulatory Activity of Negative Elongation Factor Subunits NELF-A and NELF-B in Modifying Glucocorticoid Receptor-regulated Gene Induction Properties", The Journal of Biological Chemistry, vol. 288, No. 47, Nov. 22, 2013, pp. 34055-34072.
Yamaguchi et al., "NELF, A Multisubunit Complex Containing RD, Cooperates with DSIF to Repress RNA Polymerase II Elongation", Cell, vol. 97, Apr. 2, 1999, pp. 41-51.
Wang et al., "NELF Potentiates Gene Transcription in the *Drosophila* Embryo", PLoS One, vol. 5, Issue 7, Jul. 2010, 8 pages.
Narita et al., "NELF Interacts with CBC and Participates in 3' End Processing of Replication-Dependent Histone mRNAs", Molecular Cell, vol. 26, May 11, 2007, pp. 349-365.
Lu et al., "Cell Totipotency: Molecular Features, Induction and Maintenance", Natl Sci Rev, vol. 2, No. 2, Jun. 2015, 15 pages.
Biswas et al., "Chemically Induced Reprogramming of Somatic Cells to Pluripotent Stem Cells and Neural Cells", Int. J. Mol. Sci., vol. 17, 2016, 13 pages.
Carter et al., "An in situ hybridization-based Screen for Heterogeneously Expressed Genes in Mouse ES Cells", Gene Expr Patterns, vol. 8, No. 3, Feb. 2008, 24 pages.
Invitation to Respond to Written Opinion and Written Opinion in SG Application No. 11201909866V dated Aug. 3, 2020, 9 pages.
Extended European Search Report in EP Application No. 18809234.0 dated Mar. 11, 2021, 7 pages.
Hu, et al. "Maternal factor NELFA drives a 2C-like state in mouse embryonic stem cells", Nature Cell Biology, Macmillan Magazines LTD, vol. 22, No. 2, Jan. 13, 2020, pp. 175-186.
Second Written Opinion in SG Application No. 11201909866V dated Mar. 8, 2022, 7 pages.
Communication Pursuant to Article 94(3) EPC dated Sep. 3, 2024, 5 pages.

* cited by examiner

*Nelfa, Sh3kbp1, Trim75, Abhd3, Strip2, Gm839, Slc25a31 and Galnt3*

Known motif: GATA3

| Dataset | p-value |
|---|---|
| NELFA[high] | p=1e-04 |
| NELFA (+Dox) | p=1e-05 |
| DUX-ChIP-seq | p=1e-3140 |

De novo motif: DUX

| Dataset | p-value |
|---|---|
| NELFA[high] | p=1e-20 |
| NELFA (+Dox) | p=1e-23 |
| DUX-ChIP-seq | p=1e-8233 |

Figure 3e

MARKERS OF TOTIPOTENCY AND METHODS OF USE

A Sequence Listing, which is a part of the present disclosure, is submitted concurrently with the specification as a text file. The name of the text file containing the Sequence Listing is "54853_Seqlisting.txt." The Sequence Listing was created on Nov. 20, 2019, and is 5,140 bytes in size. The subject matter of the Sequence Listing is incorporated herein in its entirety by reference.

CROSS-REFERENCE TO RELATED APPLICATIONS

This application claims the benefit of priority of Singapore application No. 10201704380R, filed 29 May 2017, the contents of it being hereby incorporated by reference in its entirety for all purposes.

FIELD OF THE INVENTION

The invention is in the field of stem cells, in particular markers of potency of stem cells and methods of identifying and inducing totipotency in stem cells.

BACKGROUND OF THE INVENTION

Early mammalian development is a highly complex process involving elaborate changes in gene expression that is also accompanied by extensive chromatin remodelling. The discovery and derivation of pluripotent stem cells have captivated the interest of scientists and public alike, and the potential utility of stem cells for regenerative medicine has fueled intense research, culminating in the landmark discovery showing that somatic cells can be reverted into induced pluripotent stem cells (iPSCs). The latter demonstrates that cellular plasticity is encoded in most, if not all, differentiated cells, but the relatively low efficiency of most in vitro reprogramming strategies points to an inadequate understanding of the process and enablers. Unlike pluripotent stem cells that can only contribute to the embryonic lineages, totipotent cells can generate the entire organism, including both embryonic and extraembryonic lineages. Totipotent cells thus exhibit maximal cellular plasticity, surpassing that of pluripotent cells. This catapults totipotent cells to be at the pinnacle of developmental hierarchy, holding tremendous potential for regenerative medicine.

The totipotent property is thought to be exclusive to the early cleavage-stage embryos in vivo (eg. 2-cell embryo in mouse). As the totipotent zygote develops into an embryo with distinct cell lineages, genetic and epigenetic mechanisms must operate in sync to direct appropriate changes in cell fates. Numerous studies have identified master transcription factors such as Oct4, Nanog and Gata4 important for lineage specification in the blastocyst. In comparison, relatively less is known about the players and mechanisms that operate in the totipotent zygote and developing morula.

As such, there is a need to identify a marker of totipotency that allows a maximum degree of cellular plasticity to be achieved and maintained, thereby providing more options for efficient reprogramming and potential therapeutic avenues.

SUMMARY

In one aspect, there is provided a method of determining a potency state of an embryonic stem cell (ESC) in culture comprising:
  a) detecting the expression level of Nelfa in said embryonic stem cell;
  b) correlating the expression level of Nelfa in said embryonic stem cell with that of a reference sample to determine the potency state of said embryonic stem cell.

In one aspect, there is provided a method of selecting totipotent-like embryonic stem cells (ESCs) from a population of embryonic stem cells in culture, comprising:
  a) contacting said population of ESCs with an anti-Nelfa antigen binding protein;
  b) identifying the ESCs binding to said anti-Nelfa antigen binding protein; and
  c) optionally isolating the ESCs from said anti-Nelfa antigen binding protein In one aspect, there is provided a method of inducing totipotency in an embryonic stem cell (ESC) in culture, comprising contacting and incubating said ESC with one or more of a metabolic regulator, a small molecule compound, a chemical, a virus, a nucleic acid or a polypeptide, to induce expression of Nelfa.

In one aspect, there is provided a use of a metabolic regulator, a nucleic acid, a small molecule, a chemical, a virus or a polypeptide for inducing totipotency in an embryonic stem cell.

In one aspect, there is provided a cell comprising an expression vector encoding Nelfa operably linked to a promoter.

In one aspect, there is provided a kit comprising at least one of a metabolic regulator, a nucleic acid, a polypeptide, a small molecule, a virus or a chemical when used in the method as described herein.

In one aspect, there is provided a method of improving the reprogramming efficiency of a somatic cell into an induced pluripotent stem cell (iPSC), comprising contacting and incubating said somatic cell with one or more of a metabolic regulator, a small molecule compound, a chemical, a nucleic acid, a virus or a polypeptide to induce expression of Nelfa.

In one aspect, there is provided a method of reprogramming a somatic cell into a totipotent stem cell comprising contacting and incubating said somatic cell with one or more of a metabolic regulator, a small molecule compound, a chemical, a nucleic acid, a virus or a polypeptide to induce expression of Nelfa.

Definitions

The following words and terms used herein shall have the meaning indicated:

The term "stem cell" refers to a cell that has the ability to both self-renew and differentiate into other cell types.

As used herein, the term "potency" refers to the sum of all developmental options accessible to the cell (i.e., the developmental potency) and the term "potency state" of a stem cell refers to the ability of the stem cell to differentiate into various cell types. A stem cell that can differentiate into more cell types has a greater potency than a stem cell that can differentiate into fewer cell types.

The potency state of a cell can be determined by assessing characteristics of potency which include but are not limited to cell morphology, expression of markers of specific potency states or markers of specific lineages, ability of mouse stem cells to contribute to germline transmission in mouse chimeras, ability of stem cells to contribute to the embryo proper using tetraploid embryo complementation assays, teratoma formation of stem cells, formation of embryoid bodies and inactive X chromosome reactivation.

It will be understood to a person skilled in the art that cellular or developmental potency exists as a continuum, ranging from a cell with the highest development potency, a totipotent cell, to a cell with the least developmental potency, a terminally differentiated cell. Cells in this continuum can be broadly classified as being totipotent, pluripotent, multipotent, oligopotent, unipotent or terminally differentiated. As cellular or developmental potency exists as a continuum, it will be understood to a person skilled in the art that characteristics of potency would also be observed as a continuum.

A "totipotent cell", "totipotent stem cell" or "totipotent-like cell" is a cell that has the developmental potential to make all of the cells in the adult body as well as the extra-embryonic tissues, including the placenta. The fertilized egg (zygote) is totipotent, as are the cells (blastomeres) of the morula (up to the 16-cell stage following fertilization).

A "pluripotent cell", "pluripotent stem cell" or "pluripotent-like cell" refers to a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). The developmental competency of a cell to differentiate to all three germ layers can be determined using, for example, a nude mouse teratoma formation assay.

An "induced pluripotent cell", "induced pluripotent stem cell" (iPSC) or "induced pluripotent-like cell" refers to a stem cell that is produced from differentiated adult cells or somatic cells that have been induced or changed, i.e., reprogrammed into cells capable of differentiating into tissues of all three germ or dermal layers: mesoderm, endoderm, and ectoderm. The iPSCs produced do not refer to cells as they are found in nature.

An "embryonic stem cell" (ESC) or "embryonic stem cell-like cell" refers to naturally occurring pluripotent stem cells of the inner cell mass of the embryonic blastocyst. Such cells can similarly be obtained from the inner cell mass of blastocysts derived from somatic cell nuclear transfer. Embryonic stem cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta, i.e., are not totipotent, although rarely ESCs may exhibit certain characteristics of totipotent cells, for example expression of one or more totipotent markers.

As used herein, the term "differentiation" refers to the process by which a cell with a higher development potential or a higher potency acquires the features of a cell that has a lower development potential or a lower potency. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell.

As used herein, the term "undifferentiated cell" refers to a cell in an undifferentiated state that has the property of self-renewal and has the developmental potential to differentiate into multiple cell types, without a specific implied meaning regarding developmental potential (i.e., totipotent, pluripotent, multipotent, etc.).

As used herein, the term "expression level" in the context of a marker (e.g. Nelfa) refers to the gene or protein expression level of the marker in a sample. The expression level of a marker in the sample may be determined by comparison with a reference sample.

As used herein, the term "marker" refers to a molecule that provides an indication of a physiological state, based on its presence or absence or based on its relative levels in a cell or organism. An example of a marker includes but is not limited to a nucleic acid, a polypeptide, a major or microsatellite repeat, a retrotransposon, a metabolite or a chemical. A marker may also be a protein or a compound associated with a biochemical pathway, or with totipotency or pluripotency.

As used herein, the term "nucleic acid" means any single or double-stranded RNA or DNA molecule, such as mRNA, cDNA, genomic DNA, xeno DNA, siRNA or microRNA.

As used herein, the term "reprogramming" refers to a method of increasing the developmental potential or potency of a cell to a less differentiated state. In other words, a reprogrammed cell is one that is in a less differentiated state than the same cell in a non-reprogrammed state. The efficiency of reprogramming may be measured by methods that include but are not limited to the percentage of cells in a cell population that have been reprogrammed, the time required for reprogramming and the number of factors required to reprogram the cells.

The terms "antigen binding protein" and "antigen-binding fragment thereof" as used herein refers to antibodies, antibody fragments and other protein constructs, such as domains, polypeptides, and oligo-peptides which are capable of binding to an epitope of interest.

The term "antibody" is used herein in the broadest sense to refer to whole antibodies, antigen binding protein and any antigen-binding fragment (i.e., "antigen-binding portion") or single chains thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, the term "inducing" in the context of potency refers to a method of increasing the developmental potential or potency of a cell. "Inducing totipotency" therefore refers to increasing the developmental potential or potency of a cell so that the cell displays totipotent or totipotent-like characteristics.

As used herein, the term "metabolic regulator" refers to any molecule or compound that affects metabolic function. For example, a metabolic regulator may be a metabolite of one or more metabolic pathways that acts as a co-activator or substrate of one or more metabolic pathways. In another example, a metabolic regulator may also be a gene or a protein or an enzyme that regulates the activation or repression of a metabolic pathway. In yet another example, a metabolic regulator may affect oxidative phosphorylation and/or glycolysis. Therefore, the term "metabolic regulator" in the context of reprogramming or potency refers to any molecule or compound that is capable of affecting metabolic function to thereby increase the developmental potential or potency of a cell.

As used herein, the term "small molecule compound" in the context of reprogramming or potency refers to any small molecule that is capable of affecting a biochemical pathway, cellular architecture or chromatin structure in a cell to thereby increase the developmental potential or potency of a cell.

"Operably linked" or "operatively linked" refers to the relationship between two or more nucleotide sequences that interact physically or functionally. For example, a promoter or regulatory nucleotide sequence is said to be operably linked to a nucleotide sequence that codes for a RNA or a protein if the two sequences are situated such that the regulatory nucleotide sequence will affect the expression level of the coding or structural nucleotide sequence. A 5' portion of a gene is operatively or operably linked with a 3' portion of a gene if the two portions are situated to form a functional gene.

"Inducible promoter" refers to a promoter whose activity is under the control of an inducing agent. Contacting the promoter with the inducing agent activates the promoter which in turn, drives expression of a gene (e.g. reporter gene).

BRIEF DESCRIPTION OF THE DRAWINGS

The invention will be better understood with reference to the detailed description when considered in conjunction with the non-limiting examples and the accompanying drawings, in which:

FIG. 1 shows that the maternal factor NELFA is heterogeneously expressed in mouse embryonic stem cells (mESCs). FIG. 1 illustrates that NELFA is conspicuously absent (or lowly expressed) in the majority of mESCs, with the noteworthy exception of a small population of rare cells that exhibited high expression of NELFA (NELFA$^{high}$)

FIG. 2 shows that NELFA$^{high}$ mESCs mark a 2C-like state. FIG. 2f is a set of boxplots indicating the relative expressions of NELFA$^{high}$- upregulated (Up) and the non-upregulated genes (Non-Up) in 2C-like cells induced by CAF1 inhibition (left panel), over-expression of Dux (middle panel) and Zscan4-positive ESCs (right panel) respectively. NELFA$^{high}$-upregulated genes (n=1086) are specifically enriched in the various 2C-like mESC transcriptomes. Center line: median; box limits: lower and upper quartiles; upper whisker: the smaller value of the maximum value and upper quantile plus 1.5× the interquartile range; lower whisker: the larger value of the minimum value and the lower quantile minus 1.5× the interquartile range. Thus, FIG. 2 illustrates that NELFA$^{high}$ mESCs selectively activate 2C-specific genes that are normally repressed in the pluripotent state.

FIG. 3 shows that NELFA is a novel driver of the 2C-like state in mESCs. FIG. 3e shows sequences and tables depicting motif enrichment analysis of upregulated gene promoters in NELFA$^{high}$ and NELFA-induced 2C-like cells, along with DUX-bound peaks from a Dux ChIP-seq dataset, uncovered overrepresented GATA3 and DUX transcription factor binding motifs. FIG. 3 illustrates that NELFA's expression is not merely a reporter, but also a novel driver of the 2C-like state and that whilst NELFA may prime the expression of Dux, both factors once expressed, act in an auto-regulatory fashion to ensure robust induction of the 2C-gene expression program.

FIG. 4 shows that suppression of glycolysis induces the 2C-like transcriptional program in a NELFA-dependent manner. FIG. 4 illustrates that suppression of glycolysis can promote the emergence of 2C-like mESCs and that NELFA remains a critical player in this process and that there is a novel link between metabolism and the induction of 2C-like mESCs.

FIG. 5 shows that NELFA interacts with histone H1 to regulate chromatin accessibility.

Scale bars=20 µm. FIG. 5 illustrates a model in which NELFA's interaction with linker H1 histone leads to the latter's displacement from chromatin, and in doing so, induces chromatin decondensation that may contribute to the activation of 2C genes in NELFA-upregulated mESCs.

FIG. 6 shows that multiple pathways contribute to chromatin decondensation in NELFA-upregulated 2C-like mESCs. FIG. 6 illustrates that multiple pathways are involved to ensure robust chromatin decompaction in NELFA-upregulated mESCs, and that chromatin decompaction is an important preceding step for the downstream activation of 2C program. FIG. 6 also illustrates the conceptual parallels between epigenetic reprogramming events in the germline and 2C-like cells, highlighting common principles underlying cellular reprogramming in general.

FIG. 7 shows that candidate glycolytic regulators affect 2C-gene expression. FIG. 7 illustrates the importance of metabolic regulation in controlling the transition between pluripotent and 2C-like states, and further demonstrated a surprisingly facile method of inducing a 2C-like state without the need for any genetic manipulation.

DETAILED DESCRIPTION OF THE PRESENT INVENTION

Figure 1A:
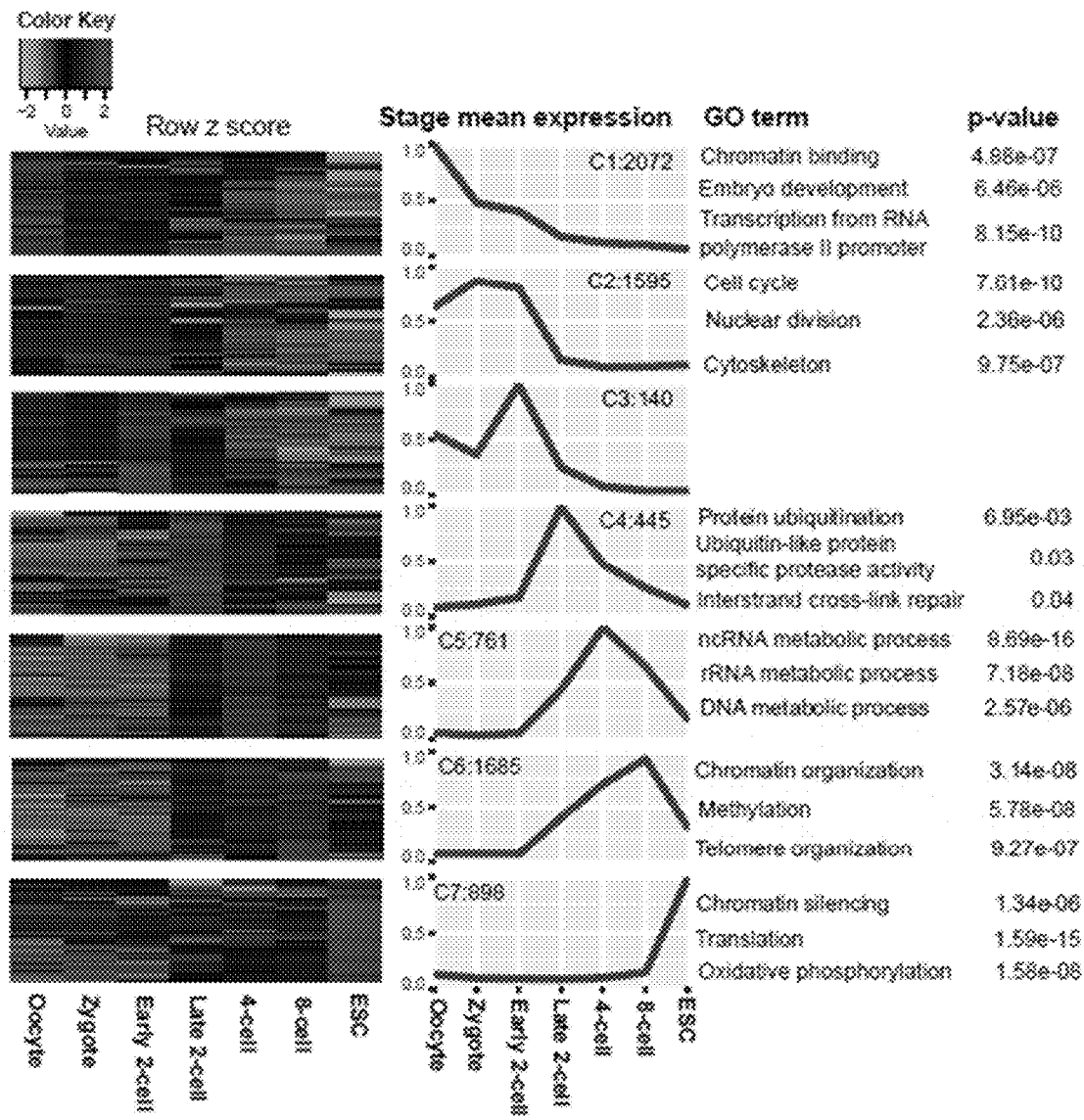
FIG. 1a is a heat map depicting clusters of genes showing distinct stage-specific expression patterns during mouse pre-implantation development, and including mESCs. Representative enriched GO terms and their corresponding p-values are shown on the right. GO: Gene Ontology.

In a first aspect the present invention refers to a method of determining a potency state of an embryonic stem cell (ESC) in culture comprising:
  a) detecting the expression level of Negative Elongation Factor Complex Member A (Nelfa) in said embryonic stem cell; and
  b) correlating the expression level of Nelfa in said embryonic stem cell with that of a reference sample to determine the potency state of said embryonic stem cell.

In some embodiments, the ESC is a mammalian ESC. Examples of mammalian ESCs include but are not limited to mouse and human stem cells. In a preferred embodiment, the ESC is a human ESC.

In some embodiments, the potency state of an embryonic stem cell determined using the method of the present invention is a totipotent-like state. It will generally be understood that a cell having a totipotent or totipotent-like state exhibits characteristics of totipotent cells. Characteristics of totipotent cells include but are not limited to expression of markers that are associated with totipotency, the ability to differentiate into cells of all embryonic and extra-embryonic tissue, changes in chromatin structure such as decondensed chromatin, loss of chromocenters, differential localization of histone chaperones such as NAP1 and CAF1, genome wide DNA demethylation and suppression of metabolic pathways such as oxidative phosphorylation and glycolysis pathways.

Examples of markers associated with totipotency include markers expressed at the oocyte stage, zygote, 2-cell stage and the 4-cell stage. Such markers may include but are not limited to the genes Zscan4, Tcstv3, Gm4340, Dux and the MERVL/HERVL family of retrotransposons. Examples of the MERVL/HERVL family of endogenous retrotransposons include but are not limited to mt2_mm, Mervl-b4-int, MERVL_gag and Mervl-int. Another example of a totipotent marker is the major satellite repeat gsat_mm. It will generally be understood that the totipotent-like state may be characterized by the expression of one or more totipotent markers.

In some embodiments, detection of an increased level of Nelfa expression relative to the reference sample indicates that said embryonic stem cell has a totipotent-like state. A reference sample may be a cell or population of cells with a known potency state, such as embryonic stem cells. In another example, a reference sample may be a cell or sample of cells at a known developmental stage, such as the pre-implantation stage. An example of reference samples include but are not limited to E11.5 primordial germ cells (PGCs), an oocyte, a zygote, and a 2C-stage embryo.

Detection of Nelfa expression level may be detection of Nelfa gene expression, Nelfa messenger RNA (mRNA expression), Nelfa protein expression or combinations thereof.

The level of Nelfa expression may be detected using assays routine in the art including but not limited to gene expression assays and protein assays. Gene expression assays include but are not limited to polymerase chain reaction (PCR), fluorescence in situ hybridization (FISH), Northern blotting, microarray and RNA-Seq. It will be understood that PCR includes real time PCR, quantitative and semi-quantitative PCR. The expression or upregulation of the expression of markers may also be determined by protein assays including but not limited to immunohistochemistry, immunofluorescence, Western blotting, flow cytometry and ELISA.

In one example, the step of detecting the protein expression level of Nelfa may be by immunohistochemistry or flow cytometry.

In another example, the gene expression level of Nelfa may be determined by contacting a nucleic acid sequence obtained or derived from said embryonic stem cell with at least one primer and/or at least one probe for amplification of the Nelfa sequence, amplifying said nucleic acid sequence using said at least one primer and/or said at least one probe, and detecting the gene expression level of Nelfa.

The amplification step may be performed by polymerase chain reaction (PCR). In one example, the PCR may be quantitative RT-PCR.

A cell that has a totipotent-like state may also be characterized by Nelfa induced expression of totipotent markers. In one embodiment, the totipotent-like state is characterized by Nelfa induced expression of Zscan4, Tcstv3, Gm4340, Dux, the MERVL family of retrotransposons, gsat_mm or combinations thereof. It will be appreciated that the MERVL/HERVL family of retrotransposons include but are not limited to MERVL, mt2_mm, MERVL_gag, Mervl-b4-int and Mervl-int.

The totipotent-like state may also be characterized in that Nelfa acts upstream of Zscan4 and the MERVL/HERVL family of retrotransposons in embryonic stem cells.

The totipotent-like state may further be characterized by differential localization of histone chaperone proteins. In one example, the totipotent-like state is characterized by transient nuclear import of nucleosome assembly protein 1 (NAP1). In another example, the totipotent-like state may be characterized by translocation of chromatin assembly factor 1 (CAF1) to the cytoplasm. In yet another embodiment, the totipotent-like state is characterized by chromatin decondensation and expression of the MERVL/HERVL family of retrotransposons and Zscan4 in the ESC.

The present invention also provides a method of selecting totipotent-like embryonic stem cells (ESCs) from a population of embryonic stem cells in culture, comprising providing a population of ESCs that displays a predetermined phenotype when Nelfa is expressed, identifying the ESCs that express the predetermined phenotype, and selecting the ESCs that express the predetermined phenotype.

In one embodiment, the predetermined phenotype is expression of a reporter gene. Suitable reporter genes would be well known to one of skilled in the art and may include fluorescent protein genes such as mCherry, green fluorescent protein (GFP) or enhanced GFP (EGFP), red fluorescent protein (RFP), yellow fluorescent protein (YFP), blue fluorescent protein (BFP), or cyan fluorescent protein (CFP).

An example of a population of ESCs that displays a preselected phenotype when Nelfa is expressed is a Nelfa-EGFP knock in cell line.

The present invention also provides a method of selecting totipotent-like embryonic stem cells (ESCs) from a population of embryonic stem cells in culture, comprising contacting said population of ESCs with an anti-Nelfa antigen binding protein identifying the ESCs binding to said anti-Nelfa antigen binding protein and optionally isolating the ESCs from said anti-Nelfa antigen binding protein.

The ESCs that bind to the anti-Nelfa antigen binding protein may be identified by methods known in the art. For example, ESCs binding to said anti-Nelfa antigen binding protein may be identified using single cell sorting, fluorescent activated cell sorting or magnetic cell sorting.

The ESCs may be isolated from the anti-Nelfa binding protein by methods known in the art. For example, the anti-Nelfa binding protein may be washed or depleted from the ESCs using an acid wash.

In some embodiments, the anti-Nelfa antigen binding protein is selected from the group consisting of a monoclonal antibody, a recombinant antibody, a polyclonal antibody, a chimeric antibody, a humanized antibody, a bispecific antibody, a heteroconjugate antibody, a single variable domain, a domain antibody, an antigen binding fragment, a immunologically effective fragment, a single chain Fv, a single chain antibody, a univalent antibody lacking a hinge region, a minibody, a diabody, and a tandem antibody.

The present invention also provides a method of inducing totipotency in an embryonic stem cell (ESC) in culture by inducing expression of Nelfa. In one embodiment, the method comprises contacting and incubating said ESC with one or more of a metabolic regulator, a small molecule compound, a chemical, a virus, a nucleic acid or a polypeptide to induce expression of Nelfa.

It will generally be understood that any metabolic regulator, small molecule compound, chemical, nucleic acid or polypeptide that induces expression of Nelfa may be suitable for use in the methods of the invention. In one embodiment, the metabolic regulator is selected from the group consisting of metabolites, metabolic intermediates, purines and pyrimidines, fatty acids, metabolic enzyme activators and inhibitors, glycolytic inhibitors, FDA approved drugs, dehydroepiandrosterone, L-buthionine sulfoximine, 3-bromopyruvate, 2-deoxy-D-glucose, dichloroacetate, GW9662, acetate, lactate, glucose, imatinib, pyruvate and amino acids. In a preferred embodiment, the metabolic regulator is selected from the group consisting of 2-deoxy-D-glucose, 3-bromopyruvate and imatinib.

In another embodiment, the nucleic acid is selected from the group consisting of genomic DNA, microRNA, siRNA, RNA and cDNA. In a preferred embodiment, the nucleic acid is an siRNA.

Examples of viruses that may be suitable for inducing Nelfa expression include but are not limited to lentivirus, retrovirus or adenovirus.

The embryonic stem cell may be contacted or incubated with the one or more of a metabolic regulator, a small molecule compound, a chemical, a virus, nucleic acid or polypeptide continuously or intermittently over a period of time.

The present invention also provides the use of a metabolic regulator, a nucleic acid, a small molecule, a chemical, a polypeptide or a virus for inducing totipotency in an embryonic stem cell.

The present invention further provides a cell comprising an expression vector encoding Nelfa operably linked to a promoter. In some embodiments, the cell comprising an expression vector is an embryonic stem cell. In other embodiments, the ESC is a mammalian ESC. Examples of mammalian ESCs include but are not limited to mouse, human and macaque stem cells. In a preferred embodiment, the ESC is a human ESC.

The cell comprising an expression vector encoding Nelfa may be operably linked to an inducible promoter. Inducible promoters may be chemically induced, temperature induced, light induced or hormone induced Examples of chemically inducible promoters include but are not limited to doxycycline-inducible promoters, tetracycline-inducible promoters and hormone receptor inducible promoters.

In a preferred embodiment, the inducible promoter is a doxycycline-inducible promoter.

The expression vector in some embodiments comprises a reporter gene. It will be appreciated that reporter genes are well known in the art. Suitable examples of reporter genes include but are not limited to green fluorescent protein (GFP), red fluorescent protein (RFP), yellow fluorescent protein (YFP), streptavidin, β-galactosidase and luciferase. In a preferred embodiment, the reporter gene is green fluorescent protein (GFP) or streptavidin.

The present invention also provides a kit comprising at least one of a metabolic regulator, a nucleic acid, a polypeptide, a small molecule, a virus or a chemical when used in the method as described herein. The kit may further comprise instructions for use.

The present invention also provides a method of improving the reprogramming efficiency of a somatic cell into an induced pluripotent stem cell (iPSC), comprising contacting and incubating the somatic cell with one or more of a metabolic regulator, a small molecule compound, a chemical, a virus, a nucleic acid or a polypeptide to induce expression of Nelfa.

Examples of viruses that are suitable include lentivirus, retrovirus or adenovirus.

The somatic cell may be contacted or incubated with the one or more of a metabolic regulator, small molecule compound, chemical, virus, nucleic acid or polypeptide continuously or intermittently over a period of time.

Examples of somatic cells that may be reprogrammed include mammalian cells. In a preferred embodiment, the somatic cell is a mouse or human cell. Examples of suitable mouse or human somatic cells include but are not limited to fibroblast cells, neuronal progenitors, B-cells, keratinocytes, mononuclear cells, T-cells and myeloid cells. Fibroblast cells may be from various organs including cardiac fibroblasts, lung fibroblasts, periodontal ligament fibroblasts such embryonic fibroblast cells, neonatal foreskin fibroblast cells and dermal fibroblast cells. It will be generally understood that this list is not limiting and any somatic cell may be reprogrammed with the method of the invention.

In a preferred embodiment, the somatic cell is selected from the group consisting of an embryonic fibroblast cell, a neonatal foreskin fibroblast cell, a neuronal progenitor cell and a B-cell.

The improvement in reprogramming efficiency may be determined by comparing a preselected phenotype in an iPSC where Nelfa expression was induced to an iPSC where Nelfa expression was not induced, wherein an increased level of expression or increased rate of expression of the preselected phenotype indicates an improvement in reprogramming efficiency. The preselected phenotype may be a characteristic of potency such as cell morphology, expression of markers of specific potency states or markers of specific lineages, ability of mouse stem cells to contribute to germline transmission in mouse chimeras, ability of stem cells to contribute to the embryo proper using tetraploid embryo complementation assays, teratoma formation of stem cells, formation of embryoid bodies and inactive X chromosome reactivation. In one embodiment, the preselected phenotype is selected from the group consisting of pluripotent marker gene expression, surface marker expression, alkaline phosphatase staining and teratoma formation. Examples of pluripotent marker genes include but are not limited to Oct4, Nanog, Sox2, Klf2, Klf4 and Esrrb. Examples of surface markers include but are not limited to SSEA-1, SSEA-4, TRA-1-60, TRA-1-81, CD73, CD49d, CD54 or CD326.

The present invention also provides a method of reprogramming a somatic cell into a totipotent stem cell comprising contacting and incubating said somatic cell with one or more of a metabolic regulator, a small molecule compound, a chemical, a nucleic acid, a virus or a polypeptide to induce expression of Nelfa.

The present invention also provides a use of one or more of a metabolic regulator, a nucleic acid, a small molecule, a chemical, a virus or a polypeptide in the manufacture of a medicament for inducing totipotency in an embryonic stem cell. The present invention also provides one or more of a metabolic regulator, a nucleic acid, a small molecule, a chemical, a virus or a polypeptide for use in inducing totipotency in an embryonic stem cell.

The present invention also provides a use of one or more of a metabolic regulator, a small molecule compound, a chemical, a virus, a nucleic acid or a polypeptide in the manufacture of a medicament for improving the reprogramming efficiency of a somatic cell into an induced pluripotent stem cell (iPSC), wherein the somatic cell is to be contacted and incubated with the medicament to induce expression of Nelfa.

The present invention also provides one or more of a metabolic regulator, a small molecule compound, a chemical, a virus, a nucleic acid or a polypeptide for use in improving the reprogramming efficiency of a somatic cell into an induced pluripotent stem cell (iPSC), wherein the somatic cell is to be contacted and incubated with the one or more metabolic regulator, small molecule compound, chemical, virus, nucleic acid or polypeptide to induce expression of Nelfa.

The present invention also provides a use of one or more of a metabolic regulator, a small molecule compound, a chemical, a nucleic acid, a virus or a polypeptide in the manufacture of a medicament for reprogramming a somatic cell into a totipotent stem cell, wherein the somatic cell is to be contacted and incubated with the medicament to induce expression of Nelfa.

The present invention also provides one or more of a metabolic regulator, a small molecule compound, a chemical, a nucleic acid, a virus or a polypeptide for use in reprogramming a somatic cell into a totipotent stem cell, wherein the somatic cell is to be contacted and incubated with the one or more metabolic regulator, small molecule compound, chemical, nucleic acid, virus or polypeptide to induce expression of Nelfa.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Material and Methods

Cell Culture

Unless otherwise stated, all mESC lines were cultured in serum-containing ESC medium containing Knockout DMEM, 15% FCS, L-Glutamine, non-essential amino acids, penicillin/streptomycin, 2-mercaptoethanol and supplemented with LIF, 1 µM PD0325901 and 3 M CHIR99021 (2i'). For serum-free 'naïve' culture condition, mESCs were grown in N2B27 medium supplemented with LIF and 2i. For 2-DG experiments, ESCs were grown in serum-containing ESC medium with 4 mM 2-DG (Sigma; D8375) for up to 4 days. For MYC inhibitor treatment, ESCs were grown in serum-containing ESC medium with 64 M MYC inhibitor, 10058-F4 (Abcam), for 3 days.

Induction of Nelfa Expression

Mouse ES cells are grown in standard culture medium containing 4 mM of 2-DG inhibitor for 4 days, at 37° C. with 5% $CO_2$. Culture medium containing 2-DG is changed every day during the induction. NELFA is expression is upregulated in this process. In a second system, where NELFA is under the control of a Dox inducible promoter, the expression is induced by culturing the ES cells with culture medium containing 0.4 µg/mL of Doxycycline for 16 hours at 37° C. with 5% $CO_2$.

Reprogramming of Somatic Cells

Mouse/human NELFA lentiviral construct can be cloned into pHAGE-EF1α-IRES-zGreen/mCherry or pHAGE-pTRE3G-IRES-zGreen/mCherry vector for constitutive or inducible expression respectively. In general, mouse or human fibroblast will be infected with lentiviral reprogramming factors (Oct4, Sox2, Klf4, c-Myc, OSKM) with or without NELFA lentivirus. Briefly, cells are seeded at a density $1.5 \times 10^5$ per well of a 6 well plate 24 hours prior to infection, and 10-20 µl of concentrated lentiviral combinations (OSKM only or OSKM plus NELFA) used for transduction in presence of polybrene (8 µg/mL). Cells are cultured in MEF medium (DMEM, 10% FCS, 1× Pen-Strep, 1× Glutamax) for 48 hours before FACS enrichment for positive transduced cells. For Dox inducible systems, doxycycline will be supplemented to the culture medium (0.4-2 µg/mL) for 16 hours before FACS sorting. Sorted cells can then be re-plated onto 6 well plates and cultured in MEF medium for 1 week before switching to mTeSR (Stem cell technologies) or 2i culture medium (Knockout DMEM, 15% FCS, L-Glutamine, non-essential amino acids, penicillin/streptomycin, 2-mercaptoethanol and supplemented with LIF, 1 µM PD0325901 and 3 µM CHIR99021) for human and mouse cells respectively. To evaluate the reprogramming efficiency in presence and absence of NELFA, immunostaining for pluripotency makers (SSEA1, SSEA4, TRA-1-60, TRA-1-81) can be carried out and number of positive cells scored and compared between the different treatments.

Generation of NELFA Reporter and Dox-Inducible mESC Lines

For NELFA-StrepHA-P2A-EGFP reporter ESC line, a donor vector harboring a Strep-HA-P2A-EGFP cassette flanked by NELFA left and right homology arms (826 bp and 924 bp respectively) was co-transfected with the CRISPR-Cas9 sgRNA cloning vector, pX458, containing the Nelfa sgRNA sequence (GCTGACCCTCATCAGACCAG)(SEQ ID NO: 1). Positive transfectants were GFP-sorted and targeted single clones validated by genotyping.

For generation of the Dox-inducible NELFA overexpression ESC lines, the Tet-On 3G inducible expression system (ClonTech) was used. Briefly, both NELFA-Strep-HA and NELFA-Strep-HA-P2A-EGFP constructs were cloned into the pTRE3G vector, linearized with ScaI and co-transfected with pCAG-IRES-puromycin into E14 mESCs stably expressing EF1α-Tet3G. ESCs were kept under constant puromycin and G418 selection. 0.4 µg/ml of Dox was used for induction of NELFA expression.

For generation of histone H1-mCherry stable mESCs, mouse H1e-mCherry fusion DNA sequence was ordered as a Gblock from IDT, amplified and inserted into the expression plasmid, pCAG-IRES-hygromycin. The pCAG-H1-mCherry-IRES-hygromycin plasmid was linearized with FspI and transfected into both NELFA-StrepHA-P2A-EGFP reporter mESCs and Dox-inducible pTRE-NELFA-StrepHA mESCs. Transfected cells were selected with hygromycin B (150 µg/ml) for 4 days before single colony sub-cloning.

For generation of Dux-overexpressing mESCs, E14 mESCs was transfected with the mouse codon optimized Tet-inducible Dux plasmid pCW57.1-mDux-CA (Addgene plasmid #99284) that has been linearized with ScaI. Puromycin selection (2 µg/ml) was carried out for 1 week to enrich for stable transfectants before single colony sub-cloning. Selected sub-clones were kept under constant puromycin selection to prevent transgene silencing.

siRNA Transfection siRNAs were purchased from GE Dharmacon and Qiagen and transfected into mESCs using Lipofectamine RNAiMAX according to manufacturer's instructions. Both forward and reverse transfections were carried out. The final concentration of siRNA used was 40 nM per transfection and the effect of knockdown analyzed at 72 h. The siRNAs are listed in Table 1.

TABLE 1

| List of siRNAs used Dharmacon | |
|---|---|
| ON-TARGETplus Mouse Nelfa (24116) siRNA | L-050757-01-0020 |
| ON-TARGETplus Mouse Nelfb (58202) siRNA | L-048011-01-0005 |
| ON-TARGETplus Mouse Nelfe (27632) siRNA | L-052825-01-0020 |
| ON-TARGETplus Mouse Max (17187) siRNA | L-047274-01-0005 |
| ON-TARGETplus Mouse Mycn (18109) siRNA | L-058793-01-0005 |
| ON-TARGETplus Mouse Myc (17869) siRNA | L-040813-00-0005 |
| ON-TARGETplus Mouse Zic3 (22773) siRNA | L-045667-00-0005 |
| ON-TARGETplus Mouse Esrra (26379) siRNA | L-040772-00-0005 |
| ON-TARGETplus Mouse Esrrb (26380) siRNA | L-059177-02-000 |
| ON-TARGETplus Mouse Hif1a (15251) siRNA | L-040638-00-0005 |
| ON-TARGETplus Mouse Nr5a2 (26424) siRNA | L-060606-00-0005 |
| ON-TARGETplus Mouse Chaf1a (27221) siRNA | L-047044-01-0005 |
| ON-TARGETplus Non-targeting Pool siRNA | D-001810-10-20 |

| QIAGEN | |
|---|---|
| FlexiTube - GeneSolution | 1027416 |
| FlexiTube GeneSolution GS18109 for Mycn 4 siRNAs for Entrez gene 18109: | |
| SI01328768 (FlexiTube siRNA) | |
| SI01328761 (FlexiTube siRNA) | |
| SI01328754 (FlexiTube siRNA) | |
| SI01328747 (FlexiTube siRNA) | |

Immunofluorescence

Briefly mESCs were grown on gelatin-coated imaging dishes, fixed in 4% PFA for 10 min at room temperature, permeabilized and blocked in 0.1% TRITON™ X-100/1% BSA for 30 min. Cells were incubated in primary antibodies overnight at 4° C. followed by three washes in blocking buffer. Secondary antibodies were added for 1 h followed by two washes in blocking buffer and a final wash in PBS. The DAPI was used as a nuclear counterstain. Mouse embryos were fixed in 4% PFA for 15 min at room temperature, permeabilized and blocked in 0.15% TRITON™ X-100/1% BSA for 30 min. Primary antibodies were added overnight, washed three times in blocking buffer and secondary antibodies containing DAPI was added for 2 h. The antibodies used are listed in Table 2.

TABLE 2

| List of antibodies used. | | | | | |
|---|---|---|---|---|---|
| Antibody | Company | Catalog No. | Lot/Batch | Species | Application |
| NELF-A | Bethyl | A301-910A | A301-910A-1 | rabbit | Immunofluorescence (1:600) |
| NELF-A | Sigma | SAB1406594 | 09057 | mouse | Immunofluorescence (1:250) |

TABLE 2-continued

List of antibodies used.

| Antibody | Company | Catalog No. | Lot/Batch | Species | Application |
|---|---|---|---|---|---|
| Oct-3/4 | Santa Cruz | sc-8628 | I2115 | Goat | Immuno-fluorescence (1:500) |
| GFP | Abcam | ab6673 | GR202861-4 | goat | Immuno-fluorescence (1:600) |
| MuERVL-Gag | Epigentek | A-2801-100 | 607021 | rabbit | Immuno-fluorescence (1:400) |
| Zscan4 | Abnova | H00201516-B01P | G1211 | mouse | Immuno-fluorescence (1:500) |
| HA | Biolegend | 901501 | B220766 | mouse | Immuno-fluorescence (1:250) Western (1:1000) |
| HA | Abcam | ab9110 | GR304617-2/ GR235874-6 | rabbit | Immuno-precipitation |
| CBP | Santa Cruz | sc-7300 | D2117 | mouse | Immuno-fluorescence (1:100) |
| NAP1 | Abcam | ab33076 | GR42793-1/ GR2712401 | rabbit | Immuno-fluorescence (1:2000) |
| mCherry | Novus | NBP1-9675255 | 91416 | mouse | Western (1:2000) |
| mCherry | Abcam | ab167453 | GR312817 | rabbit | Immuno-fluorescence (1:400) Immuno-precipitation |

RT-qPCR 0.5-1 μg of total RNA was used as input for cDNA preparation with the SensiFAST cDNA synthesis kit (Bioline; 65054). Reverse transcription was carried out with standard cycling condition as per manufacturer's instructions. Each respective cDNA was diluted 40-folds, and qPCR was conducted using the 2× PowerUp SYBR Green master mix (Thermo; A25742). Relative gene expression fold change was calculated using the delta delta CT method and statistical significance was assessed using a student's T-test. The primers used for qPCR are listed in Table 3.

TABLE 3

List of RT-qPCR primers

| | | |
|---|---|---|
| Zscan4_F | CCCTTCCTAGTGGTCGTGAATGTCTTT | SEQ ID NO: 2 |
| Zscan4_R | CTGCTGTGAAGCCATTGTGGTGAC | SEQ ID NO: 3 |
| MERVL_F | TTTCTCAAGGCCCACCAATAGT | SEQ ID NO: 4 |
| MERVL_R | GACACCTTTTTTAACTATGCGAGCT | SEQ ID NO: 5 |
| Tcstv1_F | GCCCAGAGTACAAGGTGTTCTAAT | SEQ ID NO: 6 |
| Tcstv1_R | ATTCAATCTTCGGTAGGATCTCAG | SEQ ID NO: 7 |
| Tcstv3_F | ACCAGCTGAAACATCCATCC | SEQ ID NO: 8 |
| Tcstv3_R | CCATGGATCCCTGAAGGTAA | SEQ ID NO: 9 |
| Gm2022_F | AACAGGCGCAGAGGTAAAAA | SEQ ID NO: 10 |
| Gm2022_R | GCACAGCCTCCTTACACCAT | SEQ ID NO: 11 |
| Gm4340_F | CGAGGCACTGGGTCTAAGAG | SEQ ID NO: 12 |

TABLE 3-continued

List of RT-qPCR primers

| | | |
|---|---|---|
| Gm4340_R | CCAATGAACAGGTCATGCTG | SEQ ID NO: 13 |
| NELFA_F | TGCTAGTGGACACAGTGTTCGA | SEQ ID NO: 14 |
| NELFA_R | TTGAAGCGTGTCCACTGGCC | SEQ ID NO: 15 |
| Actin_F | AGCCATGTACGTAGCCATCC | SEQ ID NO: 16 |
| Actin_R | GCTGTGGTGGTGAAGCTGTA | SEQ ID NO: 17 |
| NELFB_F | AGCGCACTCTCTTTCTCTAGGAT | SEQ ID NO: 18 |
| NELFB_R | CTGTGGAAGTGAAGAGGCAGATT | SEQ ID NO: 19 |
| NELFE_F | CTGGATTCCTTGTGCCTCAT | SEQ ID NO: 20 |
| NELFE_R | AACTCCAATCCCAAGTGCTG | SEQ ID NO: 21 |
| Endogenous Dux_qPCR_F | GGCCCTGCTATCAACTTTCAAGA | SEQ ID NO: 22 |
| Endogenous Dux_qPCR_R (FIG. 4f) | GAGCCTCTGATGGACCTCTTTG | SEQ ID NO: 23 |
| Inducible Dux_F | AGGAGGAAAACTGTCTGGCA | SEQ ID NO: 24 |
| Inducible Dux_R | CCTATTCTGGAACCAGACTC | SEQ ID NO: 25 |
| Gata3_F | GGGTTCGGATGTAAGTCGAG | SEQ ID NO: 26 |
| Gata3_R | CCACAGTGGGGTAGAGGTTG | SEQ ID NO: 27 |

Fluorescence-Activated Cell Sorting (FACS)

FACSAria Cell Sorter (BD Biosciences) was used to quantify the proportion of EGFPpositive and EGFP-negative cells from the reporter mESC lines. The Moflow sorter was used to sort EGFP-positive and EGFP-negative cells for RNA-seq and NoME-seq studies.

Nuclear Extract and Immunoprecipitation

To prepare nuclear extract, ESCs were resuspended in ice cold TMSD buffer (20 mM HEPES pH 7.5, 5 mM $MgCl_2$, 250 mM Sucrose; completed with 1 mM Dithiothreitol (DTT), 5 mM Sodium Butyrate, 1 mM Aprotinin (A), 1 mM Pepstatin (P), 1 mM Leupeptin (L) and 2 mM phenylmethane sulfonyl fluoride (PMSF)) for 10 min and collected by centrifugation (800 g, 4° C.). Next, the nuclei were released by resuspending and incubating the cell pellet with complete ice cold TMSD buffer containing 0.1% (v/v) Nonidet P-40 on ice for 10 min. The released nuclei were pelleted by centrifugation (800 g, 4° C.) and immediately lysed with ice cold lysis buffer 1 (20 mM Tris-Cl pH 7.9, 420 mM KCl, 1.5 mM $MgCl_2$, 0.2 mM EDTA) completed with 10 mM Sodium Butyrate, 0.5 mM DTT, 1 mM A/L/P and 2 mM PMSF. Nuclear lysis was carried at 4° C. with constant rotation (20 rpm) and the extract was briefly sonicated in a Biorupter (Diagenode) at high setting for 3 cycles (30 seconds on, 30 seconds off). Thereafter, the nuclear lysate was centrifuged at max speed (20,000 g, 4° C.) for 30 min and the supernatant (lysate 1) was transferred to a fresh microfuge tube. The insoluble pellet from the initial nuclear lysis was subjected to an addition round of extraction with ice cold lysis buffer 2 (20 mM Tris-Cl pH 7.9, 700 mM KCl, 1.5 mM $MgCl_2$, 0.2 mM EDTA) completed with 10 mM Sodium Butyrate, 0.5 mM DTT, 1 mM A/L/P and 2 mM PMSF. This lysis step was similarly carried out at 4° C. with constant rotation (20 rpm) and with 5 cycles of sonication (Biorupter, Diagenode) at high settings (30 seconds on, 30 seconds off). The lysate was spun at max speed (20,000 g, 4° C.) for 30 min and the supernatant (lysate 2) was transferred to a fresh microfuge tube. Both lysates were then dialyzed in BC100 (50 mM Tris-Cl pH 7.9, 2 mM EDTA, 10% Glycerol, 100 mM KCl, 0.2 mM PMSF) and combined.

500 μg to 2 mg of lysates were used per IP. For each IP, 4 μg of either HA (Cat: ab9110, Abcam), mCherry (Cat: ab167453, Abcam), normal rabbit IgG (Cat: 2729, Cell Signaling), or normal mouse IgG (Cat: 5415, Cell Signaling) antibody was used. IP was carried out overnight with constant rotation (20 rpm) at 4° C. 50 μL of protein-G agarose beads was added to each IP reaction to capture the antibody-antigen complex. This was followed by extensive washes in BC200 (50 mM Tris-Cl pH, 7.9 2 mM EDTA, 10% Glycerol, 200 mM KCl) and the IP were eluted with 2× laemmli buffer, boiled at 99° C. for 10 min before running a standard western blot.

SDS-PAGE and In-Gel Digestion

Immunoprecipitated samples were run on a SDS-PAGE using a NuPAGE 4-12% Bis Tris Gel (Invitrogen). The protein bands were excised followed by in-gel digestion, with minor modifications. Gel pieces were washed with 50 μL of 50 mM ammonium bicarbonate and destained with 50 μL of 50% acetonitrile/25 mM ammonium bicarbonate for 10 min. Reduction was carried out by covering the gel pieces with 10 mM DTT for 30 min at 56° C.; alkylation was carried out with 55 mM iodoacetamide for 15 min in the dark at room temperature. 50 μL of 50 mM ammonium bicarbonate was used for washing and 50 μL of 100% acetonitrile was used for shrinking twice for 10 min. 30 μL of 13 ng/μL sequencing-grade trypsin (Promega) was added to each well for 30 min at 4° C. before 25 mM ammonium bicarbonate was added to cover the gel pieces. Samples were incubated for 3 h at 37° C. Supernatants containing peptides were cleared by centrifugation. 20 μL of 5% formic acid was added to each well followed by 20 μL of 100% acetonitrile for peptide extraction. Both steps were repeated and extracted were vacuum dried.

LC/MS Analysis

Reconstituted peptides were analysed using an EASY-nLC 1000 (Proxeon, Fisher Scientific) attached to a Fusion (Thermo Fisher Scientific). Peptides were enriched using a C18 precolumn and separated on a 50 cm analytical column (EASY-Spray Columns, Thermo Fisher Scientific) at 50° C. using a 5 min isocratic gradient of 5% buffer B, followed by a 120 min gradient ranging from 8 to 38% buffer B and a 15 min gradient from 38 to 100% buffer B and stayed for 15 min at 100% buffer B. Survey full scan MS spectra (m/z 310-1510) were acquired with a resolution of 120 k, an AGC target of $5\times10^5$, and a maximum injection time of 200 ms. The MS/MS scans were acquired with a resolution of 15 k, an AGC target of $3\times10^4$, a maximum injection time of 50 ms, first mass filter set at m/z of 120, and dynamic exclusion of 30 s.

Data Processing and Database Search

Data were processed using MaxQuant (Version 1.6.0.1) against a database consisting of uniprot 2018-01 mouse database, histone H1e-mCherry fusion protein and 245 commonly observed contaminants. Database searches were performed with tryptic specificity allowing maximum two missed cleavages and two labeled amino acids as well as an initial mass tolerance of 4.5 ppm for precursor ions and 20 ppm for fragment ions. Cysteine carbamidomethylation was searched as a fixed modification, and N-acetylation, oxidized methionine were searched as variable modifications. Maximum false discovery rates were set to 0.01 for both protein and peptide. Proteins were considered identified when supported by at least one unique peptide with a minimum length of seven amino acids.

RNA-Seq

Three RNA-seq experiments were performed on mESCs under different conditions, each with two biological replicates. Total RNA was isolated from mESCs using the Zymo RNA miniprep kit following manufacturer's instructions. Ribosomal depletion was carried using the NEBNext rRNA depletion kit and RNA-seq libraries were constructed using the NEBNext RNA Ultra II directional library kit as per manufacturer's instructions, and sequenced on the NextSeq 500 sequencer. The ERCC spike-in controls (cat #4456740) were included in both RNA-Seq libraries generated from Dox-inducible NELFA-EGFP and 2DG-treated NELFA reporter mESCs for downstream normalization purposes.

NOMe-Seq

NOMe-seq experiment was carried out with three biological replicates. Nuclei isolation and artificial GpC methylation using M.CviPl for NoME-Seq was carried out as described previously with slight modifications. Briefly, mESCs was re-suspended in a hypotonic lysis buffer (10 mM Tris-Cl pH 7.4, 10 mM NaCl, 3 mM $MgCl_2$) on ice for 10 minutes before adding Nonidet P-40 (final concentration 10% v/v) to release nuclei. The released nuclei were collected (800 g, 4° C., 5 min), washed once with the hypotonic lysis buffer, and re-collected (800 g, 4° C., 5 min) before re-suspending in 1×GpC buffer (NEB) supplemented with S-adenosyl-methionine (SAM) (final concentration 160 M), M.CviPI (50 U, NEB), and unmethylated lambda DNA (Fermentas, 1% of total genomic DNA). GpC methylation was carried out at 37° C. for 30 min and the reaction was boosted with the addition of fresh M.CviPI (25 U) and SAM (final concentration 160 M) for another 15 min at 37° C. Next, nuclei were lysed with the addition of nuclei lysis buffer (20 mM Tris-Cl pH 7.9, 600 mM NaCl, 1% (v/v) SDS, 10 mM EDTA) and was subsequently digested with RNase A and Proteinase K. M.CviPI methylated genomic DNA was purified with 1 volume of SPRI (solid phase reversible immobilization) beads and 1 μg of purified DNA was used as input for sequencing library generation using the NEBNext DNA Ultra II kit (NEB, Cat: E7645S) with methylated adapters (NEB, Cat: E7535S).

Gene Clustering to Detect Function Groups

The transcriptome data for the seven stages of mouse pre-implantation embryos was downloaded from the GEO dataset, GSE66582. Gene clustering was done in the R language (www.r-project.org/). Genes that are actively transcribed in at least one stage (FPKM≥5) were selected for clustering analysis. Gene-wise scaling was applied across all the stages such that for a given gene, the highest stage expression is 1 and the lowest 0 by the formula:

$$x_{scaled} = \frac{x - \min(x)}{\max(x) - \min(x)},$$

where x is a stage expression vector for a given gene. Gene distance Matrix was then calculated based on the uncentered correlation similarity method using the Dist function from the amap package (cran.r-project.org/web/packages/amap/index.html), and the hclust function from R standard stats package was applied to classify these genes into 10 clusters using the Hierarchical Average Linkage Clustering method. 7 out of 10 clusters that showed the most significant variations were presented.

RNA-Seq Data Analysis

Single- and Paired-end raw sequencing reads were trimmed with Trim Galore (v0.4.2_dev; www.bioinformatics.babraham.ac.uk/projects/trim_galore/) with parameters: --trim-n (single-end, NELFA reporter mESCs) or -paired (paired-end, Doxinducible NELFA-EGFP and 2DG-treated NELFA reporter mESCs). Cleaned reads were then mapped to the mouse GRCm38 reference genome, guided by the vM9 gene model from the GENCODE project using the RSEM pipeline (v1.1.11). For repetitive elements analysis, the repeat annotation in mm10 was obtained from the UCSC genome browser track repeatMasker. Reads mapping and quantification of individual repetitive element expression were carried out by using the RepEnrich pipeline, which takes a two-step approach. Briefly, reads were mapped to the mouse genome (mm10) by Bowtie (v1.1.2), and separated into multiple-mapped and uniquely mapped reads. Unique reads were assigned to the repetitive elements based on coordinate overlap; multiple mapped reads were subsequently mapped to repetitive element psuedogenomes generated from concatenating occurrences of individual repetitive elements. If a read maps to more than one repetitive element, each repetitive element gets a fraction of count (1/# of repetitive elements aligned). DeSeq2 (v1.16.1) was applied to both differential gene and repetitive element expression analyses with default settings, except the calculation of sample normalization factors, and using biological replicates as covariant. Specifically, in both differential gene and repetitive element expression analyses, sample normalization factors were calculated from ERCC spike-ins for Doxinducible NELFA-EGFP and 2DG-treated NELFA reporter mESCs; while samples normalization factors were calculated from the expression of all the annotated genes for NELFA reporter mESCs. Genes and repetitive-elements are considered as differentially expressed if they show ≥2-fold difference in expressions with adjusted p-value≤0.01 after correcting for multiple testing by FDR (Benjamini and Hochberg false discovery rate).

Comparison Analysis

To compare the expression profiles between the 2C-like cells generated in the disclosure with those established in other labs, RNA-seq reads from Akiyama et al. (Zscan4$^{high}$, GSE51682) and Hendrickson et al. (siCAF1 and Dux overexpression, GSE85627) were downloaded from the NCBI GEO repository and processed as described above. The scatter and box plots were generated using ggplot2 in R.

The published ChIP-seq data for DUX is downloaded from GSE85632, and processed Briefly, paired-end raw sequencing reads were processed with Trim Galore to trim low-quality reads and remove adapters (parameter: --trim-n --paired). Cleaned reads were then mapped to mm10 by Bowtie2(v.2.2.9) with parameters: -N 1 -L 25. Aligned reads with low confidence (mapping quality<10) and PCR duplicates are removed using SAMtools(v1.4). Peaks were called with MACS2 "callpeak" with default parameter.

Motif Discovery and Enrichment Analysis

Homer2 (v4.9.1) was used for motif discovery and enrichment analysis. For motifs across promoters, the search space is defined as a 4 kb window centered at TSS (findMotifs.pl geneInput.txt mouse out/ -start -2000 -end 2000 -len 8,12 -p 10); for motifs at ChIP-Seq binding sites, the search space is defined as a 50 bp window centered at peak summit (findMotifsGenome.pl peakInput.bed mm10 out/ -size 50 -p 10).

NOMe-Seq Data Analysis

Single-end raw reads were trimmed by Trim Galore to remove adapters and low-quality end bases. Reference sequence was prepared by appending lambda genome to mm10. Alignments were performed for each biological replicate separately by Bismark v0.19.0 with parameters: --non_directional --bowtie2 -p 20 -N 1 -L 25. Aligned reads were de-duplicated with deduplicate_bismark and low quality reads were removed by SAMtools (v1.4). Biological replicates were merged using SAMtools (v1.4), and genome-wide cytosine methylation profile across sites covered by at least one read was generated by bismark_methylation_extractor with parameters: --merge_non_CpG --yacht. Common SNP set v142 for mm10 was downloaded from the UCSC genome browser and SNP-overlapping sites were filtered out from the genome-wide cytosine methylation profile. Cytosine methylation calls from both strands were merged to calculate per-context rather than per-Cytosine DNA methylation. Due to the nature of NOMe-seq, the analysis was only focused on WCG (W: A/T) for charting DNA methylation and HCG (H: A/C/T) chromatin accessibility.

NDR calling: Nucleosome depleted regions (NDRs) were called from the DNA methylation in GCH sites. Briefly, the genome was split into 100 bp sliding windows with 20 bp steps. The C and T read counts were summed up across every GCH sites within each window and p-values ($\chi^2$-test) for the enrichment of unmethylated GCH sites of each window were calculated as the differences to the genome background. Only the significant windows with −log 10(p-value)>5 and a minimum size of 140 bp were retained for the downstream analysis.

DNA methylation distribution: For boxplots of DNA methylation across different genomic features, WCG and GCH probes were defined as containing 50 consecutive WCG sites and 100 GCH sites respectively. Only WCG and GCH probes of ≥10 coverage were kept for analysis. BEDOPS v2.4.28 was used to identify probes that overlap genomic features by at least 1 bp: promoters (probes overlapping 1000 bp upstream of genes), promoter2C (probes overlapping 1000 bp upstream of 2C genes compiled from Zscan4$^{high}$, siCAF1, DUX$^{high}$, NELFA$^{high}$, and NELFA(+dox)), CpGisland (probes overlapping CpGisland downloaded from UCSC genome browser). Metaplots of DNA methylation (WCG DNA methylation) and chromatin accessibility (GCH DNA methylation) were performed by deeptools v2.5.3. Genomic features interrogated including canonical transcripts and repetitive elements were obtained from the UCSC genome browser.

Functional Enrichment Analysis

The functions enrichGO and gseKEGG in the package clusterProfiler was used to carry out Gene Ontology (GO) over-representation test and Kyoto Encyclopedia of Genes and Genomes (KEGG) gene set enrichment analysis (GSEA) respectively. For GO analysis, p-values were calculated using hypergeometric distribution, and for GSEA analysis, p-values were calculated based on one million permutations. For both types of analyses, pathways were considered as significant if the FDR-corrected p-value is ≤0.05.

Gene Regulatory Network Construction

The Iregulon (v1.3) Cytoscape plugin was applied to predict master factor and targets from the input gene list with the following main parameters: "20 kb centered around TSS" for "Putative regulatory region", 20 kb centered around TSS (7 species)" for "Motif ranking database", "20 kb centered around TSS (ChIP-seq derived)" for "Track ranking database", "10K(9713 PWMS)" for "Motif collection", and "1120 ChIP-seq tracks (ENCODE raw signals)" for "Track collection". The regulatory network showing the candidate factors and their predicted direct targets was constructed in Cytoscape (v3.5.1).

Data Availability

All sequencing data have been deposited in the Gene Expression Omnibus database under the GEO Accession GSE113671.

Example 1

The Maternal Factor, NELFA, is Heterogeneously Expressed in mESCs

Figure 1B:
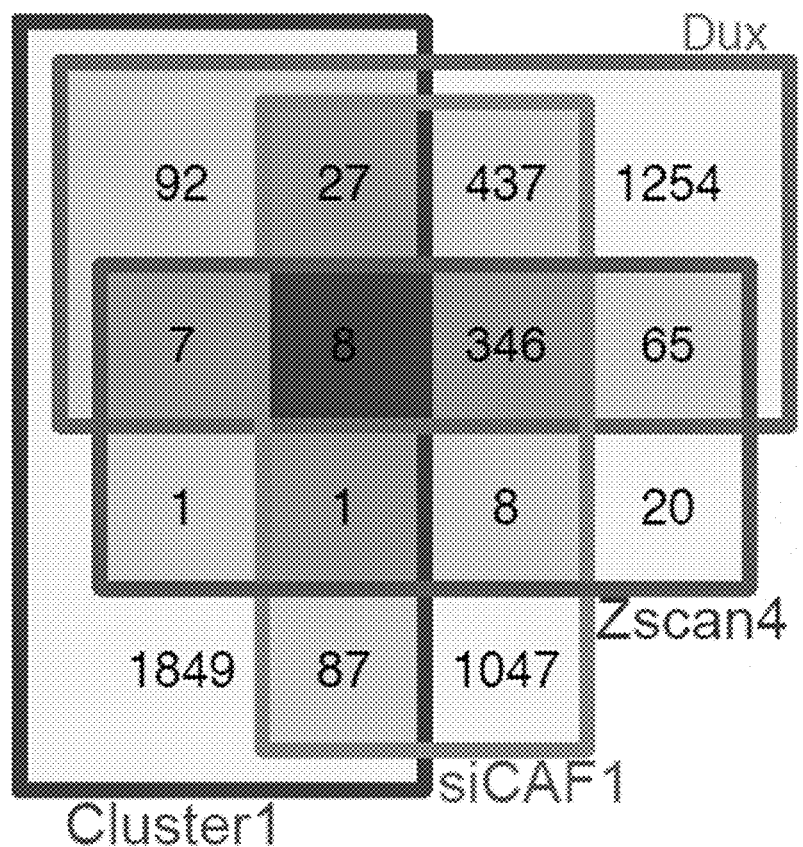
FIG. 1b is a Venn diagram indicating that eight genes from Cluster 1 (C1) were also upregulated in 2C-like cells of different provenance (namely, Zscan4-positive mESCs, Dux-overexpressing mESCs and CAF-1 knockdown mESCs).
Figure 1C:
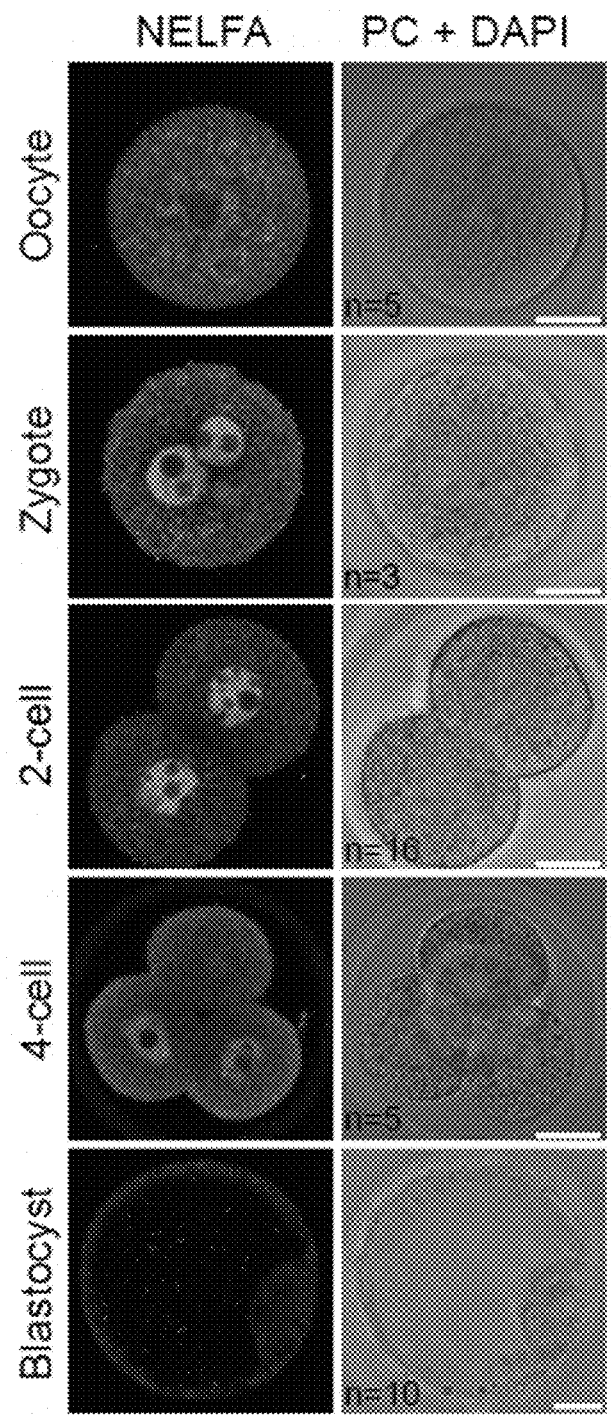
FIG. 1c is a set of microscopy images depicting immunofluorescence for NELFA in the mouse oocyte, zygote, 2-cell embryo, 4-cell embryo and blastocyst. A single focal plane is shown for each. n indicates the total number of embryos analyzed in at least 2 independent experiments. PC: Phase contrast. Scale bar=20 µm.
Figure 1D:
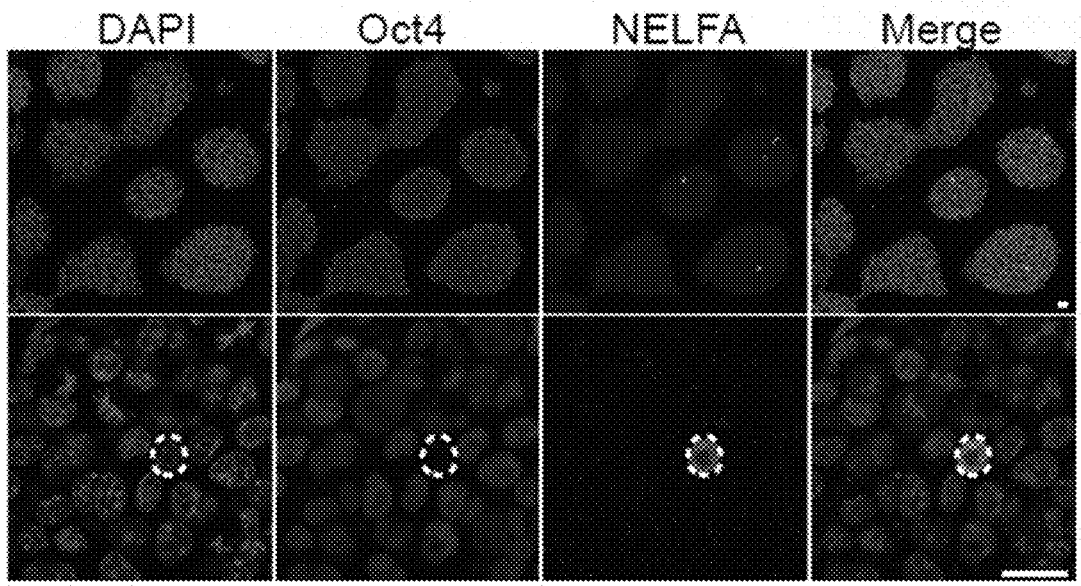
FIG. 1d is a set of microscopy images depicting that immunofluorescence for NELFA (circled) and lack of Oct4 (circled) in mESCs revealed a rare NELFA-positive subpopulation. 3 independent experiments were performed. Scale bar=20 µm.
Figure 1E:
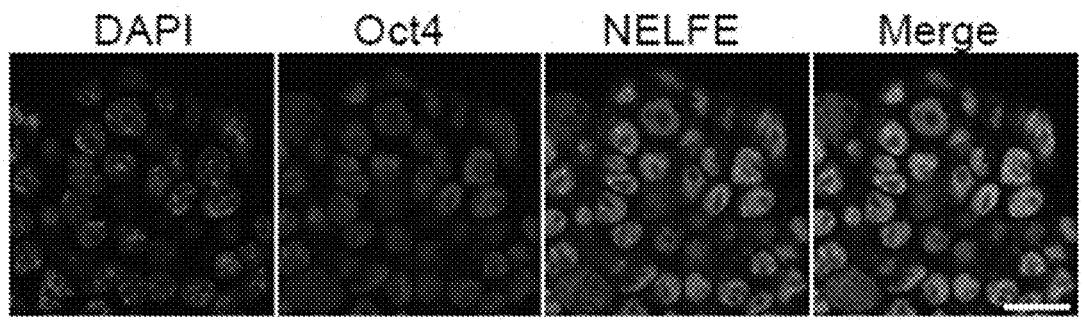
FIG. 1e is a set of microscopy images depicting immunofluorescence for NELFE and Oct4 in mESCs indicating that NELFE expression is not heterogeneous. 3 independent experiments were performed. 3 independent experiments were performed. Scale bar=20 µm.
Figure 1F:
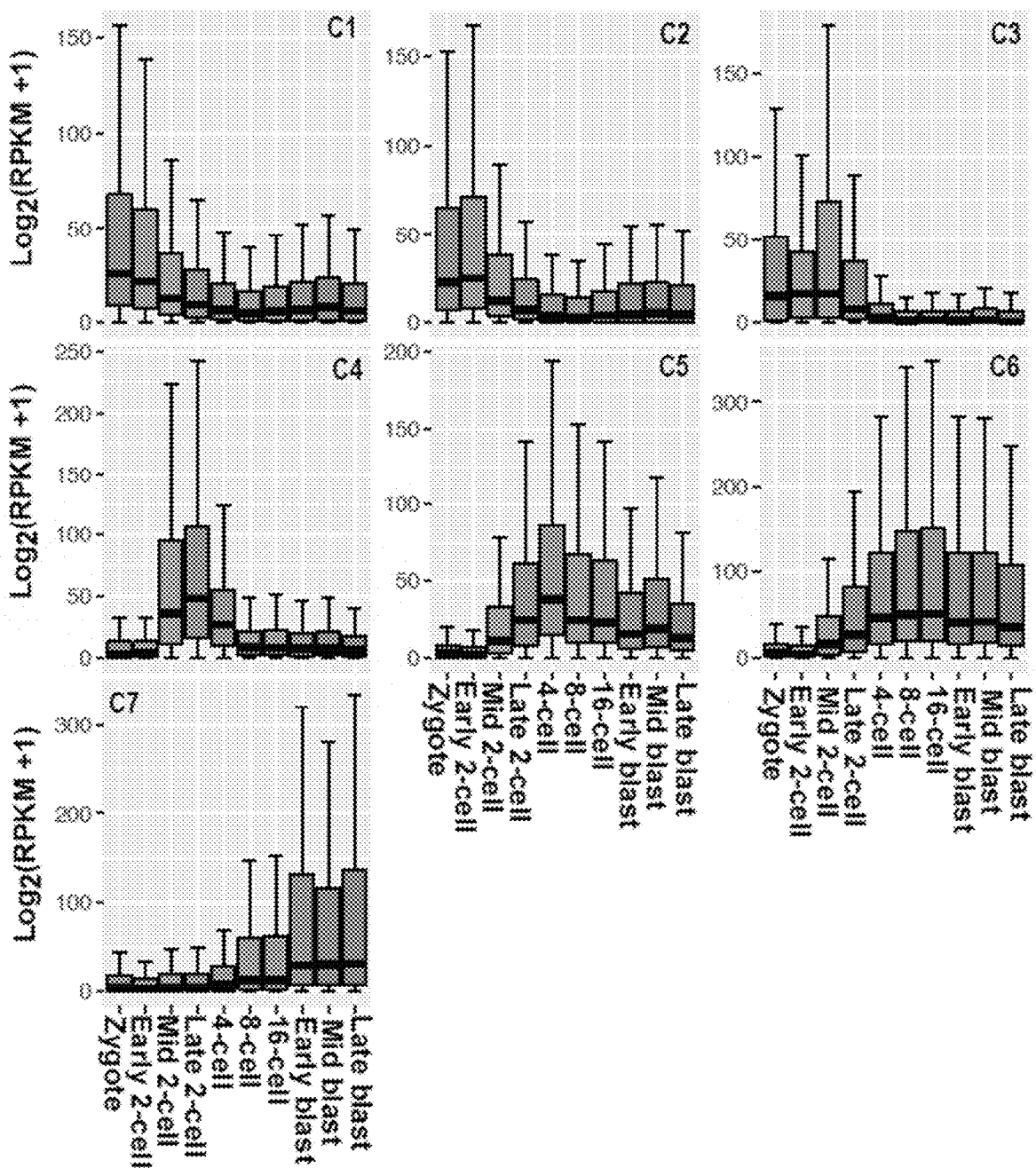
FIG. 1f is a set of boxplots showing distinct stage-specific expression patterns during mouse preimplantation development. C1-C7, the seven clusters identified from FIG. 1a. Center line: median; box limits: lower and upper quartiles; upper whisker: the smaller value of the maximum value and upper quantile plus 1.5× the interquartile range; lower whisker: the larger value of the minimum value and the lower quantile minus 1.5× the interquartile range.

The transcriptomes of mouse pre-implantation embryos from 7 developmental stages, including mESCs was interrogated as part of the analysis. Genes that are expressed in at least 1 stage (fragments per kilobase per million (FPKM) ≥5) were assorted into 10 clusters by hierarchical complete linkage clustering method using an uncentered correlation similarity matrix, and the 7 clusters that displayed the most significant variations were displayed (FIG. 1a). Cohorts of genes that exhibited stage-specific expression patterns were successfully identified, including genes with known developmental functions and temporally regulated expression, such as Nanog and Klf4 (Cluster 7; ESC-specific) and Dux and Zscan4 (Cluster 3; 2C-specific). To further validate the approach, an independent single-cell transcriptome dataset from pre-implantation mouse embryos was examined, and the stage-specific expression patterns observed in these 7 clusters was successfully recapitulated (FIG. 1f).

Next, Gene Ontology (GO) analysis for each of these gene clusters was carried out and 6 out of 7 clusters showed functional enrichment (FIG. 1a). Cluster 1 (C1)—containing 2072 genes whose expression is restricted to the oocyte and early 2C-stage—was of particular interest, given that maternal and/or early embryonic factors present at these stages are likely to contribute to the ZGA and the totipotent state. Notably, transcriptional and chromatin-based processes, such as "Chromatin binding" (GO:0003682) and "Transcription from RNA polymerase II promoter" (GO:0006366), were enriched in this cluster; this was consistent with recent findings showing that extensive chromatin reorganization and transcriptional activation occurring in early embryos are important for reprogramming towards totipotency.

Figure 1G:
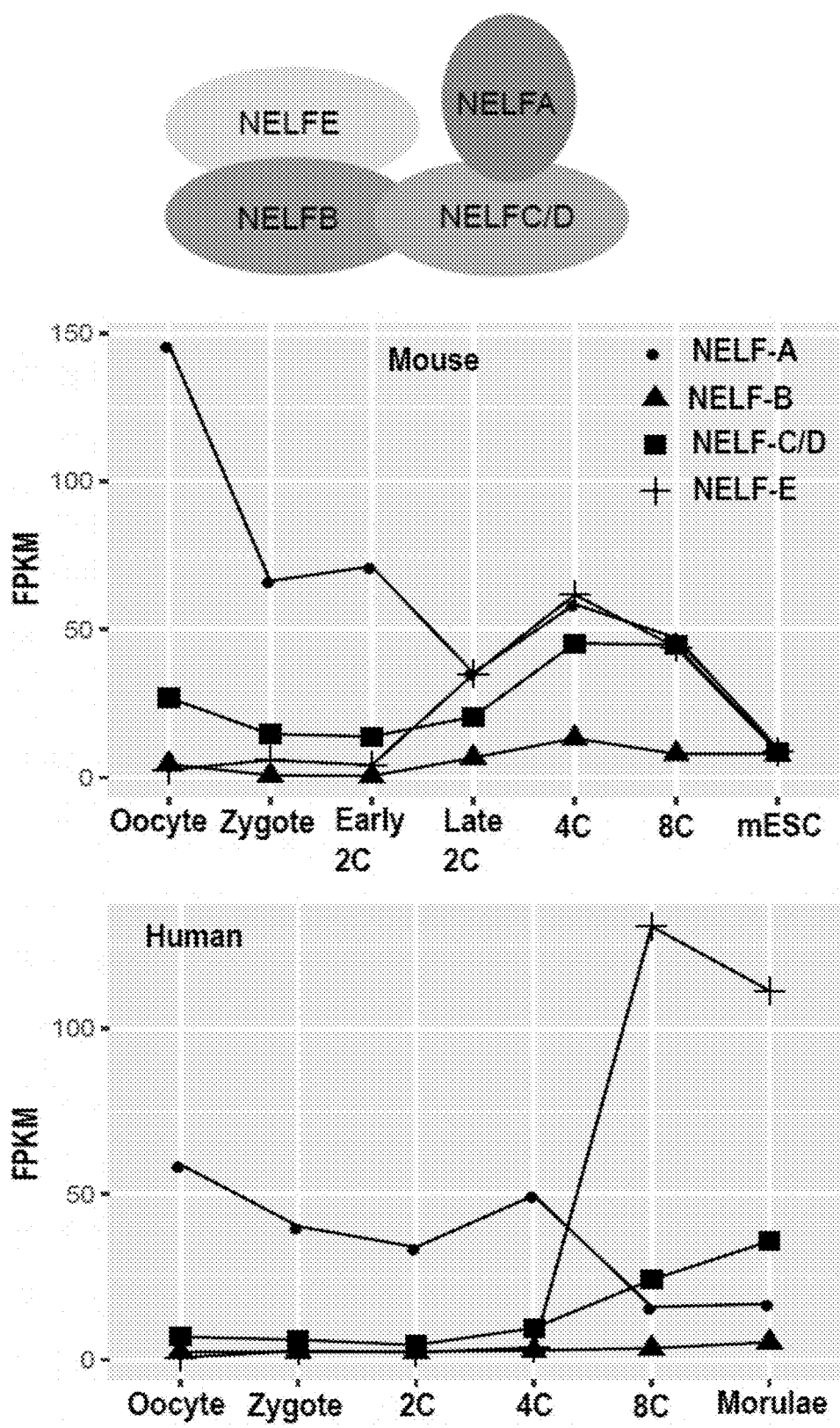
FIG. 1g is a diagram and a pair of line graphs depicting that NELFA shows distinct stage-specific expression patterns in both mouse and human pre-implantation embryos. Top panel: schematic depiction of NELF (Negative ELongation Factor) complex, consisting of NELFA, NELFB, NELFC/D and NELFE subunits. Middle and bottom panels: relative expressions of NELF subunits in mouse and human pre-implantation embryos respectively. Thus.

To identify novel regulators of the 2C-state, genes from the C1 cluster were intersected with those that are significantly upregulated (adjusted p-value≤0.01 and fold-change≥2) in the previously reported 2C-like mESC transcriptome datasets (namely, Zscan4-positive mESCs and 2C-like cells induced by Dux over-expression and 2C-like cells induced by CAF-1 depletion), all of which are reported to share transcriptional features similar to the 2C embryos in vivo. This approach identified 8 genes within the C1 cluster that are commonly expressed across the datasets analyzed—Nelfa, Sh3kbp1, Trim75, Abhd3, Strip2, Gm839, Slc25a31 and GaInt3 (FIG. 1b). Of these, only NELFA is a known transcriptional regulator, and it is annotated with the relevant C1 GO terms "Chromatin binding" and "Transcription from RNA polymerase II promoter". NELFA is one of the four subunits in the NELF complex, best-known for its role in transcriptional pausing. Interestingly, in stark contrast to the other NELF subunits, Nelfa mRNA is detected at the highest levels in the oocyte and zygote, and shows a general decline thereafter, suggestive of a role in early development (FIG. 1g). Prompted by these observations, further investigation of the role of NELFA in greater detail was performed.

It was first confirmed by immunofluorescence that NELFA is a maternally supplied factor present in the mouse oocyte and early cleavage-staged embryos. In contrast, a lower expression is observed in the blastocysts, ratifying the similar decline that was observed in mRNA levels (FIG. 1c). Next, the expression of NELFA in mESCs, which are derived from the inner cell mass of blastocysts was examined. Strikingly, it was observed that NELFA is conspicuously absent (or lowly expressed) in the majority of mESCs, with the noteworthy exception of a small population of rare cells that exhibited high expression of NELFA (NELFA$^{high}$) (FIG. 1d). This surprising finding of NELFA heterogeneity was validated using 2 different antibodies against NELFA (Methods and Materials). Interestingly, NELFA$^{high}$ mESCs were depleted of Oct4 protein expression, unlike surrounding NELFA$^{low}$ cells (FIG. 1d). The property of heterogeneous expression also seemed to be specific only for NELFA and not for another key subunit of the NELF complex, NELFE (FIG. 1e). These observations suggest that NELFA, in this context, probably serves a function independent of its role in the NELF complex.

Example 2

Nelfa is Required for the Expression of 2C-Stage Specific Markers Such as Zscan4 and MERVL/HERVL Family of Retrotransposons To characterize this rare cell population, Nelfa$^{high}$ and Nelfa$^{low}$ cells were isolated for transcriptome analyses. The RNA-sequencing (RNA-seq) data revealed that 2155 genes are differentially expressed, the majority of which are upregulated in the Nelfa$^{high}$ cells. Strikingly, it was noticed that many of the pre-implantation embryo genes, especially those specific to the totipotent 2-cell (2C) stage embryo, were most highly induced. These included genes such as Zscan4, Tcstv3, Gm4340 as well as the endogenous retrovirus, MERVL. A comparison of the differentially expressed genes against all the 7 stages of pre-implantation embryo including ESCs, revealed a greater similarity of Nelfa$^{high}$ cells to the 2-cell embryo. The MERVL/HERVL family of retrotransposons belongs to a subclass of endogenous retrotransposons and its expression is tightly controlled during development. It is selectively expressed in the 2C embryo, and is typically silenced in ESCs, with the exception of a few rare cells (termed 2C-like ESCs). Comprehensive analysis of all the repetitive elements revealed that the MERVL family of retrotransposons (for example, mt2_mm, Mervl-_gag, Mervl-b4-int and Mervl-int) as well as major satellite repeats (gsat_mm) was most strongly activated. Next, co-expression of Zscan4 in Nelfa$^{high}$ ESCs was confirmed by immunostaining. Furthermore, using an independent Zscan4-Emerald reporter ESC line, the study showed that Nelfa was also readily detected in Zscan4-positive (Zscan4$^{Em+}$) cells. Taken together, the data shows that Nelfa$^{high}$ cells selectively upregulate a significant proportion of 2C-specific genes that are normally repressed in pluripotent ESCs.

On the basis of these findings, Nelfa$^{high}$ cells appear to resemble Zscan4-positive ESCs and/or the 2C-like ESCs. However, although Zscan4-positive and 2C-like ESCs express common markers such as the MERVL/HERVL family of retrotransposons, they may represent different phases in the developmental continuum and with distinct potency. In the present study, it was observed that whilst a majority of the Zscan4$^{Em+}$ cells are positive for Nelfa expression (72/90; 80%), Nelfa$^{high}$ ESCs tend to show a more restricted expression of Zscan4 (31/53; 58%). Furthermore, transcriptome analysis of Nelfa$^{high}$ ESCs and Zscan4$^{Em+}$ ESCs revealed that although the majority of the Zscan4$^{Em+}$-upregulated genes are co-expressed in Nelfa$^{high}$ ESCs, there remains a significant number of upregulated genes exclusive to Nelfa$^{high}$ ESCs. Importantly, in contrast to Zscan4 and the MERVL/HERVL family of retrotransposons, which are expressed exclusively in the 2-cell embryo, Nelfa is already present in the oocyte and 1-cell zygote. Considering these distinct expression profiles, the hypothesis that Nelfa may act upstream to promote the expression of the MERVL/HERVL family of retrotransposons and Zscan4 was considered. To test this hypothesis, Nelfa was first depleted in the Zscan4-reporter ESCs, and a pronounced reduction in the Zscan4-positive population was observed. This effect is specific to Nelfa since depletion of Nelfb or Nelfe had a negligible effect on Zscan4 expression. Next, a Doxcycline (Dox)-inducible Nelfa ESC line was generated. In the presence of DOX, Nelfa expression was strongly induced, and this was accompanied by the upregulation of Zscan4 as well as the MERVL family of retrotransposons. Taken together both the loss-of-function as well as gain-of-function experiments clearly demonstrate that Nelfa is necessary and sufficient for the expression of Zscan4 and the MERVL family of retrotransposons, and by extension, totipotency.

Example 3

Nelfa$^{high}$ mESCs Mark a 2C-Like State

Figure 2A:
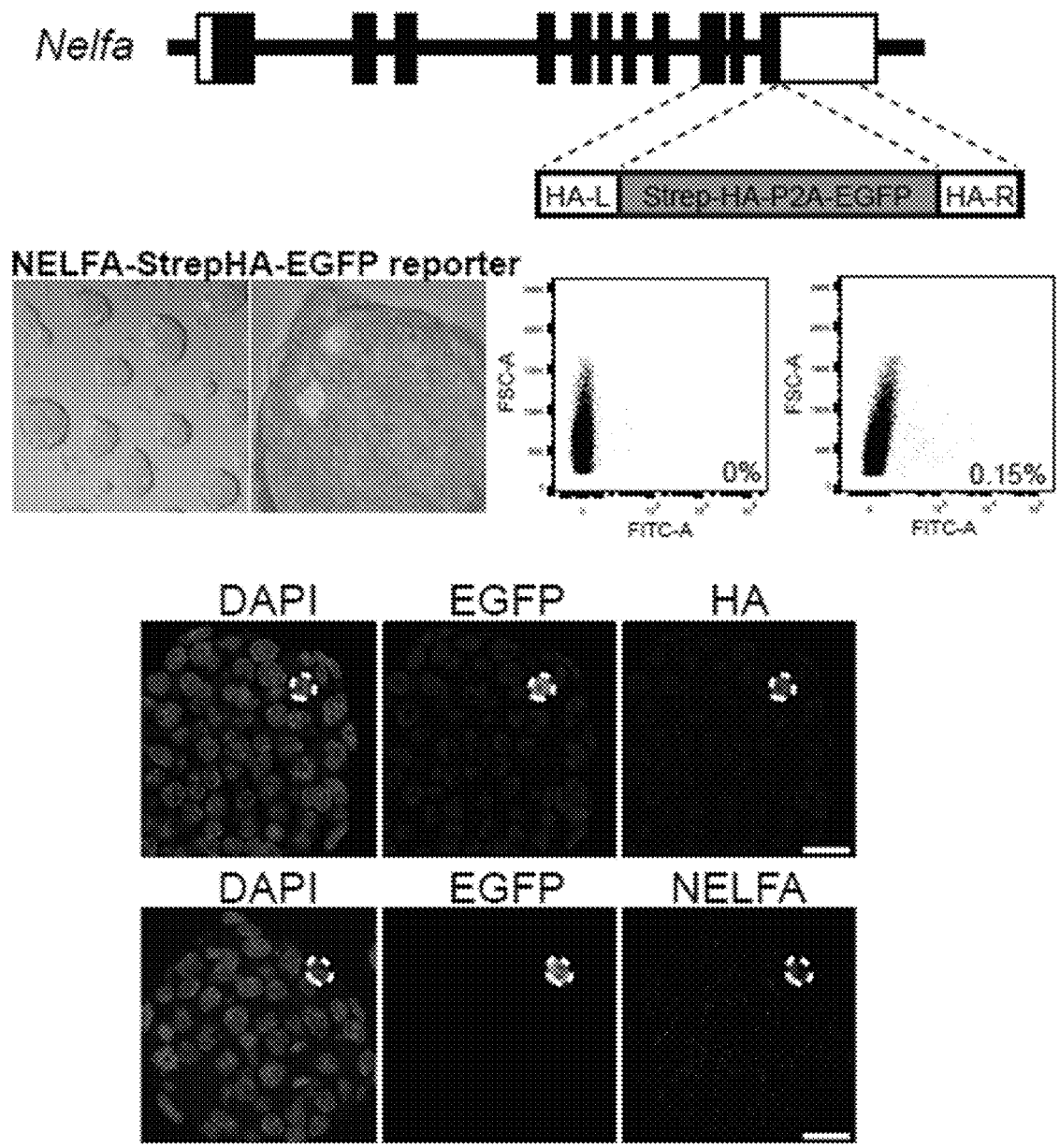
FIG. 2a is a set of microscopy images and diagram depicting the generation of a NELFA-Streptavidin-HA-P2A-EGFP reporter mESC line. A Streptavidin-HA-P2A-EGFP cassette flanked by homology arms (HA-L and HA-R) was inserted into the C-terminus of the mouse Nelfa locus. Reporter mESCs showed restricted expression of EGFP as determined by fluorescence microscopy and flow cytometry. Representative flow cytometry and immunofluorescence data are shown. Scale bar=20 µm.

To address if the NELFA$^{high}$ mESC subpopulation could correspond to a distinct ESC state, a NELFA reporter mESC line, in which a Strep-HA-P2A-EGFP cassette was inserted into the C-terminus of the Nelfa genomic locus (NELFA-Strep-HA-P2A-EGFP) was generated. Validations confirmed that this reporter line accurately recapitulated the heterogeneous expression of NELFA, and through flow cytometry it was determined that ~0.1-0.3% of mESCs expressed high levels of NELFA under conventional serum containing mESC culture condition (FIG. 2a).

Figure 2B:
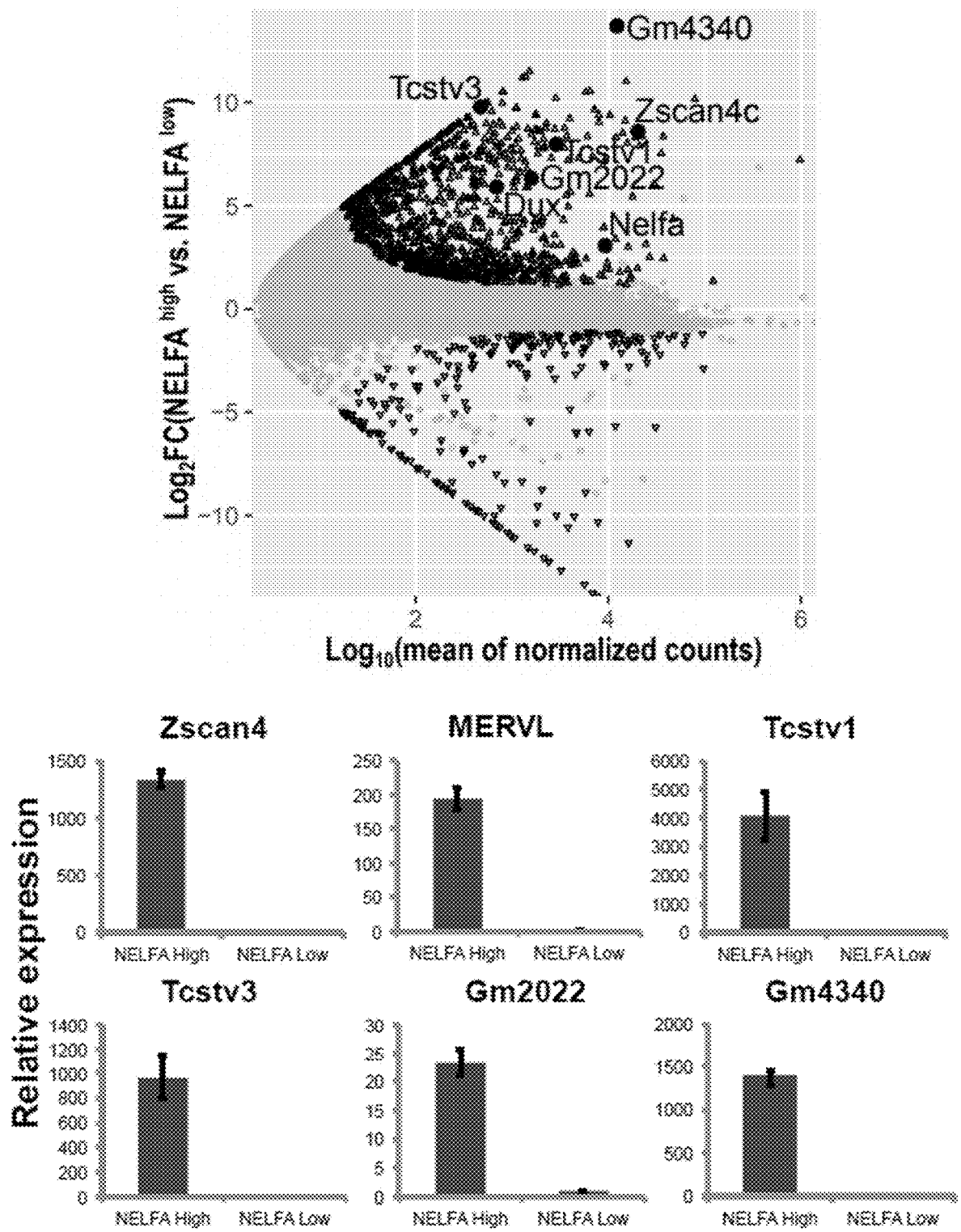
FIG. 2b is a set of bar graphs and MA plot showing changes in gene expression between NELFA$^{high}$ and NELFA$^{low}$ mESCs. Up and down-point triangles represent genes that are significantly up- and downregulated in NELFA$^{high}$ cells respectively (adjusted p-value≤0.01 and fold-change≥2). Selected 2C genes (filled black circles) are highlighted in the plot and validated by RT-qPCR. Error bars represent standard deviation of 3 replicates.
Figure 2C:
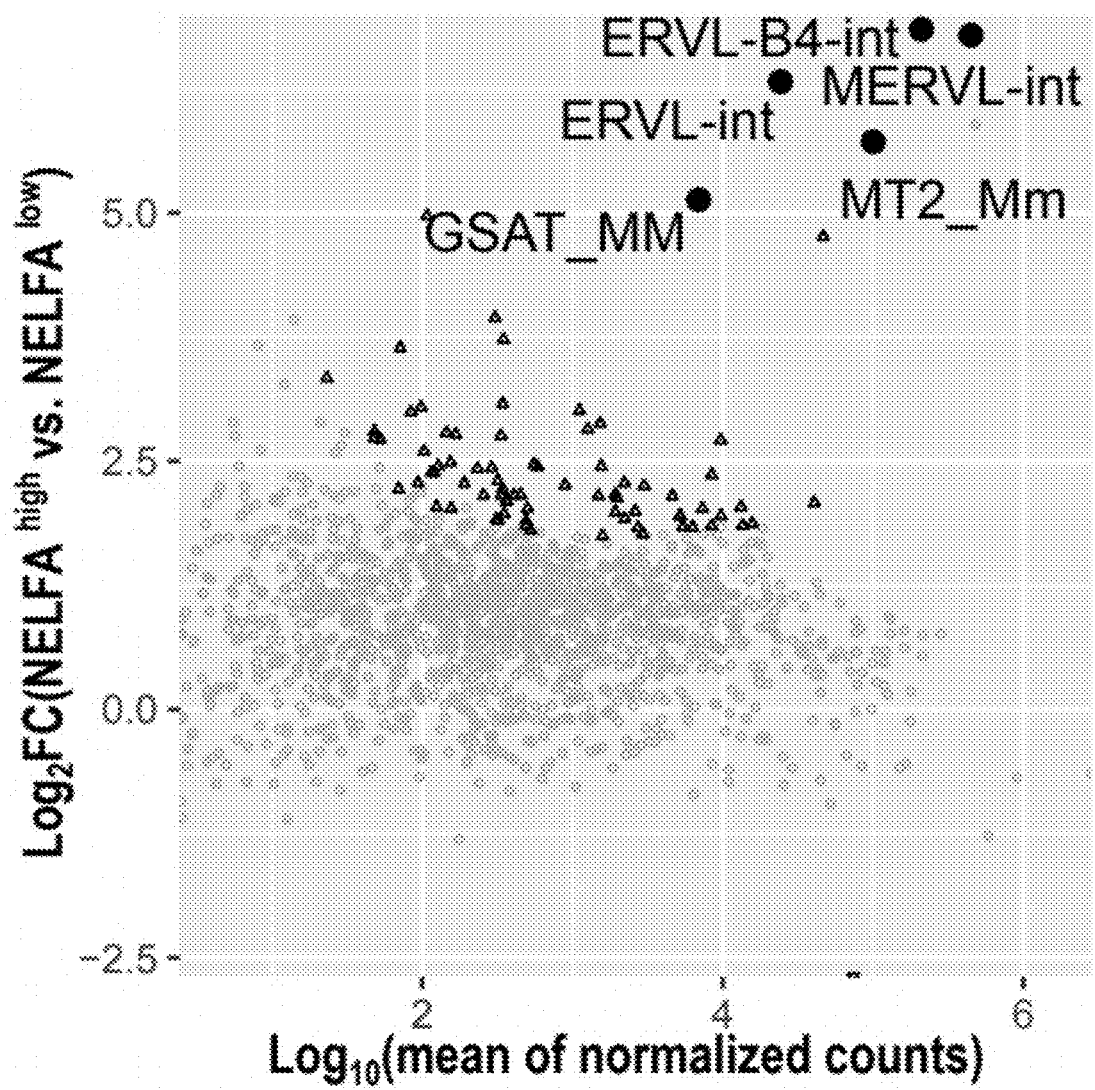
FIG. 2c is an MA plot showing changes in repetitive element expression between NELFA$^{high}$ and NELFA$^{low}$ mESCs. Up and down-point triangles represent repetitive elements that are significantly up- and downregulated in NELFA$^{high}$ cells respectively (adjusted p-value≤0.01 and fold-change≥2). Selected repetitive elements (filled black circles) known to be active in 2C-like cells are highlighted.
Figure 2D:
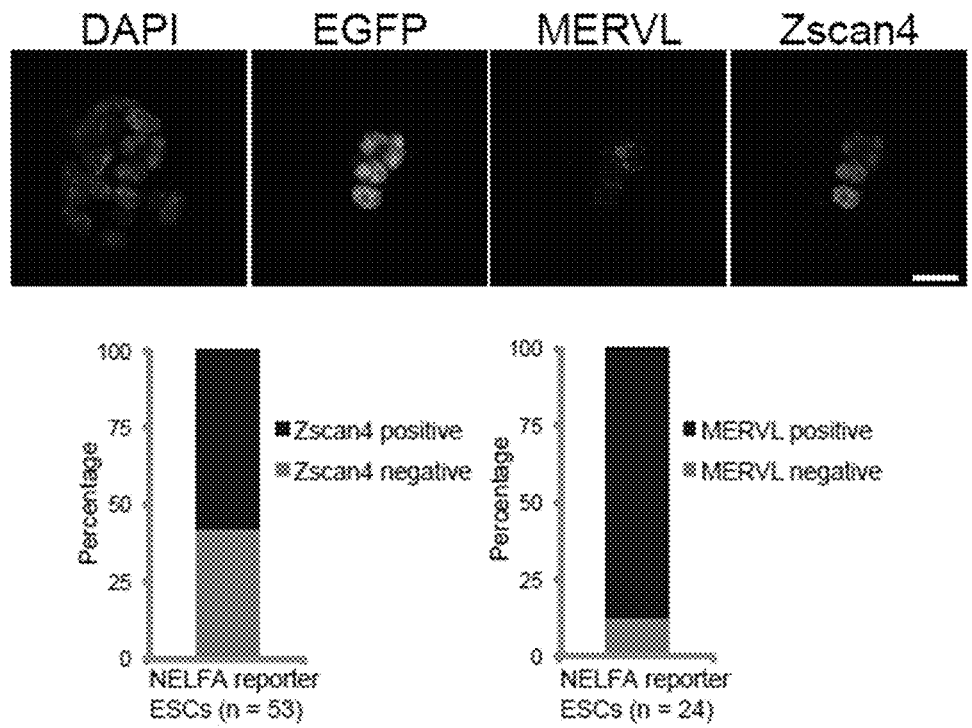
FIG. 2d is a set of microscopy images and bar graphs showing immunofluorescence for various 2C-like markers (as indicated) in NELFA-Strep-HA-P2A-EGFP and Zscan4-Emerald reporter mESC lines. Representative images are shown from 2 independent experiments. Quantification of expression of the markers in individual cells was performed based on the immunofluorescence data. Scale bar=20 µm.
Figure 2D:
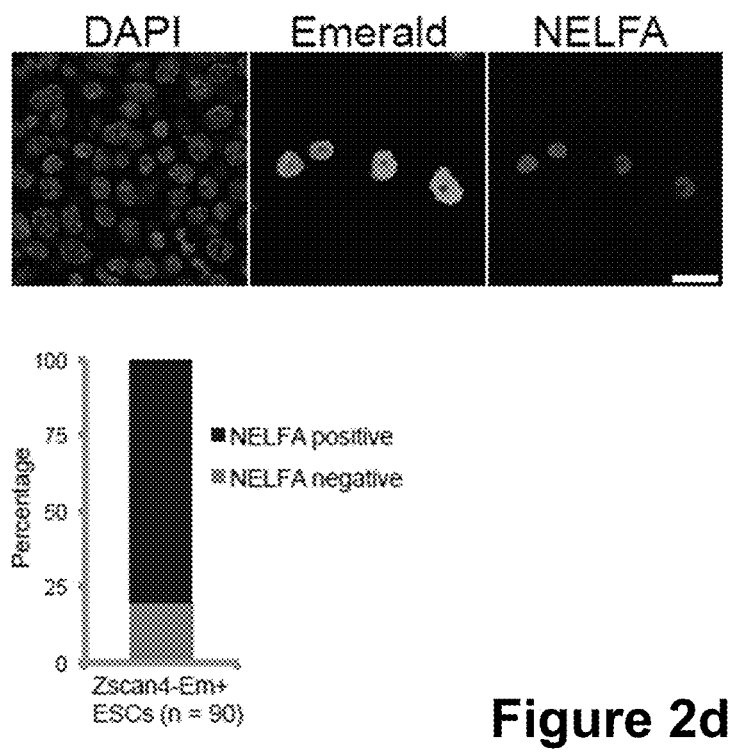

To characterize this rare cell population, NELFA$^{high}$ and NELFA$^{low}$ mESCs were isolated for transcriptome profiling by RNA-sequencing (RNA-seq) and 1335 differentially expressed genes were identified, of which the majority (1086 genes) were upregulated in the NELFA$^{high}$ cells. Notably, many of the pre-implantation embryonic genes that are specific to the totipotent 2C embryo were amongst the most highly induced. These included genes such as Zscan4, Tcstv3, Dux, Gm4340, MERVL, as well as other genes differentially expressed in NELFA$^{high}$ cells (FIG. 2b). The MERVL/HERVL family of retrotransposons belongs to a subclass of endogenous retrotransposons and its expression is tightly controlled during development. For example, it is selectively expressed in the 2C embryo, and typically silenced in later embryonic stages and ESCs. Comprehensive analysis of repetitive elements in the data revealed that the MERVL family of retrotransposons (such as mt2_mm, Mervl_gag, Mervl-b4-int and Mervl-int), as well as major satellite repeats (gsat_mm), were the most strongly activated (FIG. 2c). The upregulation of key transcripts was also confirmed by immunostaining, showing that Zscan4 and the MERVL family of retrotransposons were co-expressed in NELFA$^{high}$ mESCs. Interestingly, an independent Zscan4-Emerald (Zscan4-Em) reporter mESC line was used and it was observed that high NELFA expression was readily detected in Zscan4-positive cells (FIG. 2d). The correlated expression of both Zscan4 and NELFA strongly suggests that NELFA might also be implicated in regulating the emergence of 2C-like state in mESCs.

Figure 2E:
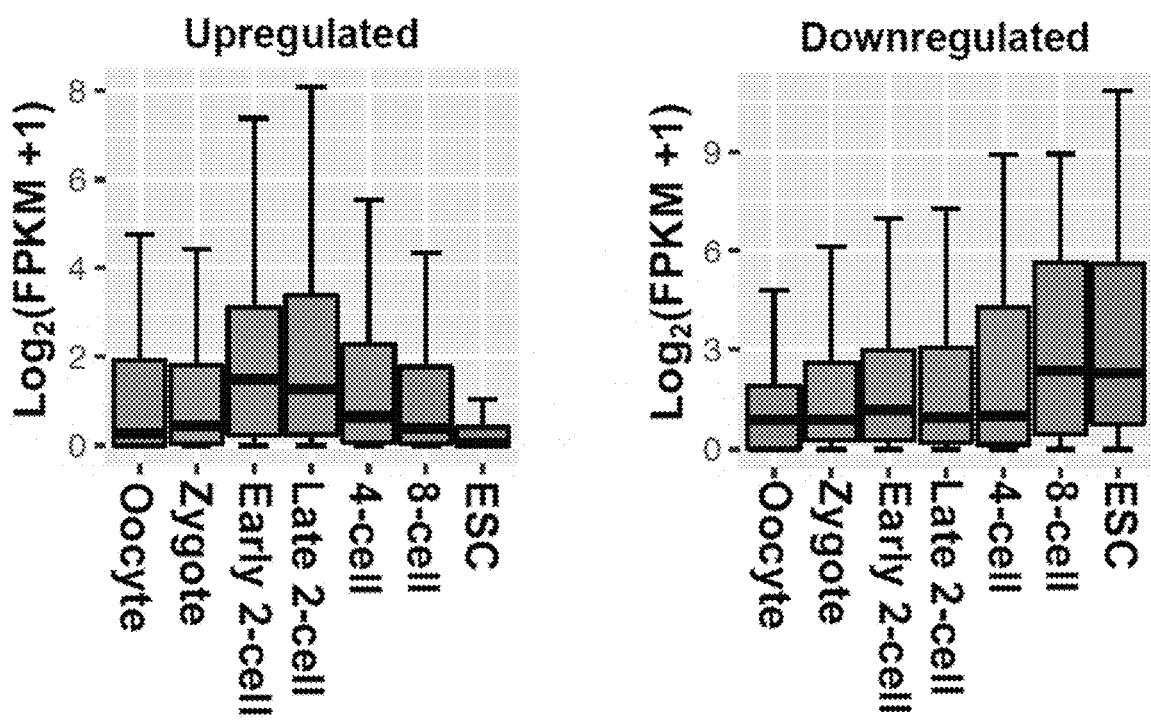
FIG. 2e is a pair of box plots showing that NELFA$^{high}$-upregulated genes are most highly expressed in 2C-stage embryos (left panel), whereas NELFA$^{high}$-downregulated genes tend to be expressed at later stages of pre-implantation development and in mESCs (right panel).
Figure 2F:
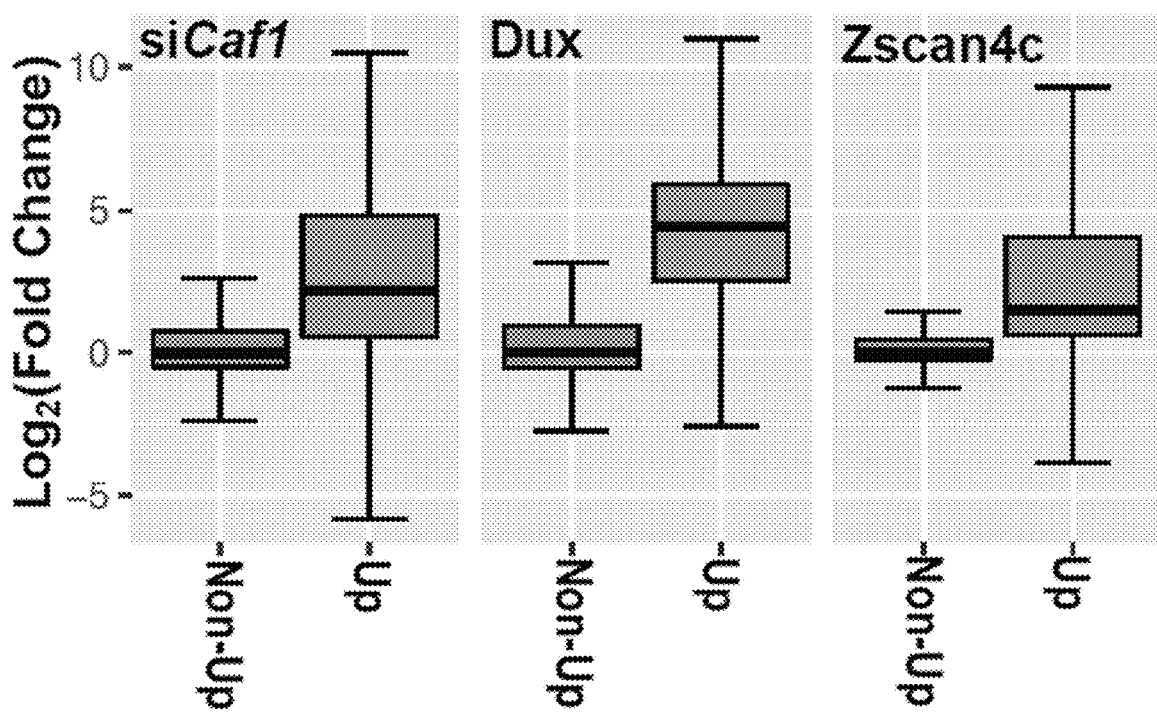

Critically, the comparisons of NELFA$^{high}$-upregulated genes against the 7 embryonic transcriptome stages (FIG. 1a) revealed that these genes were most highly expressed in the 2C stage. Conversely, genes that are downregulated in NELFA$^{high}$ mESCs represented genes that were highly expressed at later stages of embryonic development and in mESCs (FIG. 2e). These observations thus suggest that NELFA$^{high}$ mESCs might represent a 2C-like cellular state. Furthermore, the downregulation of mESC-specific genes in NELFA$^{high}$ cells indicates that the activation of the 2C gene program may require active suppression of naïve pluripotency. In support of this, the earlier immunostaining of NELFA$^{high}$ mESCs showed a lack of Oct4 protein expression (FIG. 1d). To further validate the 2C-like features of NELFA$^{high}$ mESCs, it was asked if the NELFA$^{high}$-upregulated genes were also highly expressed in previously reported 2C-like cells, and indeed a strong positive correlation was observed (FIG. 2f). Taken together, it is concluded that NELFA$^{high}$ mESCs selectively activate 2C-specific genes that are normally repressed in the pluripotent state.

Example 4

Nelfa is a Novel Driver of the 2C-Like State in mESCs

On the basis of these findings, NELFA$^{high}$ cells appear to resemble erstwhile-reported Zscan4-positive and the MERVL family of retrotransposon-positive 2C-like mESCs. However, it is very plausible that the expression of these markers may represent different phases along the pluripotent to totipotent/2C-like continuum. Here, it was noticed that whilst the majority of the Zscan4$^{Em+}$ mESCs are positive for NELFA expression, NELFA$^{high}$ mESCs tend to show a more restricted co-expression of Zscan4 (FIG. 2d). Additionally, NELFA is expressed during the earliest stages of in vivo development, in both the oocyte and zygote (FIG. 1c), in contrast to Zscan4 and the MERVL/HERVL family of retrotransposons, which are only expressed exclusively in the 2C embryo.

Figure 3A:
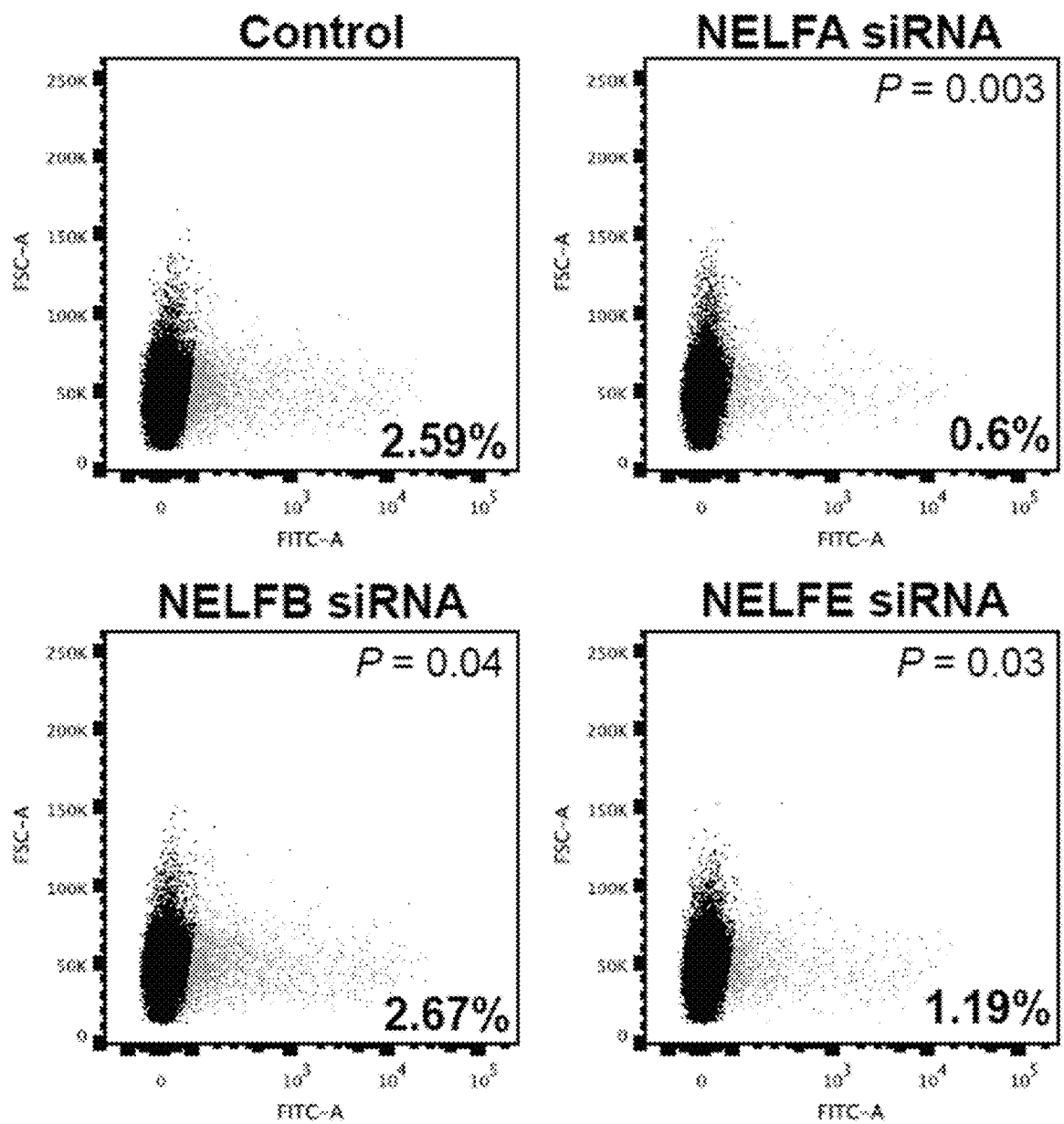
FIG. 3a is a set of plots and bar graphs depicting the result of flow cytometry analysis of Zscan4-Emerald mESCs after siRNA knockdown of individual NELF complex subunits illustrated that NELFA depletion gave rise to a distinct decrease in the Zscan4-marked 2C-like population. Representative data from 4 independent experiments is shown here. P value determined by paired two-sided Student's T-test. Efficiency of knockdowns was assessed by RT-qPCR. Error bars represent the standard deviation of 3 technical replicates.
Figure 3A:
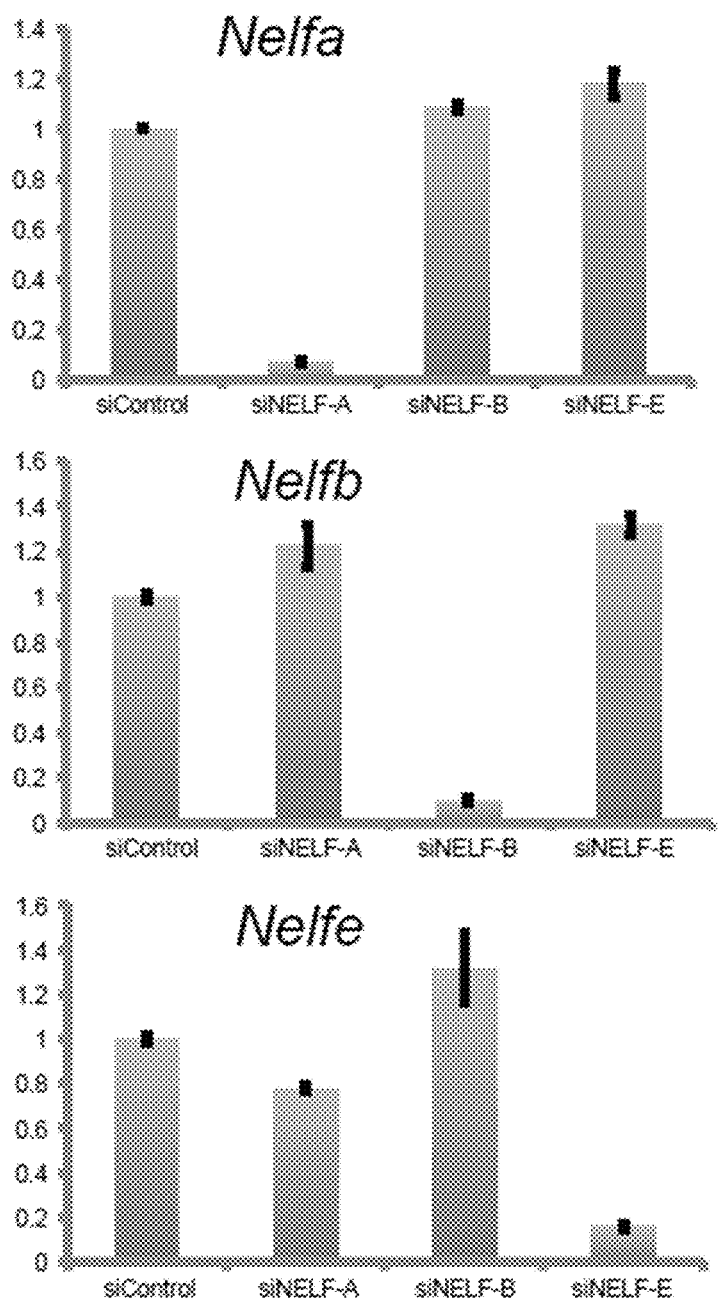
Figure 3B:
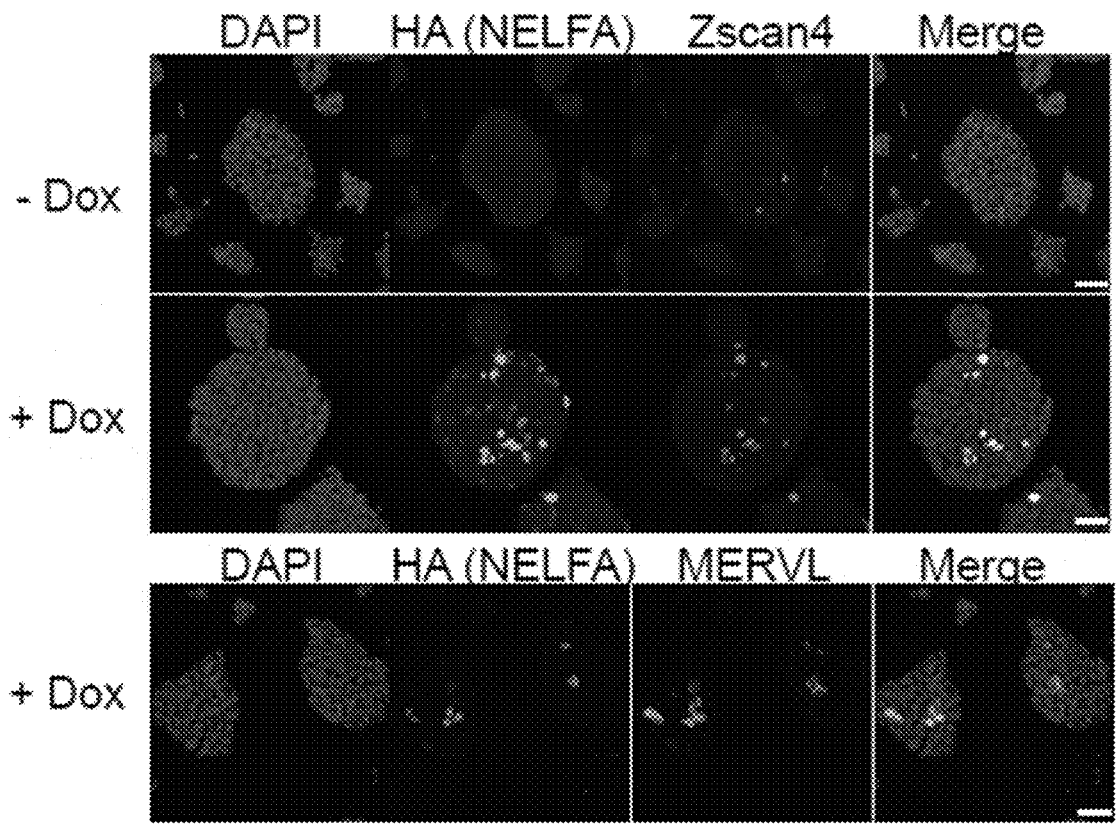
FIG. 3b is a set of microscopy images and a pair of bar graphs depicting immunofluorescence result for various 2C-like markers (as indicated) in Dox-inducible NELFA-Strep-HA-P2A-EGFP mESCs. Representative images are shown from 3 independent experiments. Quantification of expression of the markers in individual cells was performed based on the immunofluorescence data. Scale bar=40 µm.
Figure 3B:
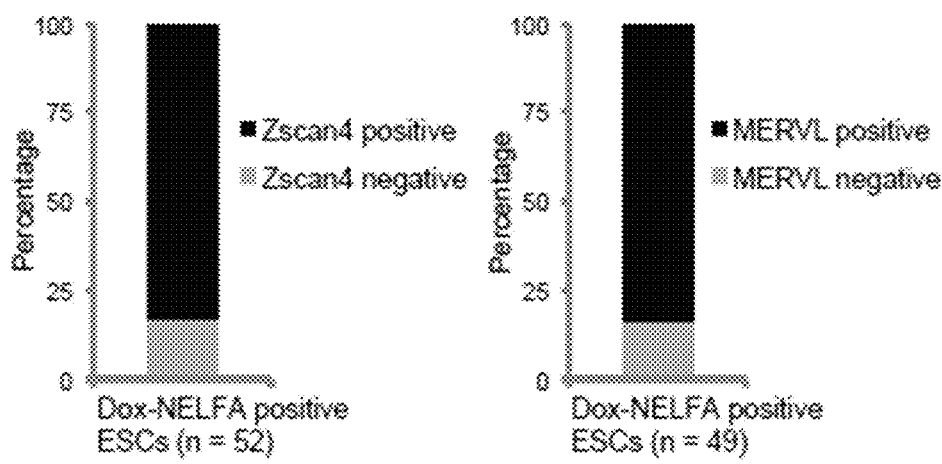

Considering these temporally distinct expression profiles, it was hypothesized that NELFA might act upstream of the MERVL/HERVL family of retrotransposons and Zscan4 to promote their expression. To test this hypothesis, NELFA in Zscan4-Em reporter mESCs was first depleted, and a pronounced reduction in the Zscan4$^{Em+}$ population (FIG. 3a) was observed. Importantly, this phenomenon was specific to NELFA, since the abrogation of two other NELF complex subunits NELFB and NELFE showed modest effect on Zscan4$^{Em+}$ (FIG. 3a). Next, a Doxcycline (Dox)-inducible NELFA-overexpressing mESC line (pTRE-NELFA-Strep-HA) was generated. In the presence of Dox, NELFA expression was strongly induced as expected and this was accompanied by the robust upregulation of Zscan4 and the MERVL family of retrotransposons (FIG. 3b). Taken together, both loss- and gain-of-function experiments clearly demonstrate that NELFA is necessary and sufficient for downstream expression of Zscan4 and the MERVL family of retrotransposons.

Figure 3C:
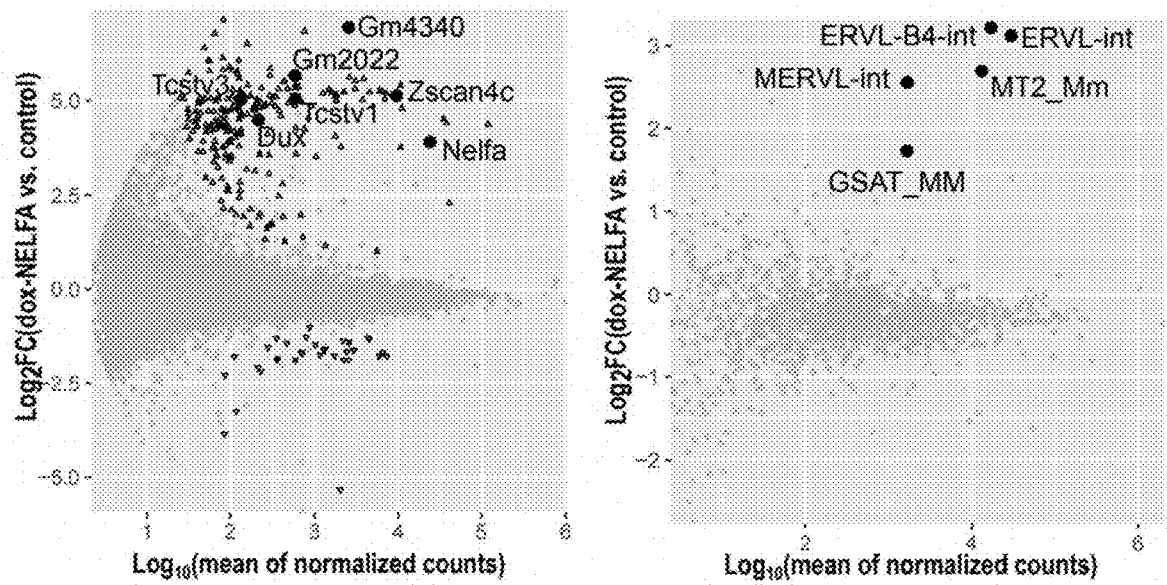
FIG. 3c is a pair of MA plots showing expression changes in genes (left) and repetitive elements (right) between NELFA-induced 2C-like cells and control mESCs (adjusted p-value≤0.01 and fold-change≥2). Up and down point-triangles represent genes and repetitive elements that are significantly up- and downregulated respectively. Selected 2C genes and repetitive elements are denoted by filled black circles.
Figure 3D:
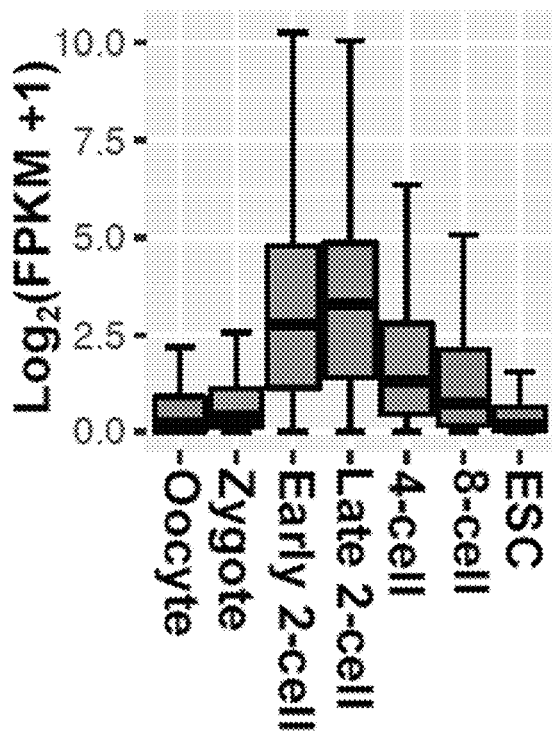
FIG. 3d is a box plot showing that the genes upregulated in NELFA-induced 2C-like cells are enriched for expression at the 2C stage during pre-implantation development.
Figure 3F:
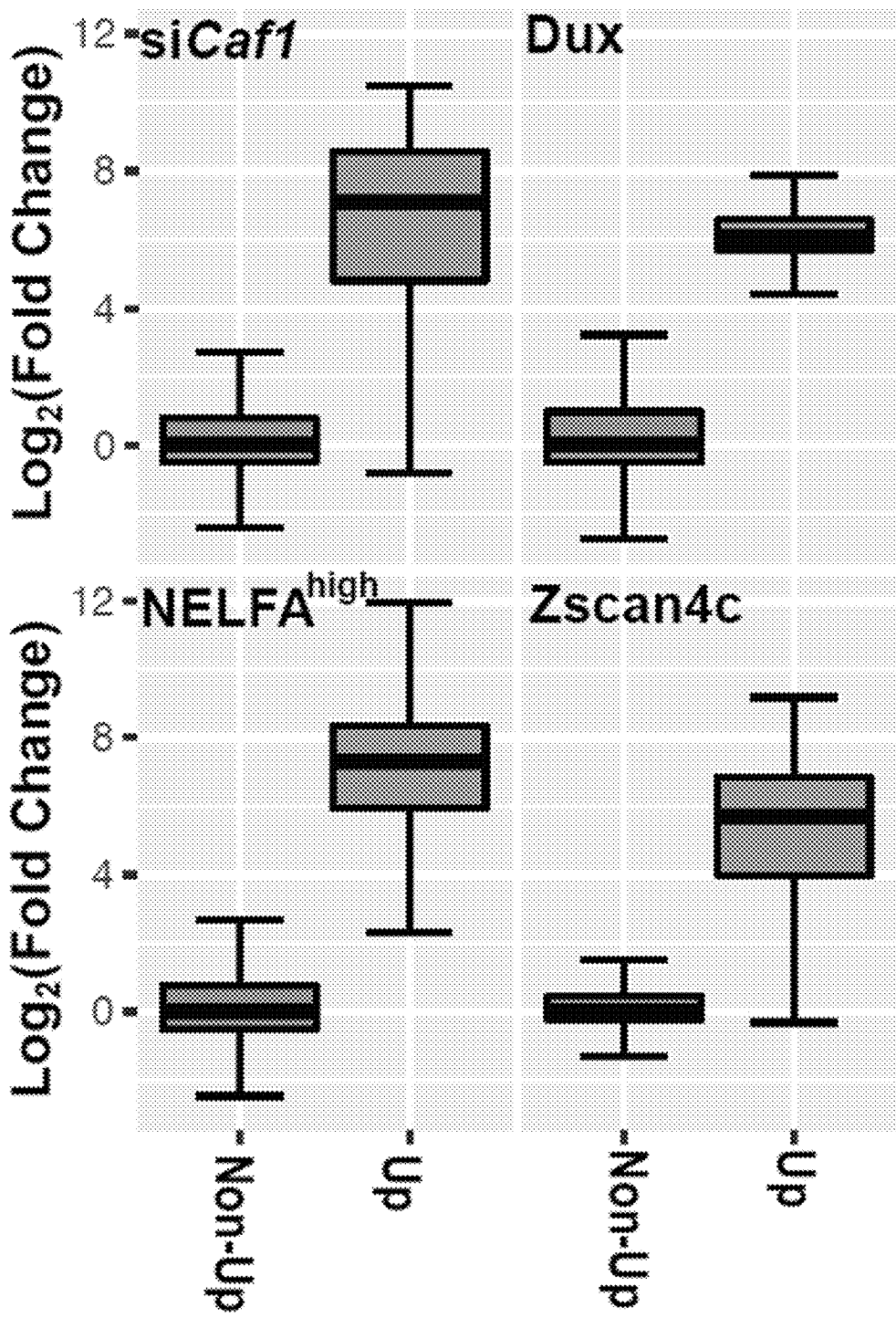
FIG. 3f is a set of boxplots depicting the relative expressions of NELFA-induced genes (Up) and the rest (Non-Up) in 2C-like cells induced by CAF1 inhibition (upper left panel), over-expression of Dux (upper right panel), NELFA$^{high}$ (bottom-left panel) and Zscan4-positive ESCs (bottom-right panel) respectively. NELF-A induced genes (n=229) are specifically upregulated in 2C-like mESC transcriptomes. Center line: median; box limits: lower and upper quartiles; upper whisker: the smaller value of the maximum value and upper quantile plus 1.5× the interquartile range; lower whisker: the larger value of the minimum value and the lower quantile minus 1.5× the interquartile range.

To capture the transcriptomic changes following NELFA induction, another Dox-inducible NELFA-EGFP mESC line was generated. These cells were Dox-induced for 16 hours and NELFA-EGFP-positive cells were purified by FACS, then subjected to RNA-seq. Remarkably with this relatively short duration of induction, robust upregulation of several key 2C markers including the endogenous retroviruses could be observed (FIG. 3c). It was surmised that this group of genes (n=229; log$_2$FC≥1 and adjusted p-value≤0.01) might encompass some of the key early effectors of the 2C state, and noted that Dux, one of the earliest known drivers of the 2C state, was upregulated upon NELFA induction. These 229 upregulated genes are most highly expressed at early- and late-2C stages relative to all other developmental stages (FIG. 3d), and are similarly upregulated in all other 2C-like reporter mESCs (FIG. 3f). It was thus concluded that NELFA's expression is not merely a reporter, but also a novel driver of the 2C-like state. The 229 upregulated genes might likewise exert a similar function to Nelfa.

Figure 3G:
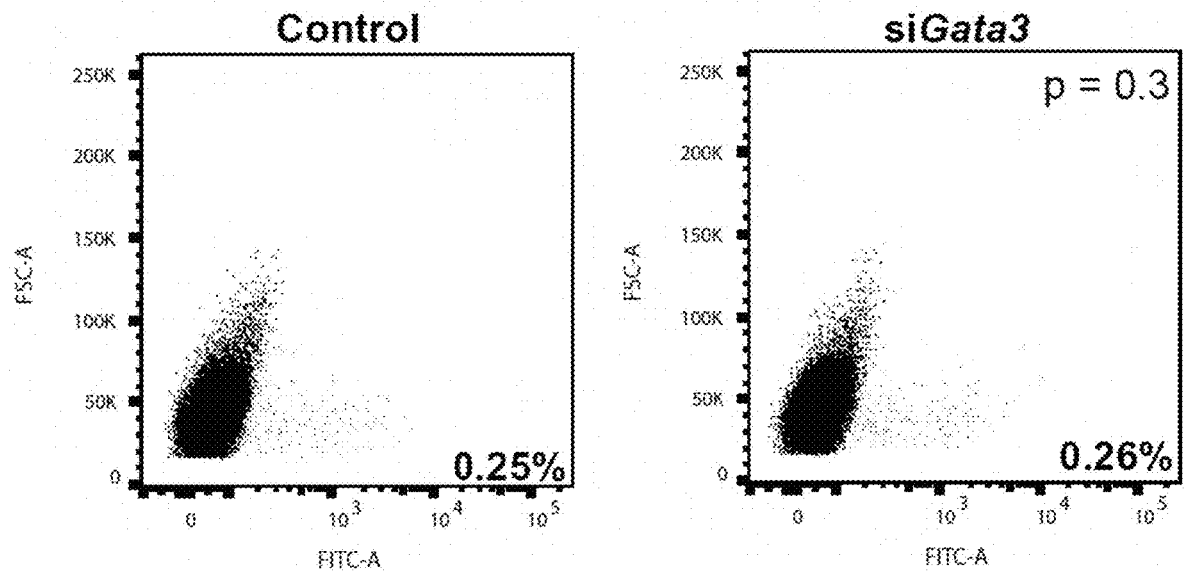
FIG. 3g is a pair of plots depicting result of flow cytometry analysis of NELFA-StrepHA-P2A-EGFP mESCs after siRNA knockdown of Gata3. Representative data from 2 independent experiments is shown here. P value determined by paired two-sided Student's T-test.
Figure 3H:
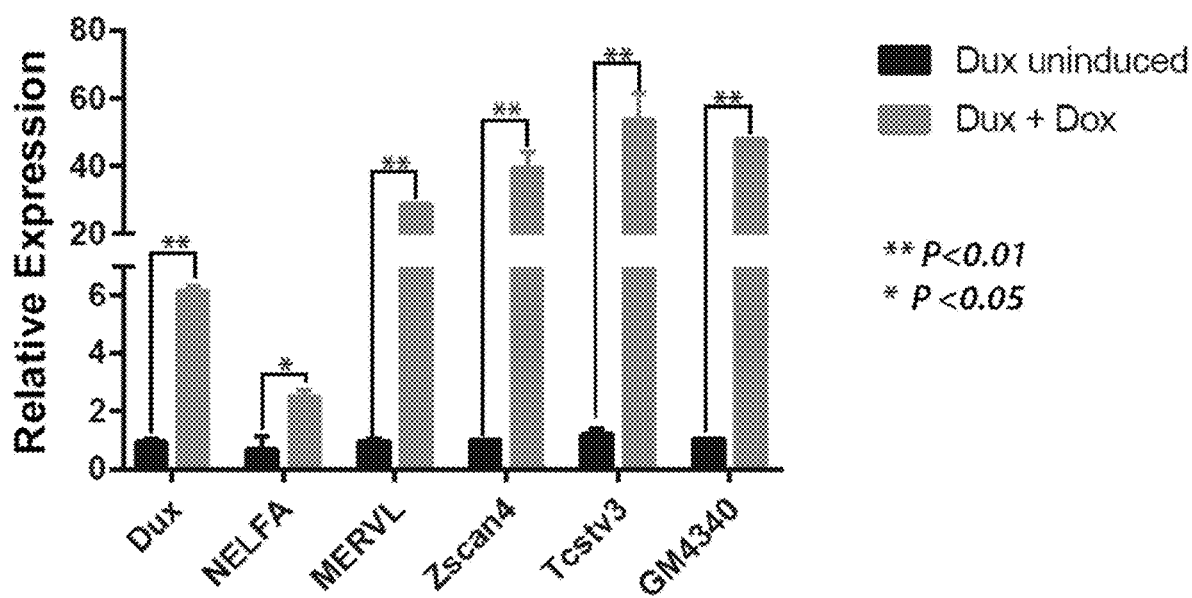
FIG. 3h is a bar graph showing expression levels of various 2C genes, upon Dux overexpression, by RT-qPCR. Error bars represent the standard deviation of 3 independent experiments. Indicated comparisons were done using paired two-sided Student's T-tests. Thus.

Attempting to elucidate transcriptional events occurring during fate transition to the 2C-like state, promoter motif enrichment analysis was performed on the 229 Dox-induced genes and it was discovered that two transcription factor motifs, DUX and GATA3, were over-represented in the promoters of these early-upregulated genes. In good agreement, both motifs were also enriched at promoters of upregulated genes in NELFA$^{high}$ reporter mESCs (FIG. 3e). It is noted that this finding corroborates recent studies identifying DUX as a key regulator of cleavage-stage gene expression, and notably, the re-analysis of a published mESC Dux ChIP-seq dataset recovered both DUX and GATA3 motifs enriched at Dux binding sites. Closer inspection of the two motifs showed an intriguing resemblance between them (FIG. 3e). However, based on our RNA-seq (FIG. 3c), only Dux, but not Gata3, is upregulated in NELFA-induced mESCs. Furthermore, the knockdown of Gata3 did not affect the proportion of NELFA$^{high}$ cells (FIG. 3g), the observation was focused on the relationship between NELFA and Dux. Interestingly, while the induction of NELFA expression led to Dux upregulation (FIG. 2b), the induction of Dux also promoted the expression of NELFA, along with other 2C-genes (FIG. 3h). These data, along with the expression profiles of NELFA and Dux in early embryogenesis, suggest that whilst NELFA may prime the expression of Dux, both factors once expressed, act in an auto-regulatory fashion to ensure robust induction of the 2C-gene expression program.

Example 5

To gain further mechanistic insight into how Nelfa induces the totipotent-like state, gene ontology (GO) and KEGG pathway analyses were performed on the differentially expressed genes between Nelfa$^{high}$ and Nelfa$^{low}$ cells. Nucleosome assembly was uncovered as one of the most significantly downregulated pathways. Interestingly, histone gene expression appeared to be negatively affected in Nelfa$^{high}$ ESCs. Importantly, re-examination of two independent Zscan4 ESC transcriptome datasets also revealed a similar finding. The findings thus suggest that attenuated histone gene expression coupled to NAP1 nuclear localization may collectively contribute to an overall more decompacted chromatin in Nelfa$^{high}$ ESCs.

Further to the widespread changes in chromatin structure, KEGG pathway analysis revealed a striking suppression of numerous metabolic pathways such as oxidative phosphorylation and glycolysis in the Nelfa$^{high}$ ESCs, suggesting that Nelfa$^{high}$ cells may be metabolically inactive, at least transiently. Notably, early studies have established that early pre-implantation embryos including the totipotent 2C embryos as well as PGCs are metabolically less active, with lower oxygen consumption and ATP generation compared to blastocysts and ESCs. In particular, early cleavage-stage embryos must actively suppress glycolysis and utilize pyruvate instead of glucose as their major energy source. Importantly, a deliberate blockage of glycolysis is requisite for the development of the totipotent embryo. Therefore, the study assessed if pharmacological suppression of glycolysis may promote the emergence of Nelfa$^{high}$ ESCs in vitro. In excellent agreement, it was observed that addition of the glucose analog, 2-deoxy-D-glucose (2-DG), an inhibitor of glucose transport and glycolytic ATP production, led to a prominent increase in Nelfa$^{high}$ ESC subpopulation. Importantly, the reactivation of Nelfa was once again coupled to nuclear NAP1 localization and loss of chromocenters. Transcriptome profiling of the unsorted 2-DG-treated Nelfa reporter ESCs further confirmed the upregulation of several 2C genes. Taken together, the data suggests that metabolic reprogramming of Nelfa$^{high}$ cells is associated with extensive chromatin remodelling that correlates with the acquisition of an early embryonic gene signature.

A suppressed glycolytic state thus represents a molecular feature of totipotency that can be manipulated to drive ESCs into the totipotent lineage. To gain a deeper understanding, the study sought to identify the key regulators that potentially control glycolysis. For this, iRegulon, a computational method that detects TF-binding motifs and their target interactions was employed. From the KEGG database, a list of genes that are involved in glycolysis was obtained and queried against iRegulon. The analysis revealed several potential transcription factors (Hif1a, Pou5f1, Gata2, Myna, Sirt1, Serra and Erg) that may be involved in regulating the expression of the glycolytic enzymes. Notably, the majority of these factors are downregulated in Nelfa$^{high}$ ESCs, which may account for the subdued glycolysis.

Example 6

Figure 4A:
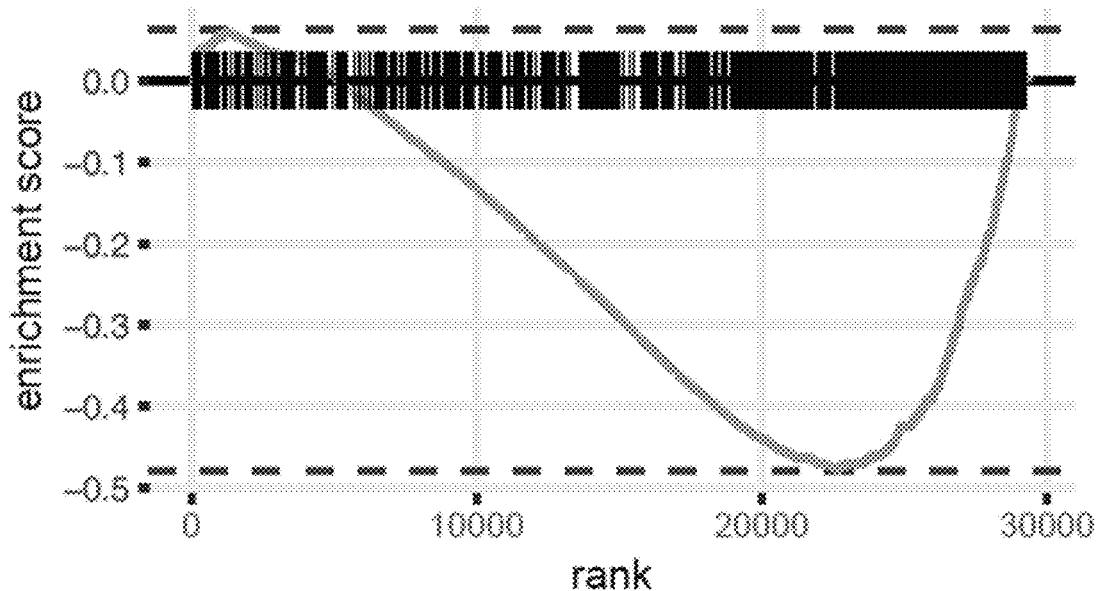
FIG. 4a shows a pair of enrichment plots for Metabolic pathways (mmu01100) for NELFA-reporter and Dox-NELFA mESCs.
Figure 4A:
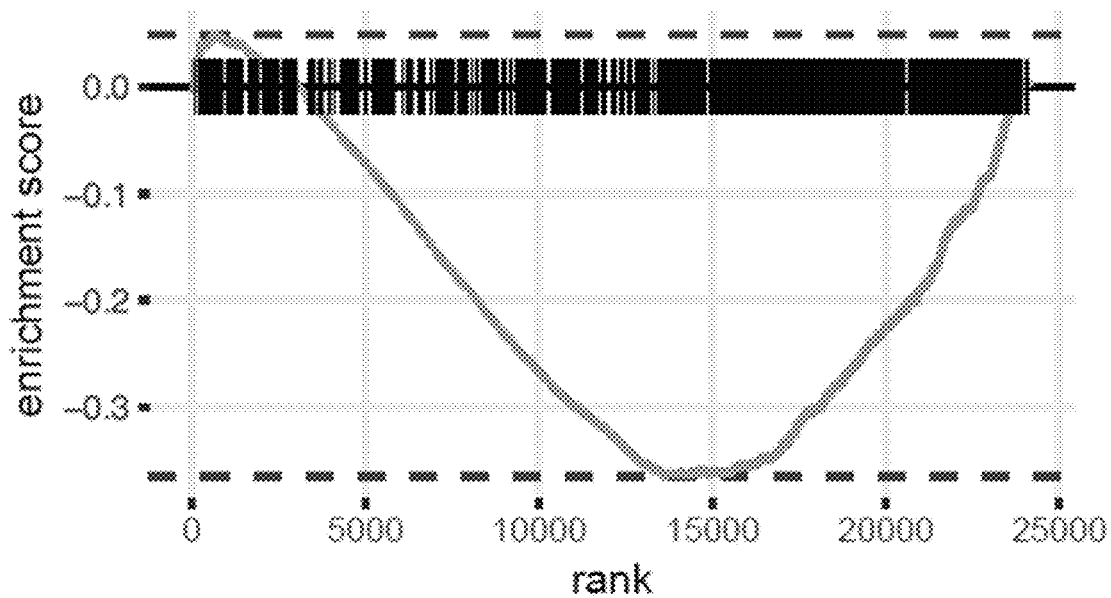
Figure 4B:
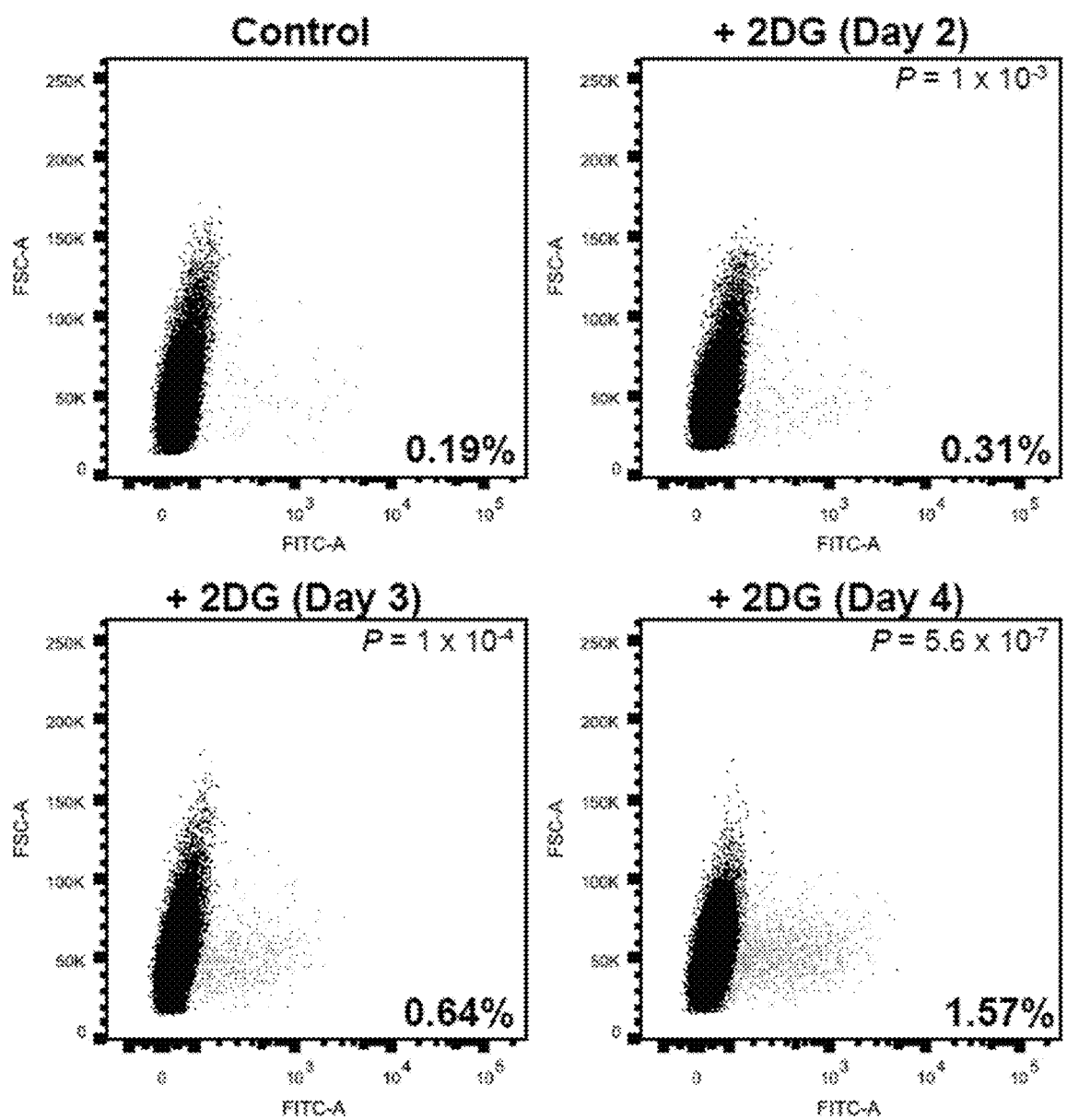
FIG. 4b shows a set of plots depicting the result of flow cytometry analysis of NELFA-Strep-HA-P2A-EGFP mESCs following 2-DG (4 mM) treatment for four days. Representative data from 7 independent experiments is shown here. P value determined by paired two-sided Student's T-test.
Figure 4C:
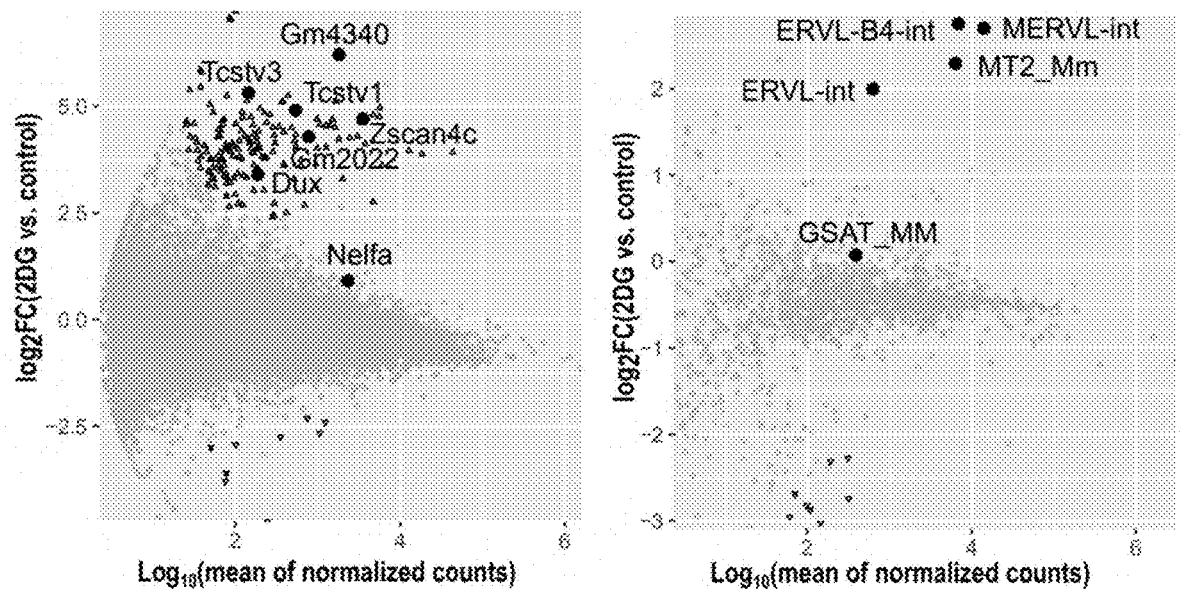
FIG. 4c is a pair of MA plots showing expression changes in genes (left) and repetitive elements (right) in NELFA reporter mESCs after 2-DG treatment (adjusted p-value≤0.01 and fold-change≥2). Up and down-point triangles represent up- and downregulated genes and repetitive elements respectively. Selected 2C genes and repetitive elements are denoted by filled black circles.
Figure 4D:
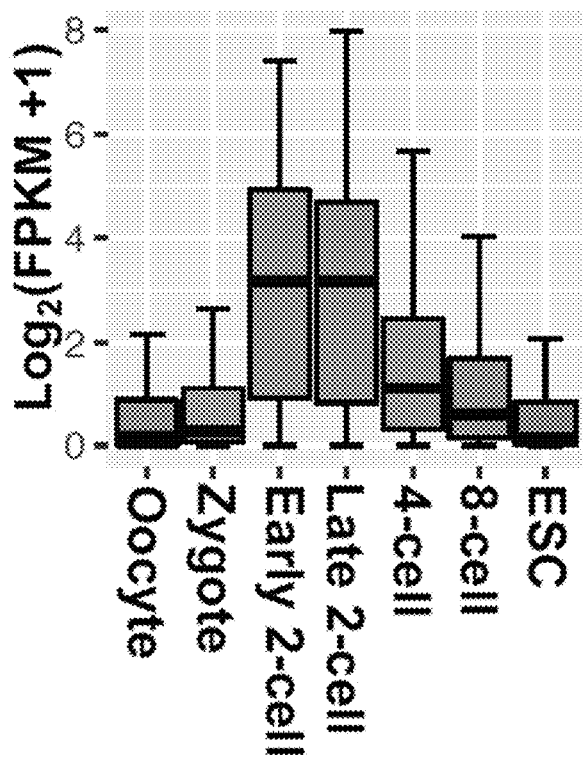
FIG. 4d is a box plot showing that upregulated genes in NELFA reporter mESCs after 2-DG drug treatment are most highly expressed in 2C-stage embryos during early pre-implantation development.
Figure 4E:
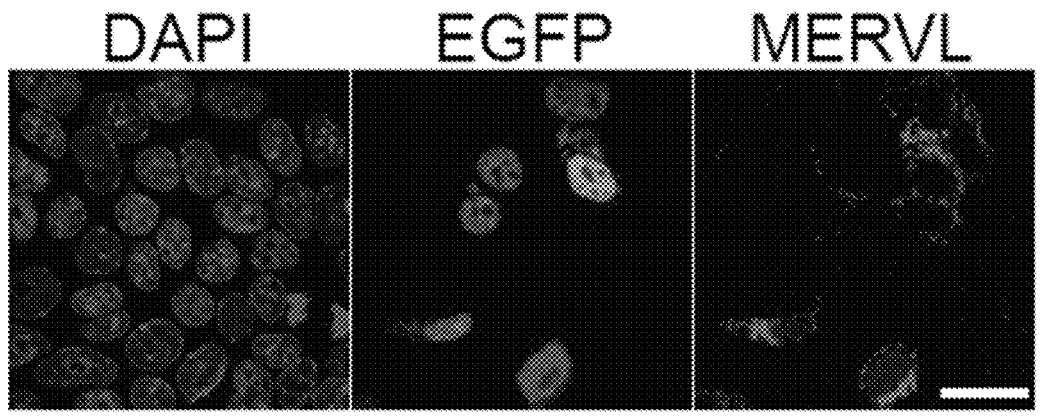
FIG. 4e is a set of microscopy images and a pair of bar graphs depicting immunofluorescence for EGFP (NELFA), MERVL and Zscan4 in NELFA reporter mESCs treated with 2-DG. Quantification of the number of NELFA positive cells co-expressing Zscan4 or MERVL was performed based on immunofluorescence data. 2 independent experiments were performed. Scale bar=20 µm.
Figure 4E:
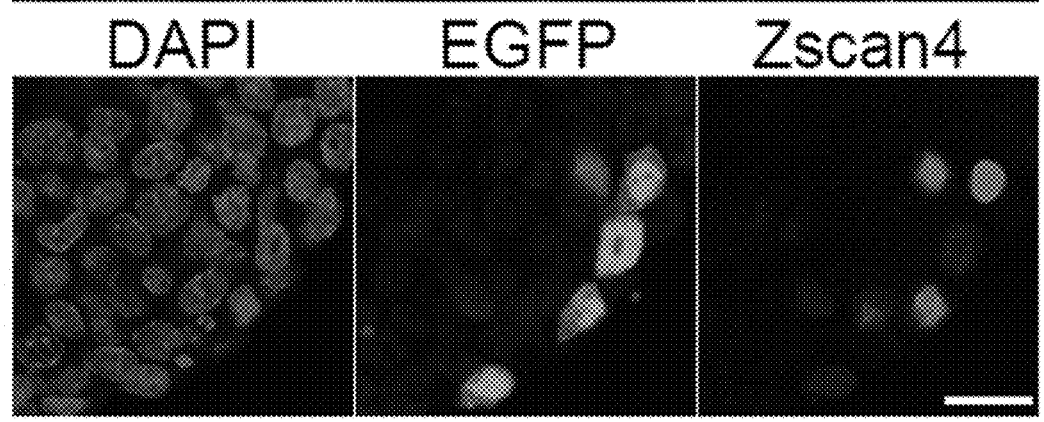
Figure 4E:
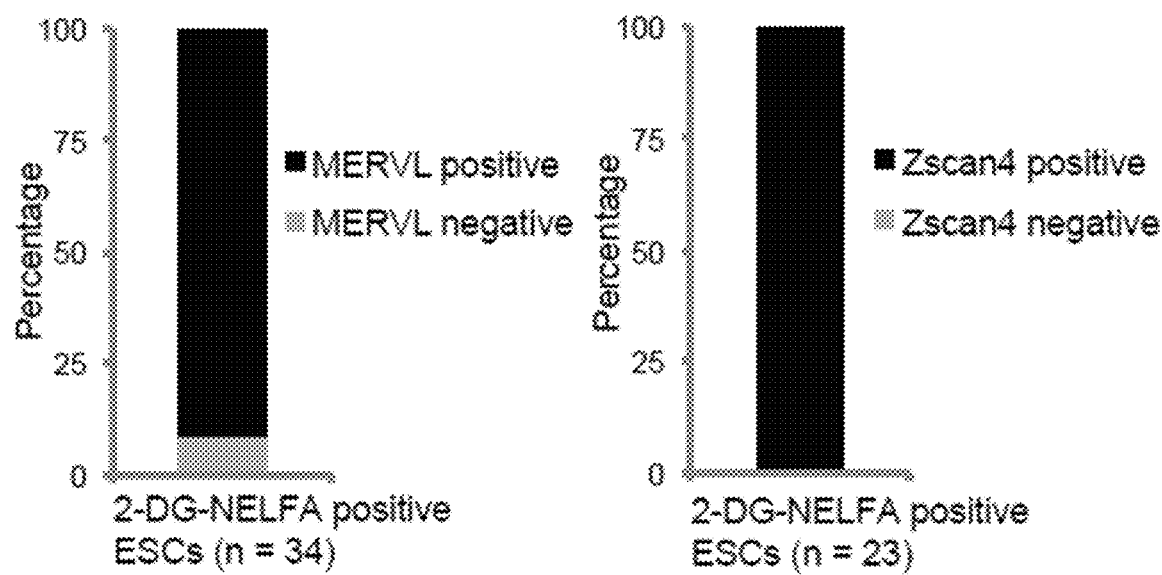

Suppression of Glycolysis by 2-DG Induces the 2C-Transcriptional Program in a NELFA-Dependent Manner In order to uncover the biological processes that might be affected by NELFA induction, gene set enrichment analysis (GSEA) against the KEGG database for NELFA$^{high}$ and Dox-induced NELFA cells was performed. Unexpectedly, metabolism (metabolic pathways; mmu01100) emerged as one of the most significantly altered processes in both cell types (NELFA$^{high}$ cells: Normalized enrichment score, NES=−2.24, adjusted p-value=0.001; Dox-NELFA-EGFP cells: NES=−1.41, adjusted p-value=0.001) (FIG. 4a and Table 4). In particular, specific metabolic pathways such as glycolysis and oxidative phosphorylation were inhibited to varying extents (FIG. 4g), suggesting that NELFA-expressing mESCs are metabolically less active compared to their NELFA-negative counterparts. Significantly, the equivalent analysis of a published Zscan4-Em mESC transcriptome dataset convened to a similar conclusion (FIG. 4g). Taken together, the results suggest that NELFA$^{high}$ mESCs may reside in a state of relative metabolic inactivity.

TABLE 4

List of enriched genes

| | Description | setSize | enrichmentScore | NES | pvalue | p. adjust | qvalues | rank | leading_edge | core_enrichment |
|---|---|---|---|---|---|---|---|---|---|---|
| mmu00970 | Aminoacyl-tRNA biosynthesis | 44 | −0.587 | −1.73 | 0.000167 | 0.005195 | 0.00371 | 7734 | tags = 86%, list = 37%, signal = 55% | Dars2/Vars2/Gatb/ Wars2/Qrsl1/Tars2/ Kars/Aars/Farsa/ Sars2/Cars2/Nars2/ Dars/Mars2/Vars/ Qars/Ears2/Iars2/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| mmu04152 | AMPK signaling pathway | 116 | −0.458 | −1.56 | 0.000552 | 0.008739 | 0.006241 | 6971 | tags = 52%, list = 33%, signal = 35% | Mars/Aars2/Wars/ Rars/Pstk/Farsb/ Sepsecs/Hars2/Gars/ Lars2/Yars/Yars2/ Sars/Nars/Eprs/ Tars/Cars/Rars2/Lars Rab8a/Akt1/Ppp2r1b/ Rps6kb2/Pfkm/Ppp2r5b/ Hnf4a/Akt1s1/Scd2/ Ccna2/Pik3cb/Pik3ca/ Creb3l1/Strada/Tsc1/ Pdpk1/Pik3cd/Ppp2r5a/ Tbc1d1/Akt2/Adipor2/ Pfkfb3/Ppp2r5e/ Prkab2/Pik3r2/Rheb/ Acaca/Prkaa1/Prkag1/ Ppp2ca/Eif4ebp1/ Map3k7/Ppp2cb/ Hmgcr/Ppp2r3c/ Camkk2/Cpt1b/Eef2k/ Prkab1/Pfkfb2/ Cab39l/Elavl1/ Pfkl/Rab10/Rab2a/ Sirt1/Gys1/Ppp2r2d/ Pfkfb1/Ppp2r5c/ Acacb/Scd1/Creb1/ Pfkp/Rps6kb1/Stk11/ Rab14/Pck2/Ccnd1 |
| mmu04140 | Autophagy-animal | 127 | −0.458 | −1.58 | 0.000375 | 0.007993 | 0.005708 | 6743 | tags = 54%, list = 32%, signal = 37% | Atg7/Akt1/Rps6kb2/ Atg2b/Rb1cc1/Uvrag/ Akt1s1/Pik3cb/ Pik3ca/Wipi2/ Sh3glb1/Mtmr14/ Atg3/Prkacb/Tsc1/ Pdpk1/Pik3cd/ Map2k1/Mapk8/Mapk9/ Lamp1/Akt2/Atg9b/ Atg4c/Ddit4/Atg12/ Atg9a/Prkcd/Rragc/ Rab7/Gm21596/ Pik3r2/Rragd/Rheb/ Bnip3/Vmp1/Rras/ Prkaa1/Ppp2ca/ Mapk1/Map3k7/ Ppp2cb/Pik3c3/ Hif1a/Camkk2/ Becn1/Igbp1/Raf1/ Rraga/Deptor/Mlst8/ Eif2ak4/Pten/Itpr1/ Eif2s1/Wipi1/ Lamp2/Nras/Dapk1/ Rragb/Mras/Rps6kb1/ Stk11/Supt20/ Mapk3/Hmgb1/Kras |
| mmu03410 | Base excision repair | 35 | −0.612 | −1.74 | 0.000205 | 0.005319 | 0.003799 | 5600 | tags = 71%, list = 27%, signal = 52% | Ogg1/Neil2/Mutyh/ Pole/Apex1/Pole4/ Nthl1/Gm21596/Ung/ Xrcc1/Pole3/Pold1/ Polb/Parp2/Pold2/ Neil3/Smug1/ Parp1/Lig1/Tdg/ Tdg-ps/Pold3/ Pole2/Hmgb1 |
| mmu01200 | Carbon metabolism | 108 | −0.445 | −1.51 | 0.002645 | 0.031021 | 0.022154 | 8140 | tags = 68%, list = 39%, signal = 42% | Aldoa/H6pd/Fh1/ Gldc/Mdh1/Acss1/ Cat/G6pdx/Pgls/ Idh3g/Got1/Taldo1/ Sucla2/Idnk/Pgp/ Gapdh/Aldoc/Pfkm/ Eno1/Sdhd/Pgam1/ Eno2/Prps2/Esd/ Idh1/Glyctk/Adh5/ Tkfc/Aco1/Aco2/ Tpi1/Eno1b/Dlat/ Pdha1/Gcsh/Gpi1/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| mmu04110 | Cell cycle | 123 | −0.546 | −1.88 | 1.25E−05 | 0.000995 | 0.00071 | 7953 | tags = 78%, list = 38%, signal = 49% | Phgdh/Acads/Shmt1/Suclg2/Dld/Idh3b/Pcx/Sdha/Shmt2/Adpgk/Pgk1/Pgd/Me2/Acat2/Idh2/Pccb/Pdhb/Echs1/Idh3a/Hk1/Pfkl/Ogdhl/Sdhb/Glud1/Tkt/Pcca/Hibch/Hk2/Me1/Acadm/Mthfr/Psat1/Psph/Pfkp/Aldh6a1/Gpt2 Espl1/Ccnb2/Pcna/Zbtb17/Cdc14a/Pkmyt1/Cdc26/Anapc11/Ccne1/Anapc7/Anapc10/Smad4/Ccnd2/Cdc6/Mcm7/Cdc23/Cdkn1a/Mcm3/E2f1/E2f4/Smc1b/Cdc27/Anapc1/Ccna2/Ywhaq/Wee1/E2f2/Ywhag/Mcm4/Mad2l2/Stag2/Skp2/Bub3/Orc2/Anapc5/Tgfb1/Atm/Cdk4/Hdac2/Orc6/Cdc25a/Plk1/Smad3/Cdc25c/Bub1b/Orc1/Mcm6/Skp1a/Mad2l1/Cdk2/E2f5/Mad1l1/Mcm2/Prkdc/Ccnb1/Orc5/Cdkn2a/E2f3/Rad21/Ywhah/Anapc2/Ccnh/Cul1/Ywhae/Cdk7/Rbl2/Ywhaz/Atr/Stag1/Chek2/Rbl1/Anapc4/Anapc13/Rbx1/Bub1/Orc4/Cdkn1b/Cdc7/Ccnd3/Hdac1/Tfdp2/Orc3/Gadd45a/Tfdp1/Smc3/Fzr1/Dbf4/Ywhab/Cdc14b/Chek1/Myc/Ttk/Ccnd1/Smc1a/Cdk6 |
| mmu04218 | Cellular senescence | 163 | −0.434 | −1.55 | 0.000562 | 0.008739 | 0.006241 | 5928 | tags = 47%, list = 28%, signal = 34% | Tgfbr1/Lin54/Ccna2/Rad9b/Pik3cb/Pik3ca/E2f2/Vdac2/Rbbp4/Traf3ip2/Ppp1cc/Tsc1/Pik3cd/Map2k1/Akt2/Vdac3/Tgfb1/Calm3/Atm/Cdk4/Foxm1/Cdc25a/Pik3r2/Rheb/Rras/Nfatc4/Smad3/Eif4ebp1/Lin52/Mapk1/Cdk2/E2f5/Rad9a/Nfatc3/Ccnb1/Cdkn2a/Lin9/Raf1/E2f3/Ppp3ca/Pten/Rad1/Itpr1/Rbl2/Mre11a/Atr/Sirt1/Chek2/Rbl1/Capn1/Rad50/Capn2/Calm2/Trpm7/Zfp36l1/Ccnd3/Itpr3/Nras/Gadd45a/Mybl2/Ppp3r1/Mras/Nbn/Chek1/Nfkb1/Myc/Mapk3/Ppp1cb/Vdac1/Ppid/Ccnd1/Ppp3cb/Kras/H2-M5/Cdk6/Zfp36l2 |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| mmu05220 | Chronic myeloid leukemia | 78 | −0.5 | −1.61 | 0.00055 | 0.008739 | 0.006241 | 6641 | tags = 56%, list = 32%, signal = 39% | Polk/Cdkn1a/E2f1/ Ctbp1/Tgfbr1/Cbl/ Pik3cb/Pik3ca/ E2f2/Stat5a/ Pik3cd/Map2k1/ Akt2/Cblc/Tgfb1/ Ddb2/Bax/Cdk4/ Hdac2/Pik3r2/ Sos1/Smad3/Ikbkb/ Mapk1/Runx1/ Cdkn2a/Raf1/ E2f3/Ctbp2/Braf/ Crk/Araf/Chuk/ Cdkn1b/Hdac1/Nras/ Gadd45a/Nfkb1/ Myc/Mapk3/Ccnd1/ Kras/Cdk6 |
| mmu04710 | Circadian rhythm | 31 | −0.561 | −1.56 | 0.005988 | 0.049006 | 0.034998 | 5459 | tags = 61%, list = 26%, signal = 45% | Csnk1e/Cry2/ Arntl/Rora/Per3/ Prkab2/Prkaa1/ Prkag1/Skp1a/ Cry1/Prkab1/Cul1/ Bhlhe41/Fbxl3/ Bhlhe40/Rbx1/ Clock/Creb1 |
| mmu00270 | Cysteine and methionine metabolism | 44 | −0.533 | −1.58 | 0.003444 | 0.03455 | 0.024675 | 8955 | tags = 82%, list = 43%, signal = 47% | Ldhc/Got2/Mdh2/ Sdsl/Amd1/Gm4737/ Mpst/Mdh1/Bcat1/ Got1/Tst/Bhmt2/ Gclc/Ldhal6b/ Dnmt3b/Apip/ Enoph1/Ldha/Mtr/ Mri1/Srm/Bcat2/ Gclm/Adi1/Sms/ Mat2a/Cbs/Bhmt/ Ahcyl1/Mat2b/ Ldhb/Ahcy/Dnmt1/ Cth/Il4i1 |
| mmu03030 | DNA replication | 35 | −0.631 | −1.79 | 7.70E−05 | 0.002992 | 0.002137 | 6723 | tags = 89%, list = 32%, signal = 60% | Pold4/Prim2/Mcm3/ Rpa2/Rnaseh2a/ Rpa1/Mcm4/Pole/ Rnaseh1/Pole4/ Rfc3/Rfc2/Rpa3/ Mcm6/Mcm2/Pole3/ Pold1/Rfc5/Rfc4/ Dna2/Pola2/Pold2/ Rnaseh2b/Ssbp1/ Lig1/Prim1/Pola1/ Pold3/Rfc1/Pole2 |
| mmu05213 | Endometrial cancer | 57 | −0.495 | −1.53 | 0.005292 | 0.044479 | 0.031765 | 8656 | tags = 70%, list = 41%, signal = 41% | Foxo3/Ctnnb1/ Map2k2/Cdh1/Hras/ Bak1/Tcf7l2/ Tcf7l1/Akt1/Polk/ Cdkn1a/Pik3cb/ Pik3ca/Apc2/ Pdpk1/Pik3cd/ Map2k1/Akt2/Axin1/ Ddb2/Bax/Ctnna1/ Casp9/Pik3r2/Sos1/ Mlh1/Mapk1/Apc/ Raf1/Braf/Tcf7/ Pten/Araf/Nras/ Gadd45a/Myc/Mpk3/ Ccnd1/Kras |
| mmu03460 | Fanconi anemia pathway | 50 | −0.536 | −1.62 | 0.001207 | 0.017056 | 0.012181 | 6787 | tags = 76%, list = 32%, signal = 52% | Faap100/Polk/ Fancb/Rmi2/Ercc1/ Rpa2/Fancg/ Faap24/Atrip/ Telo2/Rpa1/Brip1/ Top3b/Polh/Fancc/ Brca1/Mlh1/Rpa3/ Fancl/Fanca/ Rad51/Rev1/Fance/ Fancm/Rmi1/Rev3l/ Apitd1/Atr/Fancd2/ |

TABLE 4-continued

List of enriched genes

| | Description | setSize | enrich-mentScore | NES | pvalue | p. adjust | qvalues | rank | leading_edge | core_enrichment |
|---|---|---|---|---|---|---|---|---|---|---|
| mmu04666 | Fc gamma R-mediated phagocytosis | 84 | −0.476 | −1.55 | 0.001491 | 0.02016 | 0.014398 | 7610 | tags = 61%, list = 36%, signal = 39% | Poli/Pms2/Fanci/Blm/Brca2/Wdr48/Hes1/Usp1 Wasf2/Limk2/Dnm2/Pak1/Prkce/Sphk2/Akt1/Gsn/Rps6kb2/Pik3cb/Ncf1/Pik3ca/Pla2g6/Plcg1/Pik3cd/Map2k1/Arpc3/Akt2/Arpc5/Prkcd/Wasl/Asap3/Pik3r2/Cdc42/Asap1/Mapk1/Rac2/Cfl2/Rac1/Raf1/Vav2/Vasp/Arpc2/Limk1/Fcgr2b/Crk/Plpp1/Asap2/Arpc5l/Syk/Hck/Arpc1b/Wasf3/Pip5k1c/Arf6/Rps6kb1/Myo10/Mapk3/Pla2g4e/Marcks |
| mmu04068 | FoxO signaling pathway | 124 | −0.429 | −1.48 | 0.003878 | 0.036545 | 0.026099 | 5835 | tags = 44%, list = 28%, signal = 32% | Pik3cb/Pik3ca/Fbxo25/Csnk1e/Sgk3/Pdpk1/Pik3cd/Map2k1/Mapk8/Mapk9/Akt2/Atg12/Skp2/Tgfb1/Atm/Prkab2/Pik3r2/Bnip3/Prkaa1/Prkag1/Plk1/Sos1/Smad3/Ikbkb/Mapk1/Cdk2/Prmt1/Nlk/Plk4/Ccng2/Homer1/Ccnb1/Raf1/Prkab1/Braf/Sgk1/Pten/Rbl2/Sod2/Stat3/Araf/Sirt1/Usp7/Chuk/Klf2/Cdkn1b/Nras/Gadd45a/Stk11/Mapk3/Pck2/Ccnd1/Kras |
| mmu05161 | Hepatitis B | 126 | −0.472 | −1.63 | 0.000112 | 0.003886 | 0.002775 | 6682 | tags = 53%, list = 32%, signal = 36% | Akt1/Cdkn1a/Nfatc2/Tirap/E2f1/Ptk2b/D1Pas1/Tgfbr1/Birc5/Ccna2/Ywhaq/Pik3cb/Pik3ca/Creb3l1/Ikbke/E2f2/Stat5a/Pik3cd/Map2k1/Lamtor5/Mapk8/Mapk9/Jak1/Akt2/Ifnar1/Vdac3/Tgfb1/Casp3/Ddb2/Bax/Cdk4/Casp9/Pik3r2/Nfatc4/Atf6b/Map3k1/Stat1/Src/Ikbkb/Mapk1/Fos/Cdk2/Mavs/Nfatc3/Atf4/Ddx3x/Raf1/E2f3/Stat6/Pten/Ywhaz/Stat3/Chuk/Cdkn1b/Nras/Tbk1/Ddx58/Creb1/Ywhab/Nfkb1/Cycs/Myc/Mapk3/Ccnd1/Kras/Cdk6 |
| mmu04066 | HIF-1 signaling pathway | 97 | −0.444 | −1.48 | 0.005145 | 0.044443 | 0.03174 | 6752 | tags = 47%, list = 32%, signal = 32% | Arnt/Edn1/Akt1/Gapdh/Rps6kb2/Cdkn1a/Eif4e2/Eno1/Egln2/Eno2/Pik3cb/Pik3ca/Trf/Ldha/Plcg1/Pik3cd/Map2k1/Akt2/Eno1b/Camk2g/Pfkfb3/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| | | | | | | | | | | Pdha1/Timp1/ Mknk1/Pik3r2/ Eif4ebp1/Mapk1/ Pgk1/Hif1a/Pdhb/ Stat3/Cul2/Hk1/ Pfkl/Egln1/Rbx1/ Hk2/Cdkn1b/Eif4e/ Rps6kb1/Nfkb1/ Mapk3/Tfrc/ Pdk1/Vegfa |
| mmu03440 | Homologous recombination | 39 | −0.586 | −1.7 | 0.000449 | 0.008735 | 0.006238 | 7706 | tags = 87%, list = 37%, signal = 55% | Palb2/Eme1/ Rad51c/Pold4/ Rpa2/Xrcc3/ Rad54l/Rpa1/ Brip1/Uimc1/ Top3b/Atm/ Sycp3/Rbbp8/ Brca1/Rpa3/ Rad51/Bard1/ Topbp1/Rad51b/ Pold1/Pold2/ Mre11a/Xrcc2/ Ssbp1/Fam175a/ Rad50/Blm/ Rad54b/Pold3/ Brca2/ Nbn/Brcc3 |
| mmu05016 | Huntington's disease | 179 | −0.406 | −1.47 | 0.002687 | 0.031021 | 0.022154 | 9351 | tags = 71%, list = 45%, signal = 40% | Atp5d/Uqcr11/ Polr2j/Ndufs7/ Nrf1/Uqcr10/ Ndufa4/Dnah10/ Polr2f/Apaf1/ Dnal4/Cox6a1/ Ndufv2/Ndufa9/ Cox5a/Sdhc/ Cox7a2l/Ndufb9/ Creb3/Uqcrfs1/ Ppif/Ndufv1/ Atp5a1/Ndufs3/ Ndufa5/Ndufa7/ Cyct/Ap2b1/ Ndufs8/Slc25a5/ Cox4i1/Polr2c/ Ndufa13/Ucp1/ Ndufb5/Polr2d/ Ap2m1/Tbpl1/Ndufb2/ Ap2s1/Uqcrh/Polr2i/ Cox6b1/Ndufs5/ Atp5o/Hip1/Ndufa6/ Atp5e/Cox5b/Atp5h/ Sdhd/Polr2h/ Uqcrc1/Ndufb11/ Bbc3/Ndufa10/ Cox8a/Dnah2/ Dnaic2/Dnah6/ Cox6b2/Uqcrc2/ Cox4i2/Creb3l1/ Rcor1/Ndufs1/ Clta/Vdac2/Sod1/ Ndufs6/Ndufa1/ Cltb/Ap2a1/ Ndufb10/Dnal1/ Atp5g3/Cox7a2/ Vdac3/Atp5f1/ Ndufb3/Sin3a/ Uqcrb/Casp3/ Bax/Gnaq/Hdac2/ Tfam/Casp9/Ndufv3/ Tbp/Sdha/Ndufs4/ Ndufc2/Ndufb6/ Cox7b/Ndufc1/ Ift57/Gm3244/ Dctn2/Cox6c/ Polr2e/Cyc1/ Atp5c1/Itpr1/ |

TABLE 4-continued

List of enriched genes

| | Description | setSize | enrich-mentScore | NES | pvalue | p. adjust | qvalues | rank | leading_edge | core_enrichment |
|---|---|---|---|---|---|---|---|---|---|---|
| mmu05167 | Kaposi's sarcoma-associated herpesvirus infection | 174 | −0.407 | −1.47 | 0.002971 | 0.031021 | 0.022154 | 5728 | tags = 39%, list = 27%, signal = 28% | Atp5j/Sod2/Dctn4/ Ndufab1/Sdhb/ Atp5g2/Grin1/ Cox7c/Plcb4/ Hdac1/Ndufa4l2/ Dnah8/Uqcrq/ Creb1/Sp1/Plcb3/ Cycs/Dctn1/Vdac1/ Hap1/Rest/Tgm2 Pik3ca/Ikbke/ E2f2/Gngt2/ Atg3/Plcg1/ Pik3cd/Map2k1/ Mapk8/Mapk9/ Jak1/Akt2/ Ifnar1/Traf3/ Gnb4/Calm3/ Casp3/Bax/Cdk4/ Casp9/Pik3r2/ Nfatc4/Tyk2/ Stat1/Src/Ikbkb/ Mapk1/Fos/Pik3c3/ Hif1a/Irf9/ Nfatc3/Becn1/ Rac1/Gnb1/Raf1/ E2f3/Ppp3ca/ Itpr1/Stat3/Syk/ Map2k7/Gng2/ Eif2ak2/Hck/ Gng10/Calm2/ Prex1/Chuk/ Itpr3/Nras/ Tbk1/Creb1/Il6st/ Ppp3r1/Nfkb1/ Cycs/Myc/Mapk3/ Bid/Ccnd1/Gng5/ Ppp3cb/Kras/ H2-M5/Vegfa/Cdk6 |
| mmu04720 | Long-term poten-tiation | 61 | −0.539 | −1.68 | 0.000192 | 0.005319 | 0.003799 | 5296 | tags = 52%, list = 25%, signal = 39% | Adcy1/Prkacb/ Map2k1/Camk2g/ Calm3/Gnaq/ Mapk1/Atf4/ Rps6ka2/Rps6ka3/ Rap1a/Raf1/ Ppp3ca/Braf/ Ppp1r1a/Itpr1/ Rps6ka6/Araf/ Grin1/Plcb4/ Calm2/Itpr3/ Nras/Rap1b/ Ppp3r1/Plcb3/ Mapk3/Ppp1cb/ Rapgef3/Ppp3cb/ Kras |
| mmu01100 | Metabolic pathways | 1162 | −0.341 | −1.41 | 2.04E−05 | 0.00127 | 0.000907 | 9396 | tags = 59%, list = 45%, signal = 34% | Gcnt4/Plch1/ Enpp3/Chst10/ Ndufa8/Atp5d/ Uqcr11/Bpnt1/ Nt5c2/A4galt/ Ak7/Polr2j/ Phospho2/Ndufs7/ Mgat2/Extl3/ Glce/Akr1a1/ Atp5k/Uqcr10/ Hexa/Ctps2/ Ndufa4/Cmas/Gulo/ Polr2f/Cds2/ Lipt2/Pdxk/Mthfs/ C1galt1c1/Lpin3/ Aldh3a1/Glt28d2/ Cers1/Acss2/ Cers6/Mut/ Minpp1/Dgkd/ Mtap/Pip5k1b/ Pi4k2b/ |

TABLE 4-continued

List of enriched genes

| Description | setSize | enrichmentScore | NES | pvalue | p. adjust | qvalues | rank | leading_edge | core_enrichment |
|---|---|---|---|---|---|---|---|---|---|
| | | | | | | | | | Aass/Plpp2/ Pygl/Gba/Ldhc/ Xylt2/Cox6a1/ Prps1l3/Ndufv2/ Mecr/Cad/Chpf2/ Got2/Urah/ Gcnt1/Agpat5/ Ndufa9/Pla2g2c/ Gamt/Nos3/Galt/ Cox5a/Pigp/ Synj1/Cyp26c1/ Slc33a1/Sdhc/ Alg9/Xylb/ Atp6ap1/Tcirg1/ Nme1/Nme6/Hadhb/ Ptgs1/B3galt6/ Ak1/Akr1b3/ Ndufb9/Fut1/ Gpam/Rrm2b/ Chpf/Nat1/ Dctd/Mdh2/ Uqcrfs1/Nmnat3/ Aprt/Ndufv1/ Pank3/Dgat1/ Hmgcl/Hmox1/ Cox10/Mvk/ Atp5a1/Sdsl/ Csad/Agpat1/ Amd1/Gpat4/ Ggt6/Aldoa/ Ggt7/Pygm/ H2-Ke6/Ndst2/ Uck1/H6pd/ Atp6v1f/Ndufs3/ Polg/Acadl/Sgsh/ Polg2/Ndufa5/ Gm4737/Fh1/ Gldc/Mpst/Pla2g4c/ Ndufa7/Cyct/ Guk1/Pip5k1a/ Mdh1/Ndufs8/ Coq2/Dgka/Urod/ Gaa/Atp6v0b/ Gad1/Gba2/Hyal2/ Tyms/Extl2/ Acss1/Fech/ Nmnat1/Nadsyn1/ Ebp/Acp5/Ivd/ Cox4i1/Polr2c/ G6pdx/Pygb/Coq6/ Extl1/Kl/Pycrl/ Bcat1/B4galt1/Nfs1/ Pgls/Ndufa13/ Gbgt1/Dmgdh/ Hsd17b1/Gne/ Idh3g/Gatb/ Gmppb/Acsl1/Fut8/ Ndufb5/B3galt4/ Smpd4/Ppcs/Polr2d/ Agpat2/Pik3c2b/ Tsta3/Hsd17b12/ Galnt6/Hmox2/ Nadk/Ndufb2/Got1/ Impdh2/St3gal2/ Taldo1/Coq3/ Tk1/Inpp5b/Sat2/ Sucla2/Aldh4a1/ Nudt12/Itpa/Tusc3/ Dguok/Mtmr2/Idnk/ Znrd1/Pgp/Dhcr24/ Asns/Qrsl1/Cpox/ Mpi/Rpn2/Acaa1a/ Nt5c3b/Mgat1/ Sphk2/Ampd2/Uqcrh/ Mtmr4/Polr2i/Ctps/ |

TABLE 4-continued

List of enriched genes

| Description | setSize | enrichmentScore | NES | pvalue | p. adjust | qvalues | rank | leading_edge | core_enrichment |
|---|---|---|---|---|---|---|---|---|---|
| | | | | | | | | | Ddost/Tst/Atp5l/ Hykk/Bhmt2/Dpagt1/ Uxs1/Dpm1/Gclc/ Cox6b1/Degs1/Sc5d/ Gart/Ptgis/Gpaa1/ Ndufs5/Blvrb/ Odc1/Atp5o/Gapdh/ Impad1/Man2a2/ Polr3h/Ldhal6b/ Fut2/Pold4/ Aldoc/Pgm2/Pfkm/ Fuk/Ndufa6/ Prim2/Gmps/Pigu/ Pipox/Pgs1/ Polr1c/Pigo/ Fahd1/Atp5e/ Rrm1/Cox5b/Eno1/ Polr1e/Chsy1/ Lama5/Upp1/Atp5h/ Dnmt3b/Ptges/ Sdhd/Glb1/Polr2h/ Galnt7/Pgam1/ Acad8/Pgm3/Gfpt2/ Uqcrc1/Sat1/ Ndufb11/Maoa/ Apip/Coq5/Ndufa10/ Papss1/Cox8a/Alg3/ Fdps/Pik3c2a/ Dctpp1/Ampd3/Eno2/ Nme3/Dpm2/Trit1/ Cox6b2/Acaa2/ Alg5/Mocs1/ Pafah1b3/Pld3/ Ckb/Uqcrc2/ Cyp4f13/Pycr2/ Cox4i2/Nt5c/Flad1/ Prps2/Bckdha/ St3gal3/Qprt/ Cers2/Ndufs1/ St6galnac4/ Adssl1/Plcd1/ Asl/Kdsr/Hmbs/ Pla2g12a/Mccc1/ Pigc/Pigl/Ass1/ Gfpt1/Ak6/Tpk1/ Hsd17b7/Pomk/ Impa1/Enoph1/Hlcs/ Polr1b/B4galnt1/ Acsl6/Idh1/Pla2g6/ Dpm3/Smpd2/ Glyctk/Gnpda2/ Stt3a/Mtmr1/ Ext2/Mtmr7/Ldha/ Mthfd1/Mtmr14/ Inpp5k/Pigh/ Adh5/Pfas/Polr3gl/ Plcg1/Aldh9a1/ Fdft1/Atp6v0a2/ Atp5j2/Ndufs6/ Ndufa1/Csgalnact2/ Plch2/Pign/Ocrl/ Pi4k2a/Tkfc/ Ndufb10/Aco1/ Aco2/Tpi1/Nme7/ Mgat5/Nt5c3/ Atp5g3/Nans/ Scp2/Pole/Sptlc1/ Dut/Galk1/Mtr Atp6v1g1/Uprt/ Ntpcr/Gcdh/Atp5f1/ Pafah2/Mri1/Pank1/ Ndufb3/Man1b1/ Nme2/Ganab/Cers4/ Mtmr6/B4galnt3/ Cndp2/Eno1b/Dlat/ |

TABLE 4-continued

List of enriched genes

| Description | setSize | enrichmentScore | NES | pvalue | p. adjust | qvalues | rank | leading_edge | core_enrichment |
|---|---|---|---|---|---|---|---|---|---|
| | | | | | | | | | Gstz1/Mthfd2l/ Fpgs/Tm7sf2/ Uqcrb/Atp6v1g2/ Pmm2/Pdha1/Pole4/ B4galt4/Dhfr/ Hsd17b4/Gcsh/ Qars/Polr1d/ Dse/Ggps1/Cd38/ Gpi1/Tmem5/ Phgdh/Acads/ Afmid/Srm/Sqle/ Dck/Mvd/Hsd17b10/ Uck2/Shmt1/ Ears2/B4galt6/Rfk/ Mmab/Pla2g5/ Gmppa/Dbt/Adss/ Man2a1/Pi4ka/Ak2/ Acaca/Itpkc/Chpt1/ Ext1/Alg14/Prodh/ Acadsb/Ndufv3/ Suclg2/Mgat5b/ Ipmk/Dld/Itpka/ Rdh11/Idh3b/Fpgt/ Ppcdc/Aldh5a1/ Mocs2/Ptdss2/Pcx/ Rrm2/Hyal1/Sdha/ Ndufs4/Shmt2/ Ndufc2/Auh/ Pafah1b1/Ndufb6/ Cox7b/Adpgk/ Agk/Pgk1/Pcyt1b/ Alg10b/Pigk/ Gcnt2/Ndufc1/ Polr3b/Gls2/ Bpgm/Pik3c3/ Gm3244/Bcat2/ Hmgcr/Lap3/Gclm/ Agpat4/Pank4/ Inpp5f/Adk/ Atp6v1d/Hadh/ Polr3g/Pgd/Thtpa/ Pigm/Pigw/ 1700061G19Rik/ Agps/Cox6c/ Hsd3b7/Coq7/ Polr2e/Fktn/Acsl4/ Bckdhb/Acat2/ Aldh18a1/Dtymk/ Tk2/Idh2/Gnpda1/ Rpn1/Bdh1/ Cox11/Pgm1/Pccb/ Plce1/Crls1/ Galnt1/Pdhb/Pisd/ Nt5e/Adi1/Sacm1l/ Aldh7a1/Pigb/Acp2/ Ggt1/Pole3/Pold1/ B3galnt1/Acly/ St3gal4/Sms/Adsl/ Alg13/Pigf/Cyc1/ Atp5c1/Rev3l/Gcnt3/ Pla2g1b/B4galt7/ St6galnac6/Pigx/ Hexb/Mccc2/ Polr3d/Isyna1/ Lias/Lpin1/Plcd3/ B3galnt2/Acp1/ Acy1/Atp5j/Cyp51/ Pola2/Pold2/ Sephs1/Mat2a/ Pmvk/Echs1/Ppat/ Lss/Idh3a/Polr3f/ Pank2/Atic/ Inpp4a/Hk1/Pnpla3/ Pfkl/B3gnt2/Alg11/ Ogdhl/Pafah1b2/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| | | | | | | | | | | Plpp1/Stt3b/Cbs/ Ugcg/Ndufab1/ Sdhb/Acsl3/Glud1/ Paics/Gys1/Nos1/ Atp5g2/Nampt/ C1galt1/Tkt/ Inpp5a/Pcca/Hibch/ Hk2/Bhmt/Cox7c/ St6galnac3/ Mthfd1l/ Cept1/Ado/Plcb4/ Me1/Acadm/ St8sia1/Hibadh/ Mgat3/Pycr1/ Chkb/Dpys/Cers5/ Acox3/Cox17/ Ahcyl1/Acacb/ Ugdh/Polr3k/ Prim1/Pgap1/ Asah1/Pip5k1c/ Nsdhl/Acsm4/Eprs/ Ndufa4l2/Alpl/ Hmgcs1/Mthfr/Pola1/ Pold3/Uqcrq/Mat2b/ Mthfd2/Nmnat2/ Bdh2/Ldhb/Psat1/ Mtm1/Dhodh/Psph/ Dgke/Qdpr/Impa2/ Ephx2/Ahcy/Aldh2/ Pfkp/Plcb3/Msmo1/ Pole2/Cmpk1/ Synj2/Dnmt1/ Twistnb/Pomt1/ B3gnt5/Gk/Cth/ Il4i1/Cycs/Fah/ Ddc/Pcyt2/Piga/ Alg6/Aldh6a1/ Gls/Etnk1/Ptges3/ Pck2/Nadk2/ B4galnt4/Idi1/Gpt2/ Pla2g4e/Fut9/Itpk1 |
| mmu03430 | Mismatch repair | 22 | −0.649 | −1.7 | 0.001072 | 0.015871 | 0.011334 | 6418 | tags = 91%, list = 31%, signal = 63% | Rpa2/Rpa1/Msh3/ Rfc3/Rfc2/Mlh1/ Rpa3/Pold1/Rfc5/ Rfc4/Pold2/Msh2/ Ssbp1/Msh6/Mlh3/ Pms2/Lig1/Pold3/ Rfc1 |
| mmu04137 | Mitophagy-animal | 62 | −0.491 | −1.53 | 0.004115 | 0.036567 | 0.026115 | 5465 | tags = 56%, list = 26%, signal = 42% | Mfn1/Mapk8/Mapk9/ Tomm7/Atg9b/ Rhot1/Csnk2a1/ Atg9a/Csnk2a2/ Usp30/Tbc1d17/ Rab7/Bnip3/Rras/ Src/Cited2/Tfe3/ Nbr1/Hif1a/Atf4/ Becn1/Tbc1d15/ Tax1bp1/Bnip3l/ Usp15/Usp8/ Nras/Tbk1/Sp1/ Mras/Tfeb/Kras/ Optn/Mitf |
| mmu04150 | mTOR signaling pathway | 145 | −0.444 | −1.56 | 0.000543 | 0.008739 | 0.006241 | 6641 | tags = 50%, list = 32%, signal = 34% | Rictor/Wnt5b/ Rps6kb2/Eif4e2/ Fzd7/Sesn2/ Akt1s1/Pik3cb/ Pik3ca/Mapkap1/ Telo2/Strada/ Tsc1/Pdpk1/ Pik3cd/Map2k1/ Lamtor5/Akt2/ Fzd10/Ddit4/ Skp2/Atp6v1g1/ Depdc5/Rhoa/ Fnip1/Grb10/ |

TABLE 4-continued

List of enriched genes

| | Description | setSize | enrich-mentScore | NES | pvalue | p. adjust | qvalues | rank | leading_edge | core_enrichment |
|---|---|---|---|---|---|---|---|---|---|---|
| | | | | | | | | | | Atp6v1g2/Clip1/ Wdr24/Rragc/ Fnip2/Pik3r2/ Rragd/Rheb/ Prkaa1/Sos1/ Eif4ebp1/Lamtor2/ Ikbkb/Mapk1/ Atp6v1d/Eif4b/ Rps6ka2/Wnt3a/ Rps6ka3/Dvl1/ Raf1/Rraga/Braf/ Deptor/Mlst8/ Sgk1/Cab39l/ Lpin1/Pten/ Rps6ka6/Lamtor3/ Wdr59/Dvl2/ Chuk/Eif4e/Nras/ Slc7a5/Rragb/ Slc3a2/Rps6kb1/ Stk11/Mapk3/ Seh1l/Kras/Fzd5 |
| mmu03420 | Nucleotide excision repair | 44 | −0.572 | −1.69 | 0.000386 | 0.007993 | 0.005708 | 6418 | tags = 84%, list = 31%, signal = 59% | Ercc1/Rpa2/ Rad23a/Rpa1/ Gtf2h5/Pole/ Gtf2h3/Pole4/ Ddb2/Cul4a/ Rfc3/Rfc2/Xpc/ Gtf2h1/Rpa3/ Ercc5/Cetn2/ Ercc8/Cul4b/ Mnat1/Ercc6/ Ccnh/Pole3/ Pold1/Rfc5/ Rfc4/Cdk7/ Pold2/Rbx1/ Gtf2h2/Lig1/ Ercc2/Pold3/ Rfc1/Rad23b/ Pole2 |
| mmu04114 | Oocyte meiosis | 108 | −0.44 | −1.49 | 0.003767 | 0.036545 | 0.026099 | 7896 | tags = 63%, list = 38%, signal = 39% | Ccnb2/Pkmyt1/ Cdc26/Calml4/ Pgr/Anapc11/ Ccne1/Anapc7/ Anapc10/Rps6ka1/ Ppp2r1b/Cdc23/ Ppp2r5b/Aurka/ Smc1b/Cdc27/ Anapc1/Ywhaq/ Ywhag/Ppp1cc/ Adcy1/Prkacb/ Map2k1/Mad2l2/ Ppp2r5a/Anapc5/ Cpeb3/Camk2g/ Calm3/Ppp2r5e/ Plk1/Ppp2ca/ Cdc25c/Stag3/ Skp1a/Mad2l1/ Mapk1/Cdk2/ Ppp2cb/Rps6ka2/ Ccnb1/Rps6ka3/ Ywhah/Anapc2/ Cul1/Ppp3ca/ Ywhae/Itpr1/ Ywhaz/Fbxo5/ Rps6ka6/Anapc4/ Anapc13/Rbx1/ Calm2/Bub1/ Ppp2r5c/Itpr3/ Smc3/Slk/ Ppp3r1/Ywhab/ Mapk3/Ppp1cb/ Sgol1/Ppp3cb/Smc1a |
| mmu00190 | Oxidative phosphor- ylation | 116 | −0.44 | −1.5 | 0.002723 | 0.031021 | 0.022154 | 9494 | tags = 78%, list = | Atp6v1c1/Ndufa3/ Atp6v0a1/Atp6v0e/ Ndufb8/Ndufa8/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| | | | | | | | | | 45%, signal = 43% | Atp5d/Uqcr11/ Ndufs7/Atp5k/ Uqcr10/Ndufa4/ Cox6a1/Ndufv2/ Ndufa9/Cox5a/ Sdhc/Atp6ap1/ Tcirg1/Cox7a2l/ Ndufb9/Uqcrfs1/ Ndufv1/Cox10/ Atp5a1/Atp6v1f/ Ndufs3/Ndufa5/ Ndufa7/Ndufs8/ Atp6v0b/Cox4i1/ Ndufa13/Ndufb5/ Ndufb2/Uqcrh/ Atp5l/Cox6b1/ Ndufs5/Atp5o/ Ndufa6/Atp5e/ Cox5b/Atp5h/ Sdhd/Uqcrc1/ Ndufb11/Ppa1/ Ndufa10/Cox8a/ Cox6b2/Uqcrc2/ Cox4i2/Ndufs1/ Atp6v0a2/Atp5j2/ Ndufs6/Ndufa1/ Ndufb10/Atp5g3/ Cox7a2/Atp6v1g1/ Atp5f1/Ndufb3/ Uqcrb/Atp6v1g2/ Ndufv3/Sdha/ Ndufs4/Ndufc2/ Ndufb6/Cox7b/ Ndufc1/Gm3244/ Atp6v1d/Ppa2/ Cox6c/Lhpp/Cox11/ Cyc1/Atp5c1/ Atp5j/Ndufab1/ Sdhb/Atp5g2/ Cox7c/Cox17/ Ndufa4l2/Uqcrq |
| mmu05212 | Pancreatic cancer | 75 | −0.535 | −1.72 | 5.12E−05 | 0.002273 | 0.001624 | 6641 | tags = 63%, list = 32%, signal= 43% | Polk/Rps6kb2/ Cdkn1a/E2f1/ Tgfbr1/Pik3cb/ Pik3ca/E2f2/ Pik3cd/Map2k1/ Mapk8/Mapk9/ Jak1/Akt2/Tgfb1/ Ddb2/Bax/Cdk4/ Casp9/Pik3r2/ Cdc42/Smad3/ Stat1/Ikbkb/ Mapk1/Rad51/ Rac2/Rac1/ Cdkn2a/Raf1/ E2f3/Braf/Stat3/ Araf/Ralb/Chuk/ Gadd45a/Brca2/ Rps6kb1/Nfkb1/ Ralbp1/Mapk3/ Ccnd1/Kras/ Vegfa/Cdk6 |
| mmu05200 | Pathways in cancer | 379 | −0.358 | −1.39 | 0.002992 | 0.031021 | 0.022154 | 6154 | tags = 39%, list = 29%, signal = 28% | Gng12/Fzd7/ Egln2/Fgf9/ Ppard/Tgfbr1/ Birc5/Cbl/ Pik3cb/Pik3ca/ Ncoa4/E2f2/ Stat5a/Lpar6/ Apc2/Gngt2/ Adcy1/Prkacb/ Msh3/Plcg1/ Pik3cd/Map2k1/ Fgf3/Mapk8/ Mapk9/Jak1/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| | | | | | | | | | | Akt2/Fzd10/ Axin1/Traf3/ Cblc/Skp2/ Fgf15/Rhoa/ Tgfb1/Gnb4/Fn1/ Tpm3/Casp3/Bax/ Fgf17/Gnaq/ Cdk4/Gna13/ Hdac2/Ctnna1/ Casp9/Pik3r2/ Cdc42/Sos1/ Rock1/Smad3/ Mlh1/Gnai3/ Pml/Itga6/ Stat1/Itgb1/ Ikbkb/Mapk1/Fos/ Cdk2/Rad51/ Hsp90ab1/Lamb2/ Lpar2/Hif1a/ Zbtb16/Lpar4/ Rac2/Apc/Runx1/ Fgf11/Rac1/ Wnt3a/Cdkn2a/ Gnb1/Dvl1/Raf1/ Lpar5/E2f3/Max/ Ctbp2/Ptk2/Braf/ Rassf1/Tcf7/Pten/ Kif7/Hsp90b1/ Msh2/Rara/Pdgfa/ Stat3/Cul2/ F2r/Ccdc6/Crk/ Araf/Arhgef1/ Msh6/Ralb/Vegfc/ Plekhg5/Egln1/ Dvl2/Rbx1/Gng2/ Tpr/Gng10/Plcb4/ Gli1/Chuk/ Cdkn1b/Hdac1/ Ptch1/Nras/ Fgf4/Appl1/ Rock2/Birc2/ Hsp90aa1/Dapk1/ Xiap/Brca2/ Pias2/Plcb3/ Cks2/Lama1/ Nfkb1/Cycs/ Ralbp1/Myc/Lamc2/ Mapk3/Bmp4/ Fgf10/Bid/Ccnd1/ Gng5/Rasgrp2/ Kras/Vegfa/ Fzd5/Cdk6/Mitf |
| mmu00240 | Pyrimidine metabolism | 96 | −0.455 | −1.52 | 0.002866 | 0.031021 | 0.022154 | 6992 | tags = 58%, list = 33%, signal = 39% | Znrd1/Nt5c3b/ Polr2i/Ctps/ Entpd4/Entpd5/ Polr3h/Pold4/ Prim2/Polr1c/ Rrm1/Polr1e/ Upp1/Cant1/ Polr2h/Dctpp1/ Nme3/Nt5c/ Polr1b/Polr3gl/ Nme7/Nt5c3/Pole/ Dut/Uprt/Nme2/ Pole4/Polr1d/ Dck/Uck2/Rrm2/ Polr3b/Nudt2/ Polr3g/Polr3e/ Polr2e/Dtymk/ Tk2/Nt5e/Pole3/ Pold1/Polr3d/ Pola2/Pold2/ Polr3f/Dpys/ Polr3k/Prim1/ Pola1/Pold3/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| mmu04810 | Regulation of actincytoskeleton | 204 | −0.392 | −1.44 | 0.004067 | 0.036567 | 0.026115 | 5786 | tags = 43%, list = 28%, signal = 31% | Dhodh/Pole2/ Cmpk1/Twistnb/ Pnpt1 Pik3cb/Pik3ca/ Pak2/Ssh1/ Apc2/Ppp1cc/ Pik3cd/Map2k1/ Fgf3/Arpc3/Fgf15/ Arpc5/Rhoa/Cyfip1/ Ezr/Fn1/Vcl/ Pip4k2a/Arhgef7/ Fgf17/Pdgfc/ Pikfyve/Gna13/ Iqgap3/Wasl/ Dock1/Pik3r2/ Cdc42/Nckap1l/ Rras/Sos1/Rock1/ Mylpf/Itga6/ Src/Itgb1/Myl7/ Tmsb4x/Mapk1/ Rdx/Pfn2/Pak4/ Rac2/Cfl2/Apc/ Fgf11/Rac1/ Raf1/Msn/Ptk2/ Braf/Vav2/ Ppp1r12c/Arpc2/ Myh10/Myl12a/ Diaph2/Pdgfa/ Myl12b/Limk1/ F2r/Ppp1r12a/ Crk/Araf/ Arhgef1/Arpc5l/ Actn1/Myh14/ Iqgap2/Nckap1/ Arpc1b/Pip5k1c/ Nras/Fgf4/ Rock2/Tiam1/ Mras/Itga9/ Itgb7/Mapk3/ Ppp1cb/Actn4/ Enah/Myh9/ Fgf10/Pip4k2b/ Kras |
| mmu03010 | Ribosome | 166 | −0.482 | −1.73 | 1.22E−05 | 0.000995 | 0.00071 | 8967 | tags = 81%, list = 43%, signal = 47% | Rpl7a/Mrpl2/ Rps28/Mrps7/ Mrpl16/Mrpl32/ Fau/Rpl32/Rpl26/ Mrpl3/Rpl37a/ Mrpl20/Rps6/ Gm4705/Rpl24/Rps2/ Rps19/n-R5s124/ n-R5s128/n-R5s111/ Gm22291/n-R5s142/ n-R5s100/Gm25018/ n-R5s139/n-R5s113/ Gm26391/n-R5s122/ n-R5s110/n-R5s138/ n-R5s103/Gm23284/ Gm22109/n-R5s121/ n-R5s149/n-R5s143/ n-R5s123/n-R5s141/ n-R5s105/n-R5s134/ n-R5s146/Gm25212/ n-R5s104/n-R5s108/ n-R5s133/Rn5s/ n-R5s117/n-R5s144/ Rps15a/Mrpl34/ Rpl19/Rpl36al/ Rpl10a/Rpl13/Rps9/ Rps18/Rpl28/Rps4x/ Mrpl9/Rpl34/Rpsa/ Rpl27/Mrps2/ Rpl36a/Rps15/ Gm8210/Rpl18a/Rpl23/ Mrpl11/Rpl7/Rps23/ |

TABLE 4-continued

List of enriched genes

| | Description | setSize | enrichmentScore | NES | pvalue | p. adjust | qvalues | rank | leading_edge | core_enrichment |
|---|---|---|---|---|---|---|---|---|---|---|
| mmu03008 | Ribosome biogenesis in eukaryotes | 105 | −0.532 | −1.8 | 1.26E−05 | 0.000995 | 0.00071 | 8436 | tags = 85%, list = 40%, signal = 51% | Mrpl4/Mrps15/ Mrpl28/Mrpl36/ Mrpl15/Rpl9/ Mrpl35/Rpl29/Rps25/ Rps27/Rplp2/Rsl24d1/ Mrpl22/Rps3a1/Rpl8/ Rpl38/Rpl35a/Rps24/ Mrps18c/Rpl11/Rps8/ Rpl17/Mrps16/Rpl3/ Mrpl21/Mrpl33/ Rpl34-ps1/Rpl4/ Mrpl30/Rps21/Mrpl27/ Uba52/Rpl35/Rpl36/ Rps27a/Mrpl19/ Rps27l/Mrpl14/ Rpl14/Rpl5/Rpl37rt/ Mrps14/Rpl27a/ Mrpl18/Mrps21/ Rpl30/Mrps17/ Rpl10/Rpl22/Mrpl13/ Mrps6/Mrps12/Mrps9/ Mrps18a/Mrpl1/Rpl21/ Mrps5/Mrpl24/Rpl39/ Mrps10/Rpl22l1/ Rps13/Rpl12 n-R5s124/n-R5s128/ n-R5s111/Gm22291/ n-R5s142/n-R5s100/ Gm25018/n-R5s139/ n-R5s113/Gm26391/ n-R5s122/n-R5s110/ n-R5s138/n-R5s103/ Gm23284/Gm22109/ n-R5s121/n-R5s149/ n-R5s143/n-R5s123/ n-R5s141/n-R5s105/ n-R5s134/n-R5s146/ Gm25212/n-R5s104/ n-R5s108/n-R5s133/ Rn5s/n-R5s117/ n-R5s144/Pop5/ Nol6/Emg1/Rexo1/ Fcf1/Rrp7a/Nxf3/ Nxt1/Spata5/Rcl1/ Heatr1/Nat10/ Nhp2/Nxf1/Ak6/ Rpp38/Nop10/Utp6/ Nmd3/Ran/Xrn2/ Csnk2a1/Pop1/ Csnk2a2/Wdr75/ Wdr3/Pop4/ 2610020H08Rik/ Lsg1/Nop56/Riok1/ Gnl3l/Rpp30/ Rexo2/Nob1/Gtpbp4/ Utp18/Gnl2/Bms1/ Sbds/Rpp40/Nvl/ Xrn1/Gnl3/Rbm28/ Rmrp/Wdr43/Dkc1/ Utp14a/Mphosph10/ Drosha/Gar1/Fbl/ Xpo1/Tcof1/ Nop58/Nxt2 |
| mmu03018 | RNA degradation | 75 | −0.589 | −1.89 | 1.28E−05 | 0.000995 | 0.00071 | 6413 | tags = 75%, list = 31%, signal = 52% | Pan2/Lsm3/Eno1/ Exosc1/Dcp1a/ Eno2/Tob1/Xrn2/ Cnot2/Lsm1/ Exosc2/Hspd1/ Cnot4/Eno1b/ Pnldc1/Lsm8/ Dcps/Skiv2l/ Skiv2l2/Lsm2/ Hspa9/Pabpc4/ Exosc3/Exosc7/ Exosc5/Papd5/ |

TABLE 4-continued

List of enriched genes

| Description | setSize | enrichmentScore | NES | pvalue | p. adjust | qvalues | rank | leading_edge | core_enrichment |
|---|---|---|---|---|---|---|---|---|---|
| mmu04530 Tight junction | 153 | −0.472 | −1.67 | 4.91E−05 | 0.002273 | 0.001624 | 5267 | tags = 53%, list = 25%, signal = 40% | Lsm6/Wdr61/Parn/Cnot10/Dcp1b/Ttc37/Exosc10/Cnot1/Dhx36/Mphosph6/Edc3/Pfkl/Papd7/Ddx6/Xrn1/Btg3/Lsm4/Cnot6/Pabpc1/Zcchc7/Pfkp/Exosc8/Pnpt1/Dis3/Pan3/Lsm5/Cnot7/Dcp2/Lsm7 Rab8a/Marveld2/Prkce/Myh11/Ppp2r1b/Myh13/Tjap1/Prkcz/Cldn14/Cldn7/Llgl2/Actb/Crb3/Prkacb/Mapk8/Mapk9/Scrib/Cd1d1/Arhgef2/Rhoa/Ezr/Tjp1/Amotl1/Tjp3/Cdk4/Prkab2/Wasl/Cdc42/Prkaa1/Prkag1/Mpp5/Rock1/Ppp2ca/Hspa4/Map3k1/Cttn/Sympk/Src/Itgb1/Pard6b/Rdx/Mpp4/Ppp2cb/Jam3/Tjp2/Runx1/Pard3/Rac1/Rap1a/Prkab1/Msn/Llgl1/Dlg3/Vasp/Actr3/Myh10/Prkci/Myl12a/Myl12b/Dlg1/Rapgef6/Myh7b/Ppp2r2d/Map2k7/Actn1/Myh14/Epb41l4b/Rap2c/Whamm/Nf2/Ybx3/Rock2/Tiam1/Stk11/Nedd4/Magi1/Rab8b/Actr2/Actn4/Myh9/Ccnd1 |
| mmu04120 Ubiquitin mediated proteolysis | 138 | −0.456 | −1.6 | 0.000285 | 0.006819 | 0.00487 | 7489 | tags = 59%, list = 36%, signal = 38% | Anapc11/Ube2q1/Anapc7/Anapc10/Ppil2/Fbxo2/Fbxw7/Cdc23/Pias1/Socs3/Ubr5/Fbxw8/Gm10705/Cdc27/Pias4/Ube2r2/Keap1/Anapc1/Cbl/Ube2d1/Ubox5/Mgrn1/Ube3b/Siah1a/Stub1/Cblc/Skp2/Det1/Ube2i/Anapc5/Ddb2/Cul4a/Rchy1/Ube2e1/Ube3c/Smurf1/Cul3/Trip12/Brca1/Ube2e3/Pml/AA414768/Map3k1/Itch/Fancl/Skp1a/Ercc8/Mid1/Uba2/Siah1b/Cul4b/Herc4/Wwp2/Anapc2/Cul1/Rfwd2/Rnf7/Cul2/Prpf19/Wwp1/Anapc4/Anapc13/Rbx1/Ube2k/Ube2d2a/Uba6/ |

TABLE 4-continued

List of enriched genes

| Description | setSize | enrichmentScore | NES | pvalue | p. adjust | qvalues | rank | leading_edge | core_enrichment |
|---|---|---|---|---|---|---|---|---|---|
| mmu00280 | Valine, leucine and isoleucine degradation | 53 | −0.521 | −1.59 | 0.002116 | 0.027426 | 0.019586 | 6160 | tags = 55%, list = 29%, signal = 39% | Ube3a/Sae1/ Trim37/Fzr1/ Birc2/Ube2b/Xiap/ Pias2/Uba3/Nedd4/ Ube2g1/Aire/ Ube2q2/Ube2d3 Acaa2/Bckdha/ Mccc1/Aldh9a1/ Acads/Hsd17b10/ Dbt/Acadsb/ Oxct1/Dld/Auh/ Bcat2/Hadh/ Bckdhb/Acat2/ Pccb/Aldh7a1/ Mccc2/Echs1/ Aacs/Pcca/Hibch/ Acadm/Hibadh/ Hmgcs1/Aldh2/ Il4i1/Aldh6a1 |

Note: columns shown left-to-right are Description, setSize, enrichmentScore, NES, pvalue, p. adjust, qvalues, rank, leading_edge, core_enrichment. The value 53 is setSize; −0.521 is enrichmentScore; −1.59 is NES; 0.002116 is pvalue; 0.027426 is p. adjust; 0.019586 is qvalues; 6160 is rank; the tags/list/signal block is leading_edge; the gene list is core_enrichment.

It was therefore asked if pharmacological suppression of glycolysis might promote the emergence of NELFA$^{high}$ mESCs in vitro. To this end, a glycolysis inhibitor, 2-deoxy-D-glucose (2-DG), was supplemented to NELFA reporter mESCs in conventional culture conditions and monitored for changes in NELFA$^{high}$ subpopulation. Strikingly, a prominent increase of up to 8-fold in the NELFA$^{high}$ subpopulation following 2-DG treatment was detected (FIG. 4b), in excellent agreement with the postulation. Pivotally, unbiased transcriptomic profiling of the unsorted 2-DG-treated NELFA reporter mESCs identified a total of 175 genes that were upregulated, including several key 2C genes (FIG. 4c). These 175 genes might also exert a function similar to Nelfa. Furthermore, a strong overlap of these upregulated genes with genes that are highly expressed in the early and late 2C-stage embryos (FIG. 4d), aforementioned 2C-like mESCs and in the NELFA$^{high}$ and Dox-NELFA-EGFP cells (FIG. 4h) was observed. In concordance, immunofluorescence analysis also showed the upregulation of the MERVL family of retrotransposons and Zscan4 in the 2-DG-treated NELFA-positive mESCs (FIG. 4e).

Figure 4F:
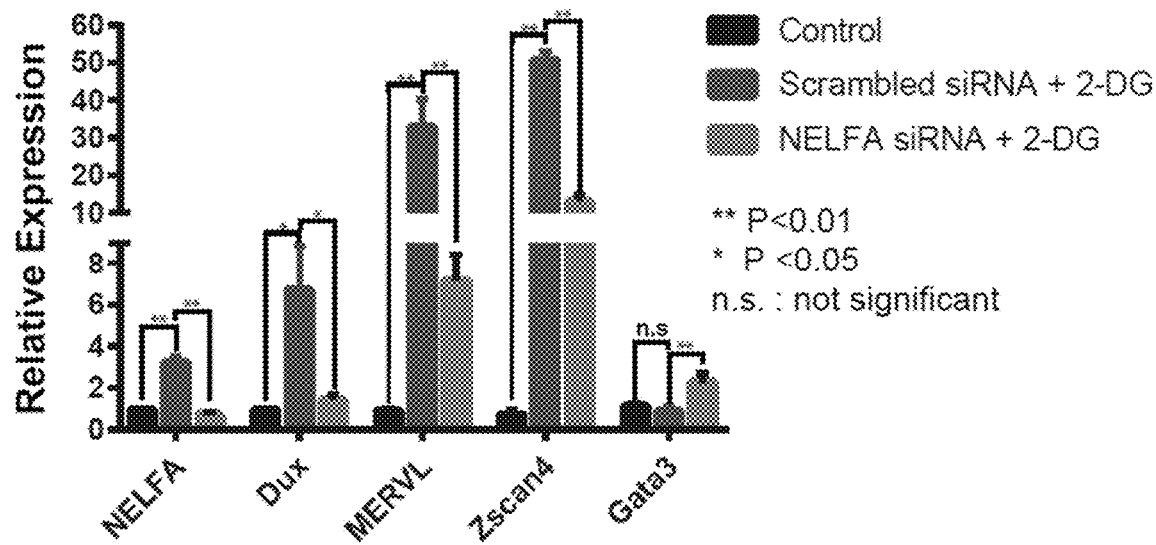
FIG. 4f is a bar graph depicting expression levels of various 2C-relevant genes, upon siRNA knockdown of Nelfa, in the presence of 2-DG treatment, by RT-qPCR. Error bars represent the standard deviation of 3 independent experiments. Indicated comparisons were done using paired two-sided Student's T-tests.
Figure 4G:
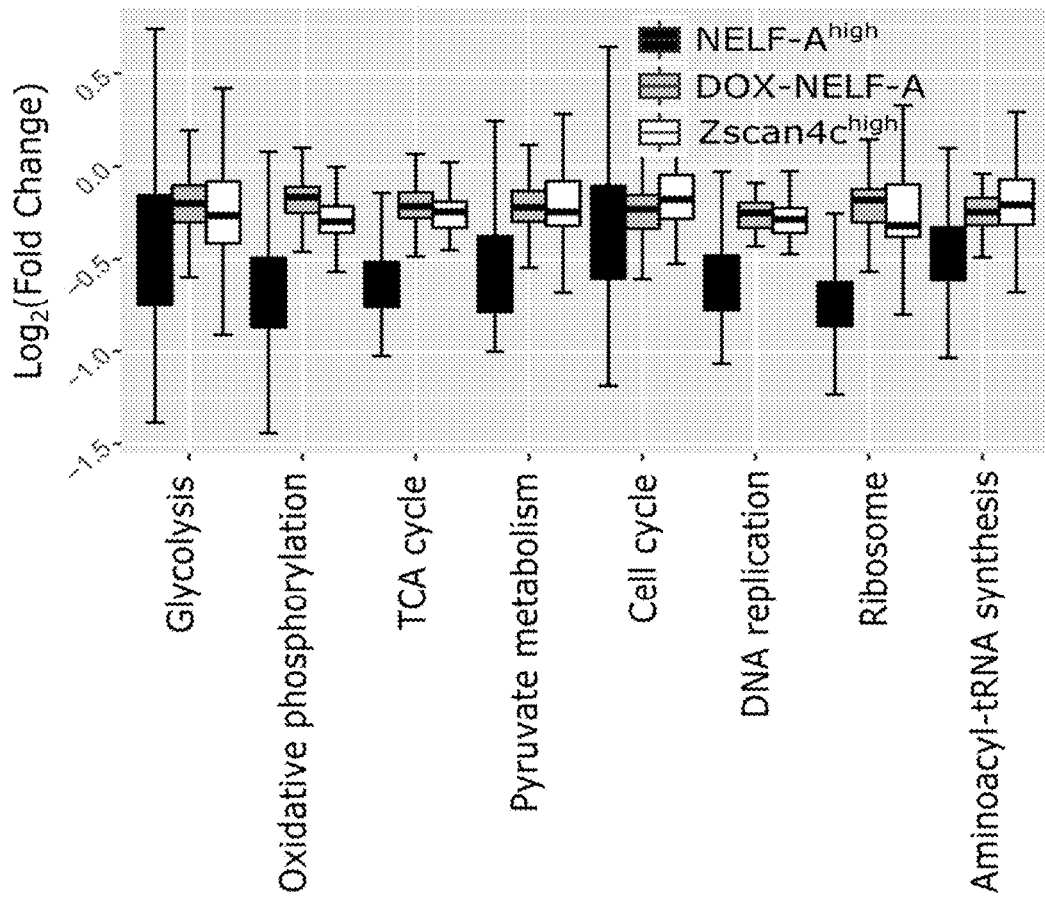
FIG. 4g is a box plot depicting the distribution of the change in gene expression (in units of log 2FC) of the genes from select KEGG pathway ontologies in NELFA$^{high}$ (black), Dox-inducible NELFA (grey), and Zscan4$^{high}$ cells (white), and demonstrates that these cells show reduced expression of metabolism-associated genes to varying degrees.
Figure 4H:
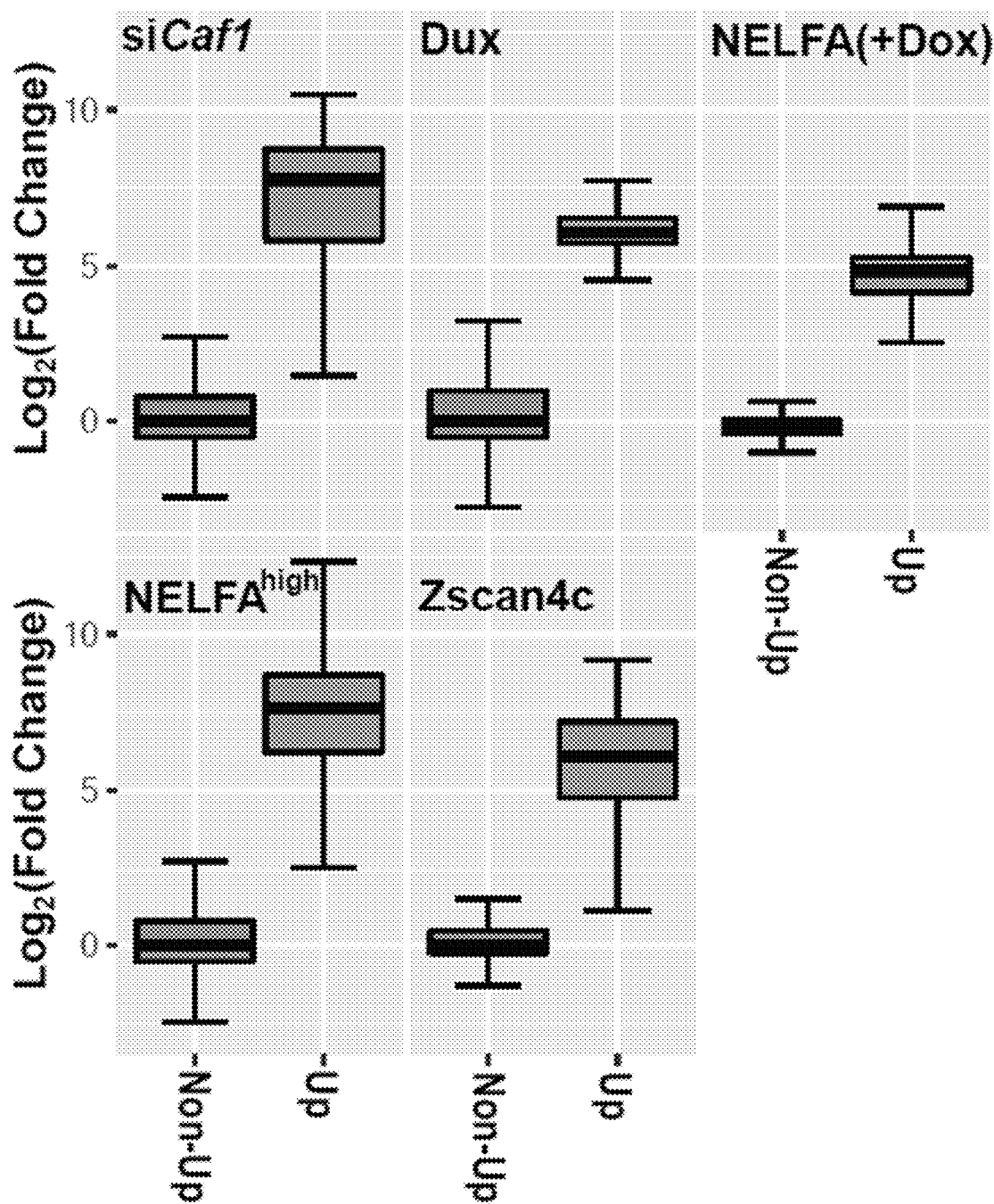
FIG. 4h is set of boxplots depicting the relative expressions of 2-DG induced genes (Up) and the rest (Non-Up) in 2C-like cells induced by CAF1 inhibition (upper-left panel), over-expression of Dux (upper middle panel) and NELFA (upper-right panel), NELFA$^{high}$ (bottom-left panel) and Zscan4-positive ESCs (bottom-right panel) respectively. 2-DG induced genes (n=175) are specifically upregulated in 2C-like mESC transcriptomes. Center line: median; box limits: lower and upper quartiles; upper whisker: the smaller value of the maximum value and upper quantile plus 1.5× the interquartile range; lower whisker: the larger value of the minimum value and the lower quantile minus 1.5× the interquartile range. Thus.

Next, to address if NELFA function is essential in this process, NELFA was knocked down in combination with 2-DG treatment, and impaired upregulation of several 2C genes such as Dux, Zscan4 and the MERVL/HERVL family of retrotransposons was observed (FIG. 4f). Notably, any significant induction of Gata3 upon 2-DG stimulation alone was not observed (FIG. 4f), which supports the previous conclusion that Gata3 is unlikely to be involved in 2C gene regulation. Interestingly, whereas Dux is downregulated when NELFA is abrogated in the presence of 2-DG, Gata3 is upregulated (FIG. 4f). This suggests a potential inverse relationship between Dux and Gata3 (see discussion). Taken together, it was shown that the suppression of glycolysis can promote the emergence of 2C-like mESCs and that NELFA remains a critical player in this process. Critically, the study uncovered for the first time a novel link between metabolism and the induction of 2C-like mESCs.

Example 7

Nelfa Interacts with Linker Histone H1 to Promote Chromatin Decondensation

Figure 5A:
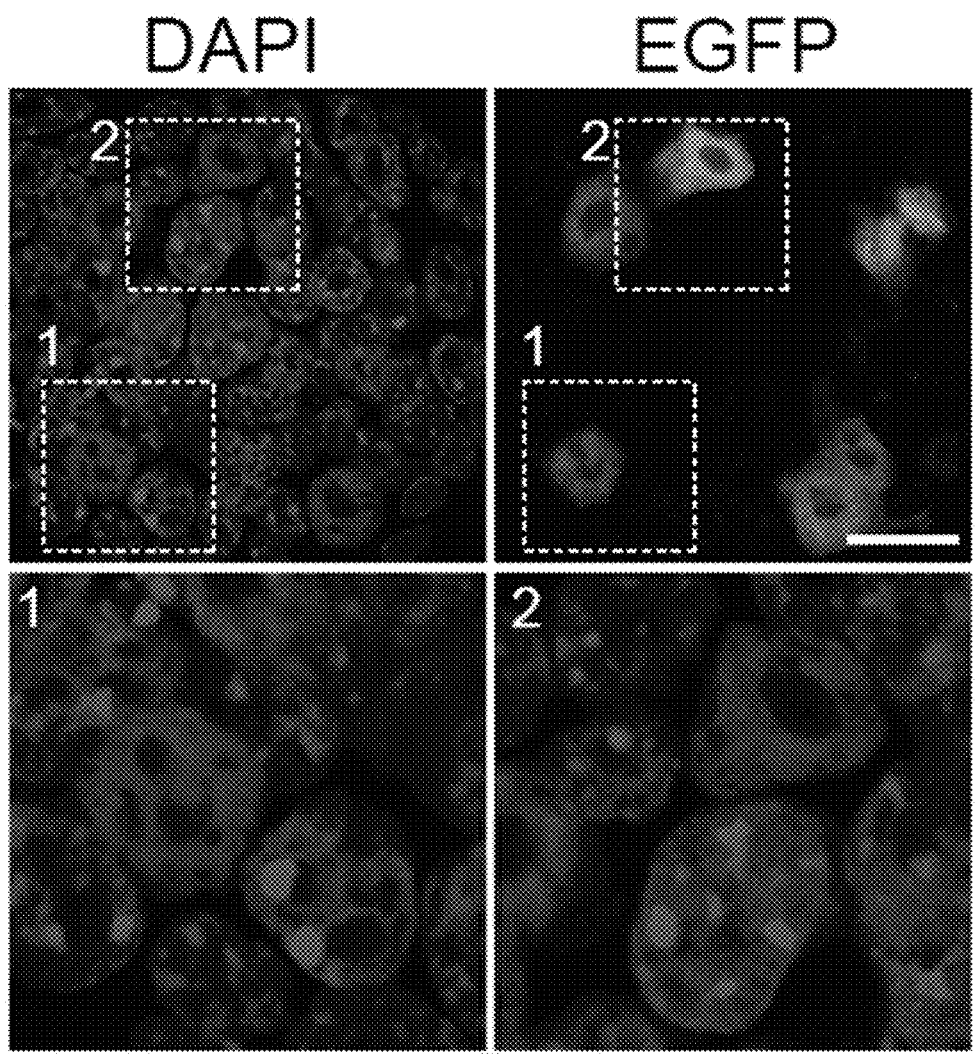
FIG. 5a is a set of microscopy images depicting immunofluorescence result for EGFP (NELFA) in NELFA-StrepHA-EGFP reporter mESCs revealed structural changes in heterochromatin. DAPI staining depicts the different extents of chromatin decondensation. Cells demarcated by white dotted boxes are shown in magnification. 5 independent experiments were performed.
Figure 5B:
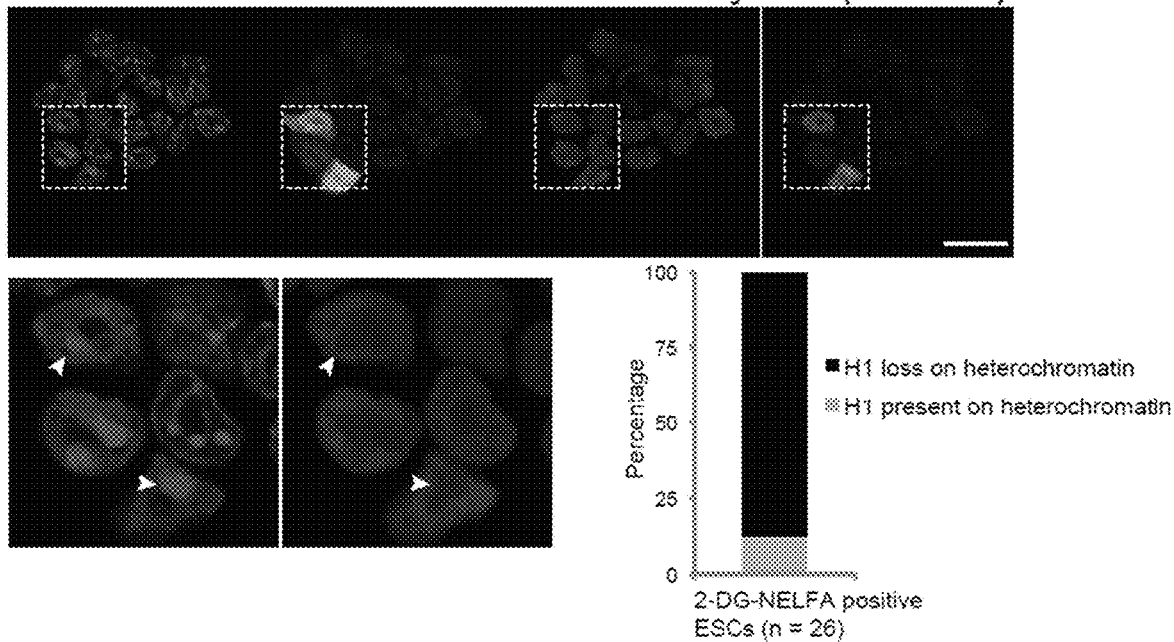
FIG. 5b is a set of microscopy images and a bar graph depicting immunofluorescence result for EGFP (NELFA) and mCherry (H1) in NELFA-StrepHA-EGFP reporter mESCs stably expressing H1-mCherry transgene revealed loss of histone H1 from heterochromatin specifically in NELFA-positive cells. Quantification of the number of NELFA-positive cells and the localization of H1 was performed based on immunofluorescence data. Cells demarcated by white dotted boxes are shown in magnification, and the white arrows denote cells of interest. 2 independent experiments were performed. Scale bars=20 µm.
Figure 5C:
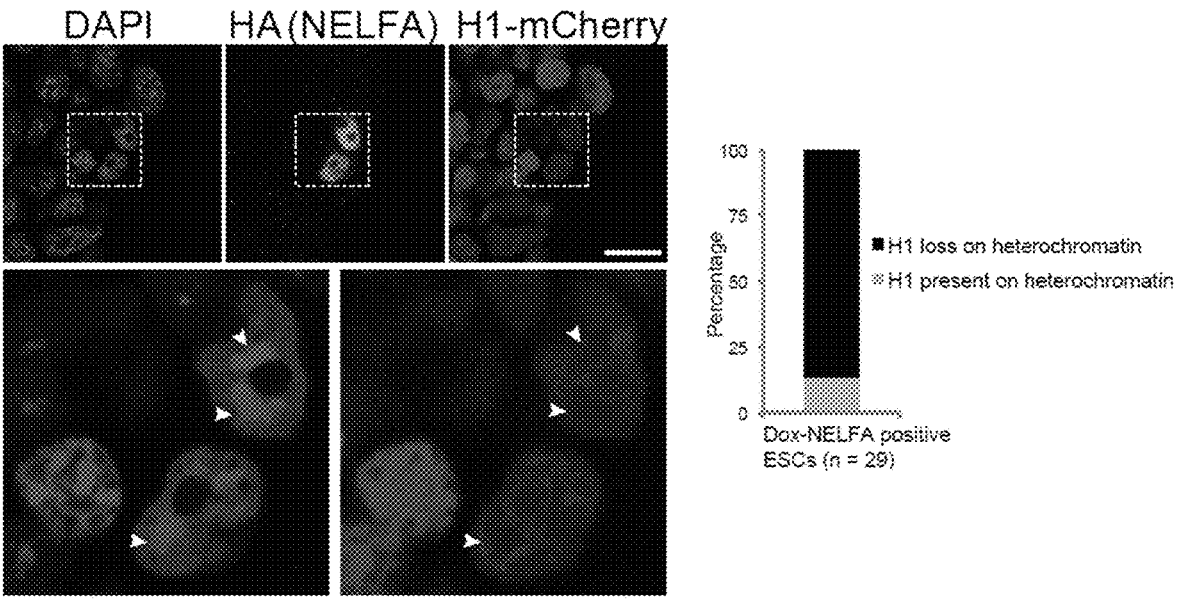
FIG. 5c is a set of microscopy images and a bar graph depicting immunofluorescence result for HA (NELFA) and mCherry (H1) in NELFA Dox-inducible mESCs stably expressing H1-mCherry transgene, following Dox induction for 16 hours. Quantification of the state of H1 heterochromatin occupancy in individual NELFA-positive cells was performed based on the immunofluorescence data. Cells demarcated by dotted boxes are shown in magnification, and the white arrows delineate DAPI-dense heterochromatic regions. 2 independent experiments were performed. Scale bar=20 µm.
Figure 5D:
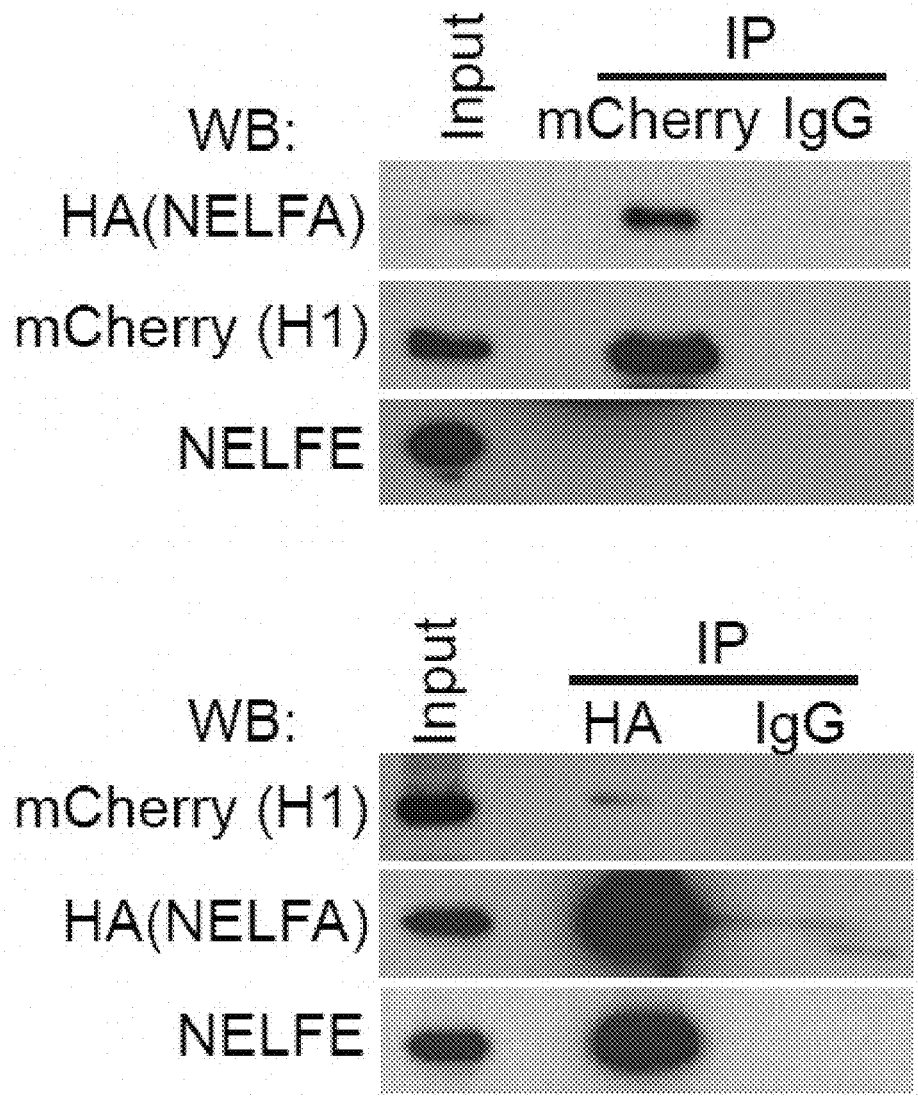
FIG. 5d is a set of Western Blot images depicting immunoprecipitation for H1-mCherry and NELFA-HA in 2-DG treated mESCs. The immunoprecipitates were subsequently probed with anti-HA (NELFA), anti-mCherry (H1), and anti-NELFE.
Figure 5E:
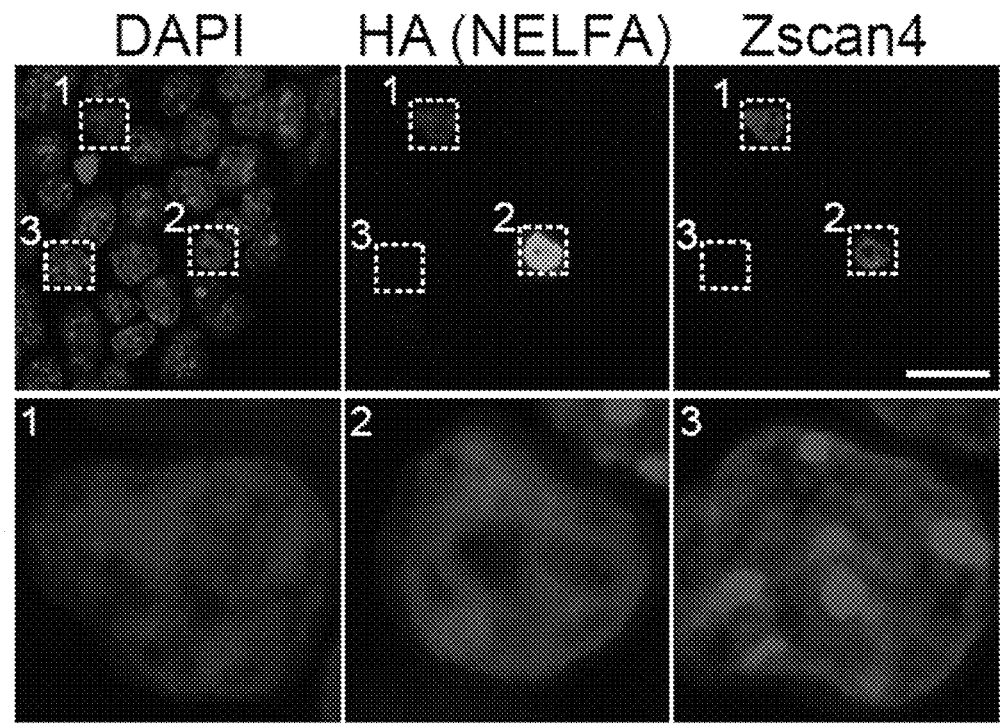
FIG. 5e is an image depicting immunofluorescence result for HA (NELFA) and Zscan4 in Dox-inducible NELFA-Strep-HA-P2A-EGFP mESCs, following Dox induction for 16 hours, revealed structural changes in heterochromatin. DAPI staining depicts the different extents of chromatin decondensation. Cells demarcated by white dotted boxes are shown in magnification. Scale bar=20 µm.
Figure 5F:
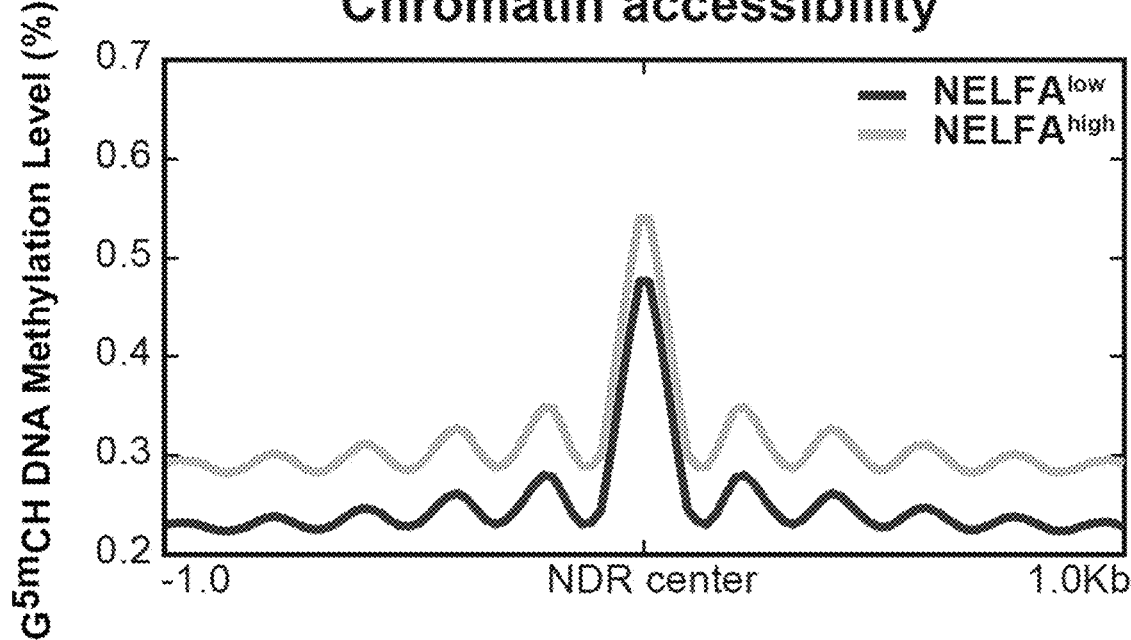
FIG. 5f is a line graph depicting chromatin accessibility patterns of NDRs and the flanking regions showing symmetrically well positioned nucleosomes in NELFA$^{high}$ and NELFA$^{low}$ cells. NDR: nucleosome depleted region. Y-axis denotes chromatin accessibility as the percentage of reads harboring methylated cytosines in the context of GCH (H, A/C/T).
Figure 5G:
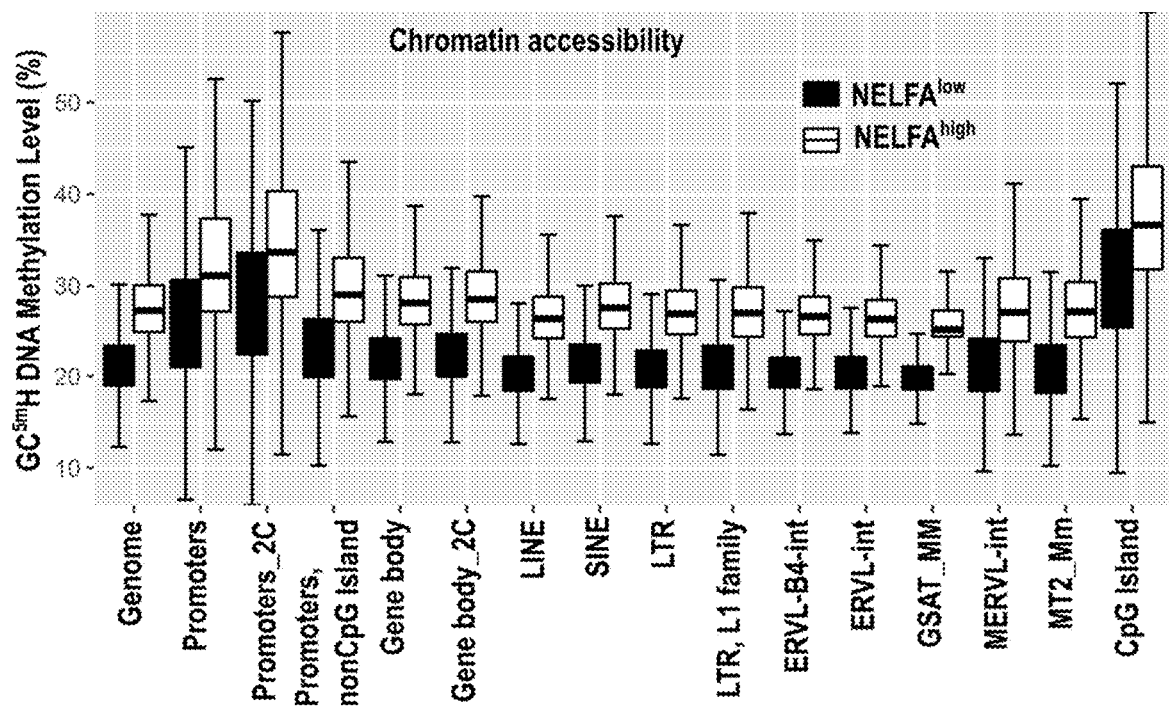
FIG. 5g is a boxplot showing chromatin accessibility of different genomic features (x-axis) in NELFA$^{high}$ versus NELFA$^{low}$ mESCs following 2-DG treatment. Y-axis denotes chromatin accessibility as the percentage of reads harboring methylated cytosines in the context of GCH (H, A/C/T). Center line: median; box limits: lower and upper quartiles; upper whisker: the smaller value of the maximum value and upper quantile plus 1.5× the interquartile range; lower whisker: the larger value of the minimum value and the lower quantile minus 1.5× the interquartile range.
Figure 5H:
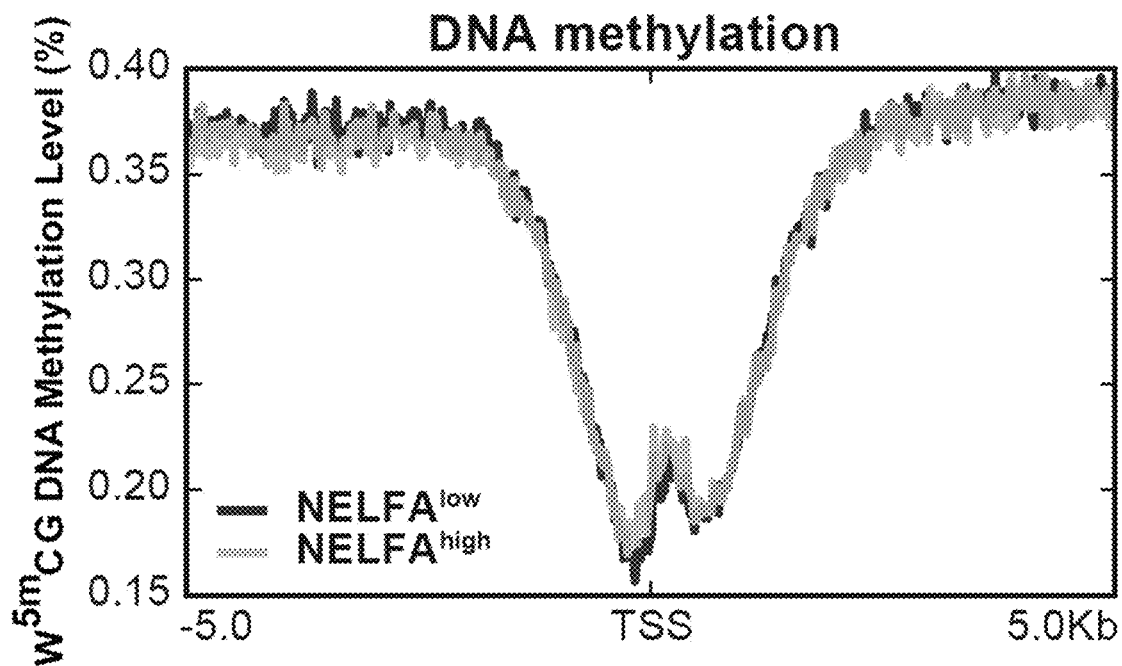
FIG. 5h is a line graph showing DNA methylation profile across TSSs of canonical transcripts in NELFA$^{high}$ versus NELFA$^{low}$ mESCs following 2-DG treatment. Y-axis denotes DNA methylation as the percentage of reads harboring methylated cytosines in the context of WCG (W, A/T).
Figure 5I:
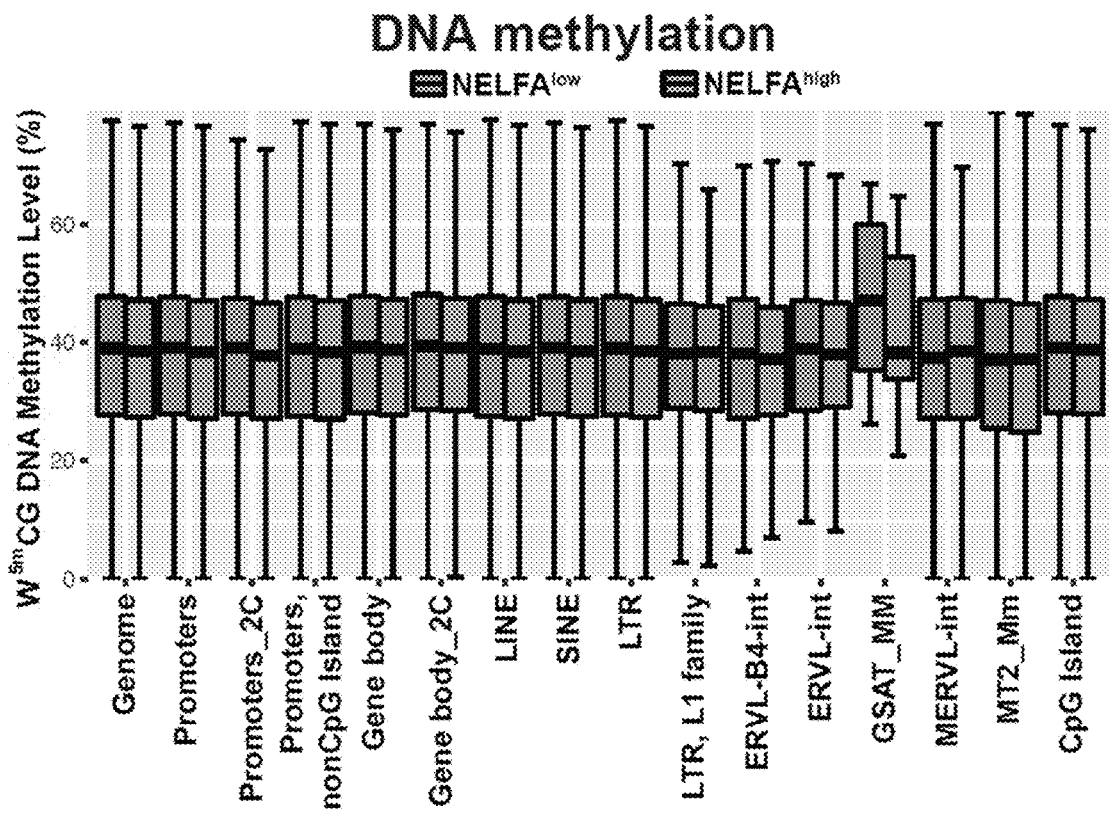
FIG. 5i is a boxplot depicting DNA methylation profiles of different genomic features in NELFA$^{high}$ versus NELFA$^{low}$ mESCs following 2-DG treatment. Y-axis denotes DNA methylation as the percentage of reads harboring methylated cytosines in the context of WCG (W, A/T). Genome: genome-wide WCG probes. Center line: median; box limits: lower and upper quartiles; upper whisker: the smaller value of the maximum value and upper quantile plus 1.5× the interquartile range; lower whisker: the larger value of the minimum value and the lower quantile minus 1.5× the interquartile range.

During the course of the investigations, it was noticed that in all cases where NELFA is upregulated (NELFA$^{high}$, Dox-induced and 2-DG-treated), the mESCs exhibited a markedly different heterochromatin structure compared to their NELFA$^{low}$ or non-induced counterparts. In particular, NELFA-upregulated mESCs either displayed a uniform loss of DAPI-dense chromocenters, or contained large diffuse 'clouds' of decondensed heterochromatin that clustered around the nucleolus (FIG. 5a and FIG. 5e). These observations suggest that the activation of NELFA may elicit global heterochromatin remodeling and chromatin decondensation that facilitate the subsequent upregulation of 2C transcriptional programs. To obtain a more quantitative measure of chromatin accessibility, Nucleosome Occupancy and Methylome sequencing (NOMe-seq), a method that simultaneously interrogates global changes in chromatin accessibility and DNA methylation, was performed on both 2-DG treated and control mESCs. Notably, increased chromatin accessibility across the genome in the NELFA$^{high}$ cells, including promoter regions as well as repetitive elements (FIG. 5f and FIG. 5g) was generally observed, consistent with the extensive heterochromatin remodeling that had been priorly observed by immunofluorescence (FIG. 5a). Overt changes in genome-wide DNA methylation was not detected, although some evidence of DNA demethylation can be observed on the major satellite repeats (gsat_mm) that are transcriptionally induced in 2C-like ESCs, suggesting that DNA demethylation may occur in a more protracted fashion (FIG. 5h and FIG. 5i). The NOMe-seq analysis thus further supports the model that chromatin decompaction is the primary mechanism utilized by NELFA-upregulated cells to prime mESCs for the downstream expression of 2C genes.

Figure 5J:
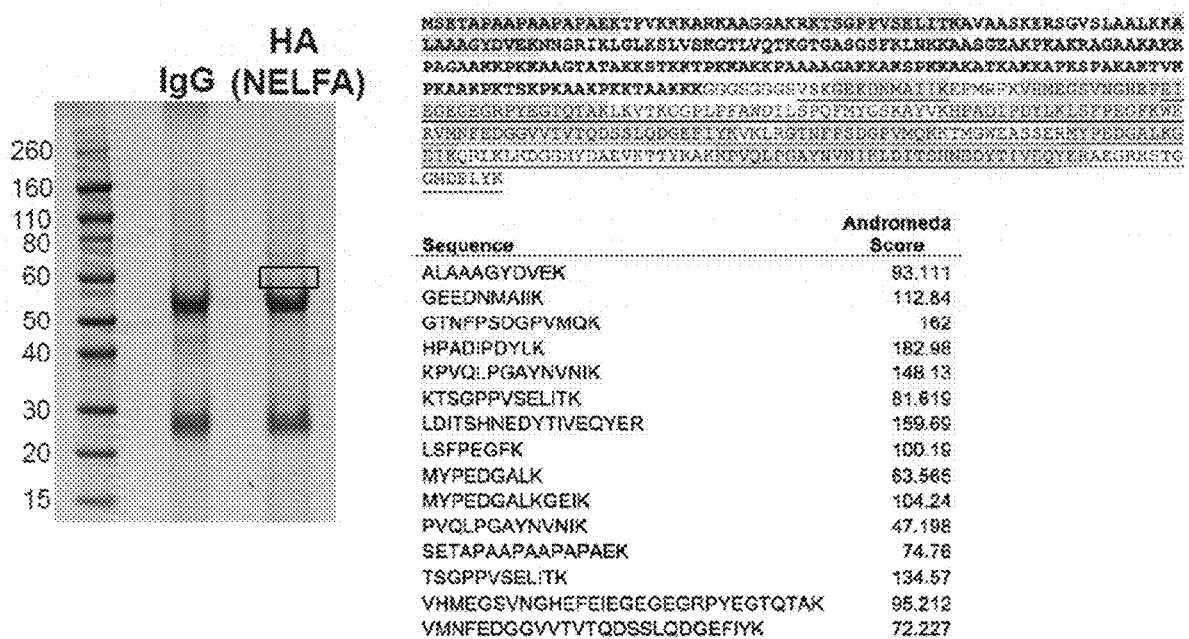
FIG. 5j is combination of a Western Blot image, a sequence, and a table depicting colloidal blue staining of SDS PAGE gel following immunoprecipitation for normal rabbit IgG control and NELFA (HA). Region excised for mass spectrometry is indicated by black box where the expected H1-mCherry fusion is (~55 kDa). The predominant bands observed represent the antibody heavy and light chain respectively (left panel). The amino acid sequences for H1-mCherry fusion protein are shown (right panel). H1 sequence is highlighted in bold and mCherry sequence is underlined. The detected peptides are highlighted and the respective scores presented. Thus.

In the pursuit to understand how NELFA may elicit global heterochromatin remodeling and chromatin decondensation, it was noted that the N-terminus of NELFA exhibits sequence similarity to the viral protein hepatitis delta antigen (HDAg); pertinently, a separate study showed that HDAg can interact with histone H1. Therefore, it was asked if NELFA might interact with H1 and facilitate its removal from chromatin, leading to the observed chromatin relaxation in NELFA-upregulated mESCs. First, a NELFA-EGFP reporter mESC line that stably expresses H1-mCherry fusion was generated. Following 2-DG treatment, a clear displacement of H1 from the heterochromatin in NELFA$^{high}$ mESCs was observed, in support of the hypothesis (FIG. 5b). Second, this analysis was repeated by similarly generating a H1-mCherry reporter in the Dox-inducible NELFA mESCs and equivalent results were critically obtained (FIG. 5c). The latter also confirms that H1 eviction is a direct consequence of NELFA upregulation. Third, to detect direct interactions between NELFA and H1, immunoprecipitation for H1-mCherry was performed, and a positive interaction with NELFA-HA was observed. Notably, no interaction was observed for NELFE, further supporting an independent role of NELFA in regulating 2C gene expression (FIG. 5d). Importantly, in the reciprocal NELFA-HA immunoprecipitation, an interaction with H1-mCherry was likewise detected, further affirming the direct interaction between NELFA and H1 (FIG. 5d). Mass spectrometry of NELFA-HA immunoprecipitate also detected numerous H1-mCherry peptides confirming a novel interaction between NELFA and H1 (FIG. 5j). Taken together, the data suggests a model in which NELFA's interaction with linker H1 histone leads to the latter's displacement from chromatin, and in doing so, induces chromatin decondensation that may contribute to the activation of 2C genes in NELFA-upregulated mESCs.

Example 8

Multiple Pathways Contribute to Chromatin Decondensation in NELFA-Upregulated mESCs The absence of chromocenters is widely regarded as a molecular feature of the totipotent zygotes, 2C embryos and 2C-like ESCs. However, it was also noted that the chromatin changes observed in NELFA-upregulated 2C-like cells bore a striking resemblance to the extensive heterochromatin reorganization that occurs during germline reprogramming. Primordial germ cells (PGCs) undergo epigenetic reprogramming typified by extensive chromatin remodeling such as the dissolution of chromocenters, differential localization of the histone chaperones CAF-1 and NAP1, as well as the loss of linker histone H1. Collectively, these events are thought to reset parental genomes in preparation for the acquisition of totipotency upon fertilization. Here, it was postulated if the epigenetic reprograming events occurring in PGCs may act in concert with NELFA to ensure robust chromatin remodeling for activation of the 2C program in mESCs.

Figure 6A:
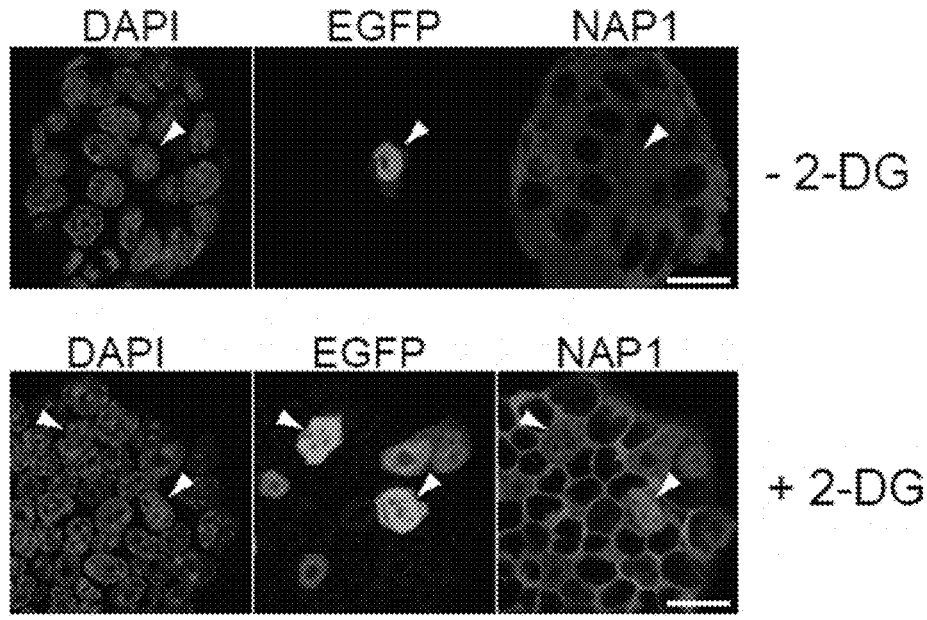
FIG. 6a is a set of microscopy images and bar graphs depicting immunofluorescence result for various markers—NELFA (marked by EGFP or HA) and NAP1—in NELFA reporter (top panel), NELFA reporter treated with 2-DG (middle panel) and Dox-inducible NELFA (bottom panel) mESCs showed predominantly nuclear NAP1 in the presence of NELFA. White arrows denote cells of interest. Quantification of the number of NELFA positive cells and their NAP1 cellular localization is indicated. 3 independent experiments were performed. Scale bar=20 µm.
Figure 6A:
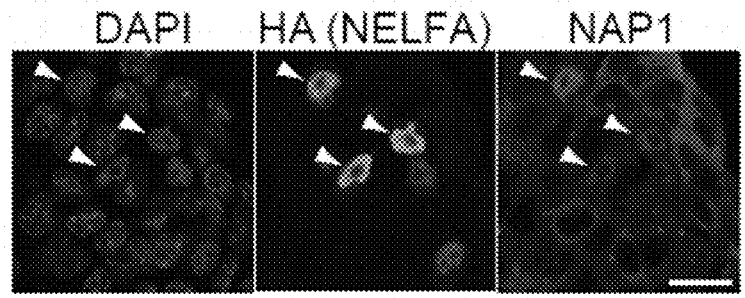
Figure 6A:
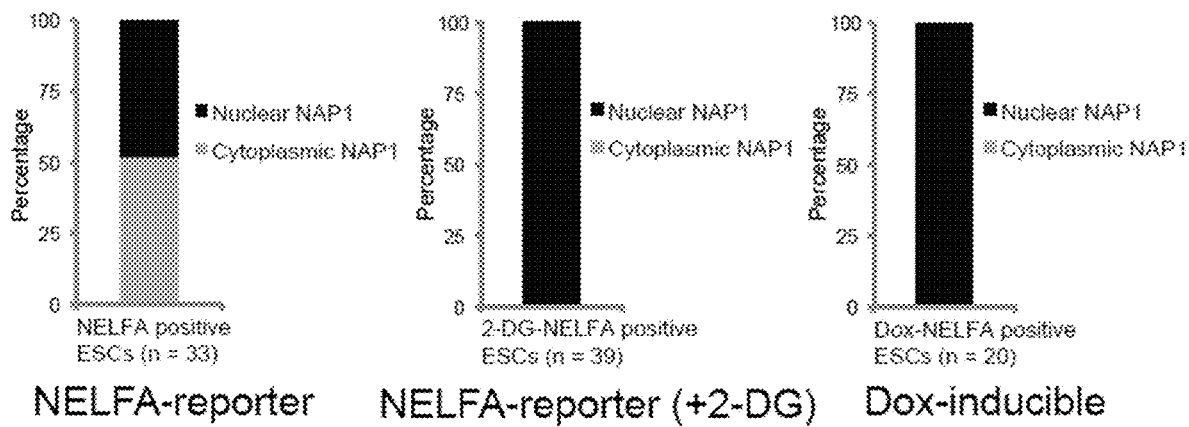
Figure 6B:
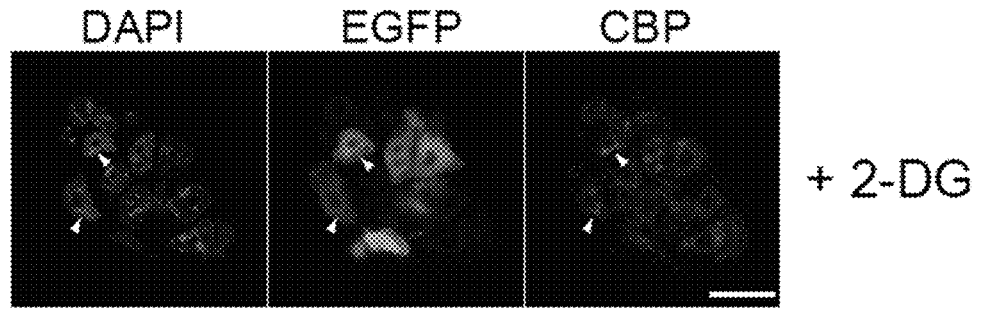
FIG. 6b is set of microscopy images and bar graphs depicting immunofluorescence result for NELFA (marked by EGFP or HA) and CBP in NELFA reporter treated with 2-DG (top panel) and Dox-inducible NELFA (bottom panel) mESCs revealed that CBP populates decondensing heterochromatin. Cells demarcated by dotted boxes are shown in magnification, and dashed lines delineate DAPI-dense heterochromatic regions. White arrows denote cells of interest. Quantification of the number of NELFA positive cells and their CBP localization is indicated. 2 independent experiments were performed. Scale bar=20 µm.
Figure 6B:
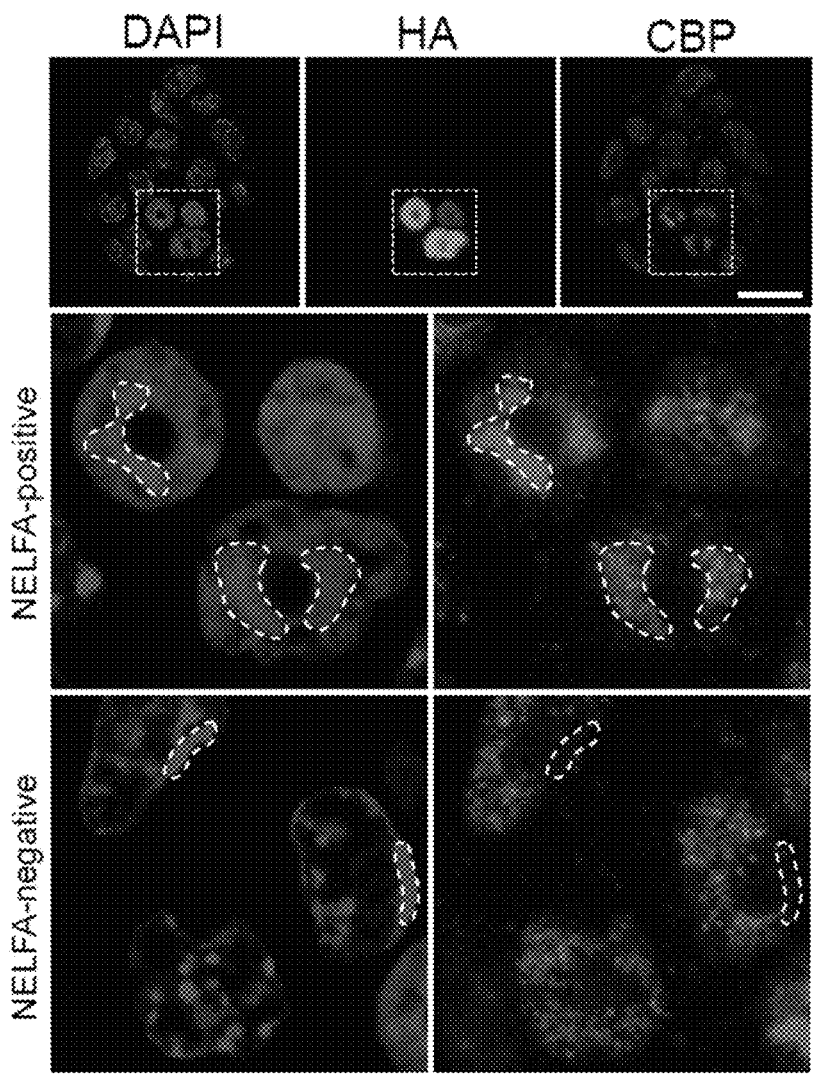
Figure 6B:
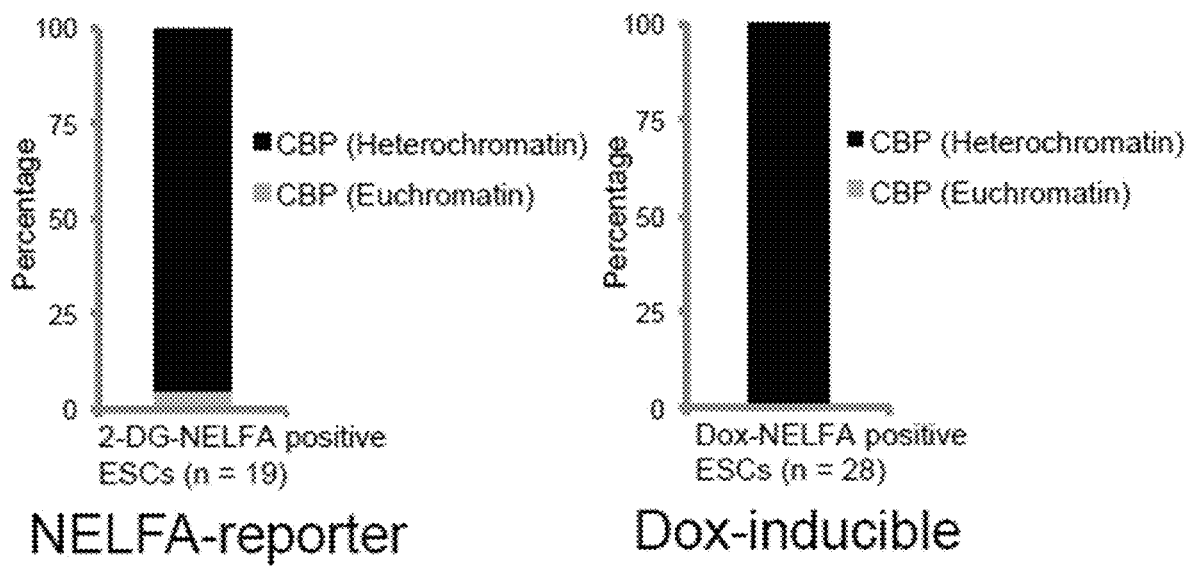
Figure 6C:
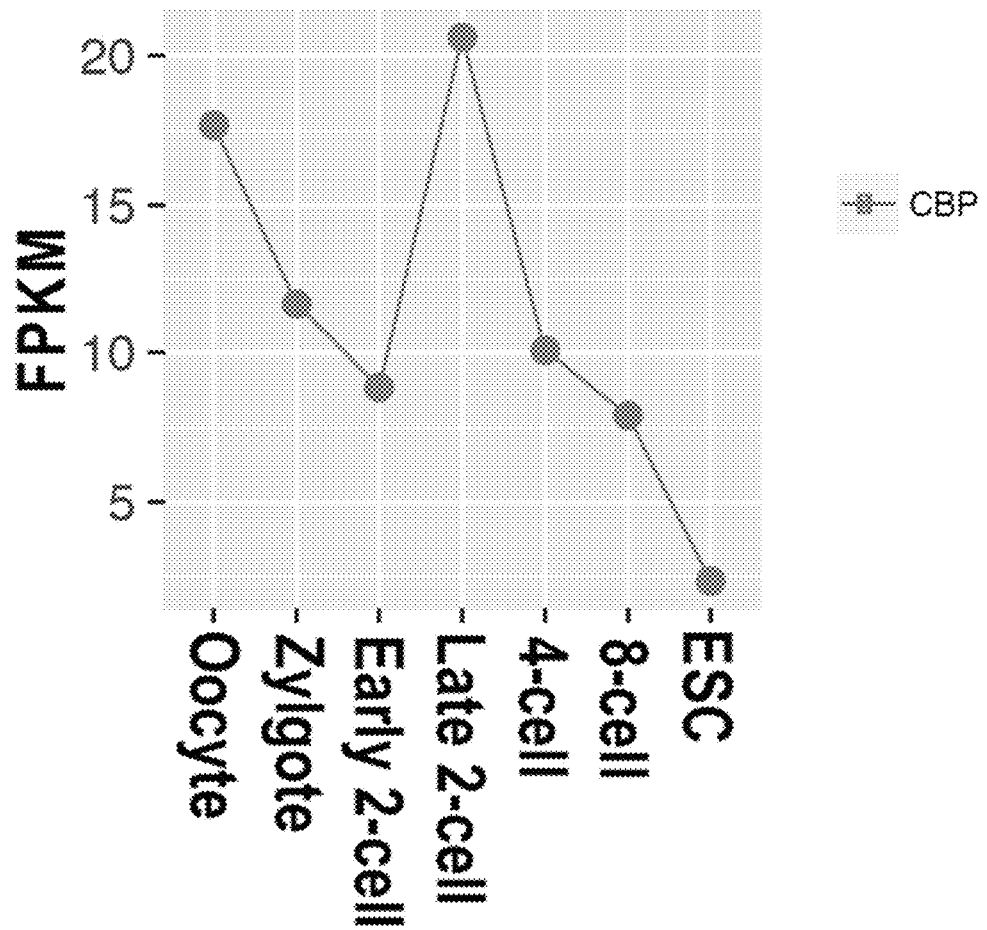
FIG. 6c is a line graph depicting relative expressions of CBP across different development stages in mouse preimplantation embryo. Thus.

In good agreement with the postulation, a distinct nuclear localization of NAP1 specifically in NELFA$^{high}$ reporter ESCs was observed, compared to predominantly cytoplasmic NAP1 as observed in the surrounding NELFA$^{low}$ mESCs in the immunostaining experiments (FIG. 6a). Strikingly, Dox-induced expression of NELFA also provoked nuclear translocation of NAP1 in almost all the cells analyzed (FIG. 6a). Considering the earlier observations, the data now suggests that chromatin decondensation through H1 eviction in NELFA$^{high}$ mESC is likely cooperatively mediated by both NELFA and NAP1 mechanisms. In addition to H1 displacements, the gain of histone acetylation is also critical and implicated in chromatin decompaction. In view of this, it was asked if the histone acetyltransferase CREB-binding protein (CBP), previously shown to be highly expressed in PGCs, oocytes and early cleavage stage embryos relative to ESCs (FIG. 6c), might be involved in NELFA-precipitated chromatin decompaction. Whilst CBP is normally excluded from heterochromatic chromocenters, immunofluorescence staining revealed that intriguingly, CBP is localized to decondensing heterochromatin 'clouds' specifically in NELFA-positive cells, indicating that it might be important for chromocenter dissipation in this context (FIG. 6b). These results indicate that multiple pathways are involved to ensure robust chromatin decompaction in NELFA-upregulated mESCs, and that chromatin decompaction is an important preceding step for the downstream activation of 2C program. Taken together, the findings revealed conceptual parallels between epigenetic reprogramming events in the germline and 2C-like cells, highlighting common principles underlying cellular reprogramming in general.

Example 9

Dissolution of Pluripotent State is Necessary for Entry into the Totipotent State Next to address if different ESC culture milieu may impact the emergence of Nelfa$^{high}$ totipotent-like ESCs, the cells were cultured in 'naïve' N2B27-serum free ESC conditions and an almost complete loss of Nelfa$^{high}$ subpopulation was observed, suggesting that naïve pluripotency antagonizes totipotency. In further support, the study sought to induce a pluripotent dormant state by the addition of Myc inhibitors (to mimic the 'diapaused' embryo in vivo), and obtained a similar finding. Notably, when Nanog is depleted, an increase in Nelfa$^{high}$ population was observed. Taken together, these findings suggest that dissolution of pluripotent state is necessary for entry into the totipotent state, and further raised the possibility that it may be possible to generate induced totipotent cells whilst bypassing pluripotency which is incompatible with the totipotent state.

Example 10

Figure 7A:
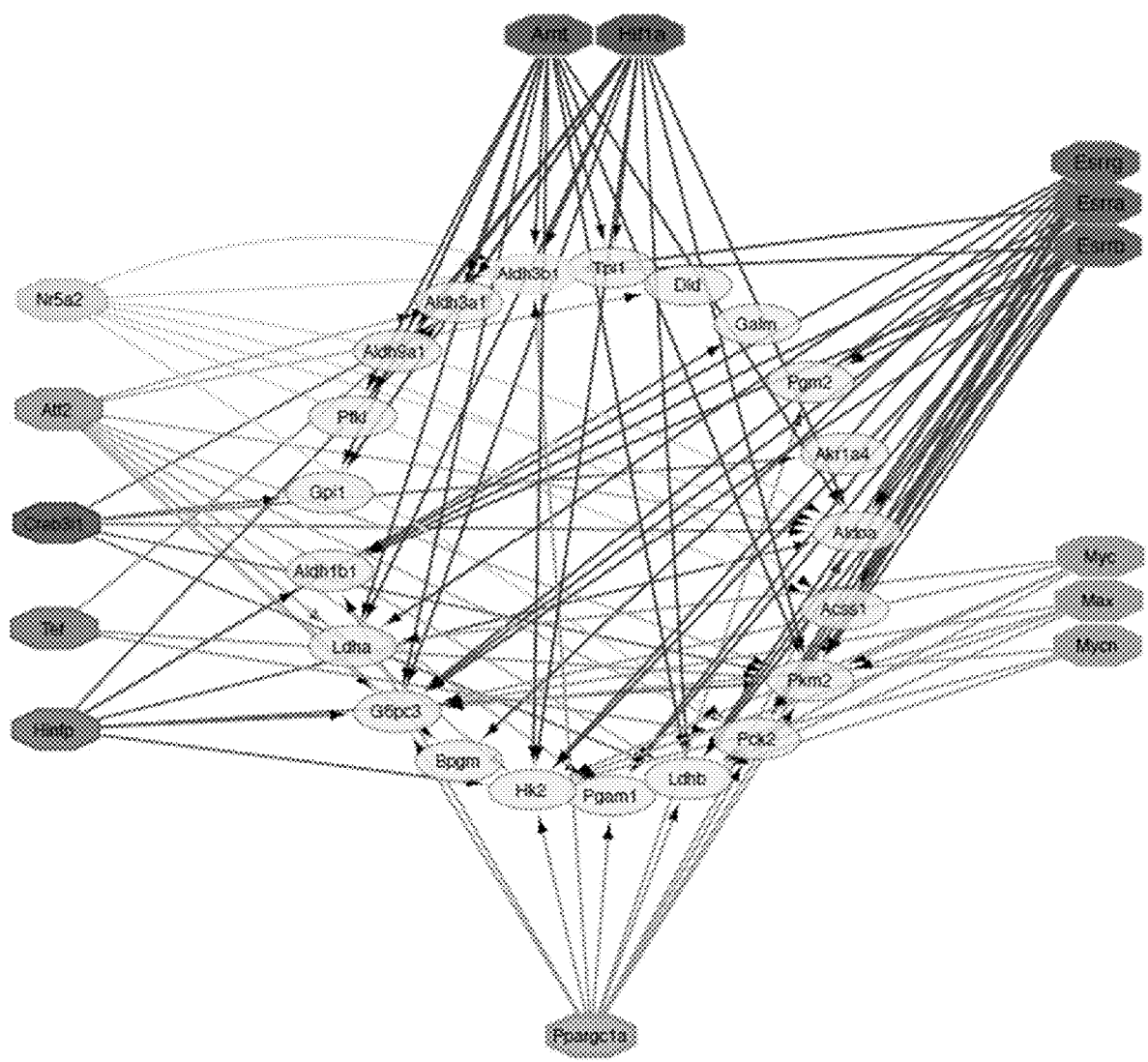
FIG. 7a is a diagram depicting an interaction landscape of potential glycolytic regulators that was identified by iRegulon. Various glycolytic regulators are arranged on the outermost edge. Putative direct target genes of the glycolytic regulators are denoted by the innermost circles.

Unveiling Novel Regulators of the 2C-Like State Through a Focused Interrogation of Glycolysis-Associated Genes The study has demonstrated a novel link between metabolism, particularly the suppression of glycolysis, and the acquisition of the 2C-like state. It was opined that the suppressed glycolytic state might represent a previously unappreciated feature of totipotency that can be manipulated to invoke the 2C-like state, as was shown earlier. Aiming to better understand this phenomenon, it is important to identify key regulators of glycolysis that might gate the entry of ESCs into the 2C-like state. In order to do so, the leading edge subset of 34 genes that accounted for the inhibited expression of glycolysis pathway as a whole in NELFA$^{high}$ mESCs from the GSEA analysis (see above) was first obtained and this gene list was subjected to iRegulon analysis, a computational method that identifies enriched motifs in the regulatory domains of input genes and direct target gene sets. This analysis recovered several well-known regulators of glycolysis, including proteins of the MYC family, HIF1a, and many others (FIG. 7a).

Figure 7B:
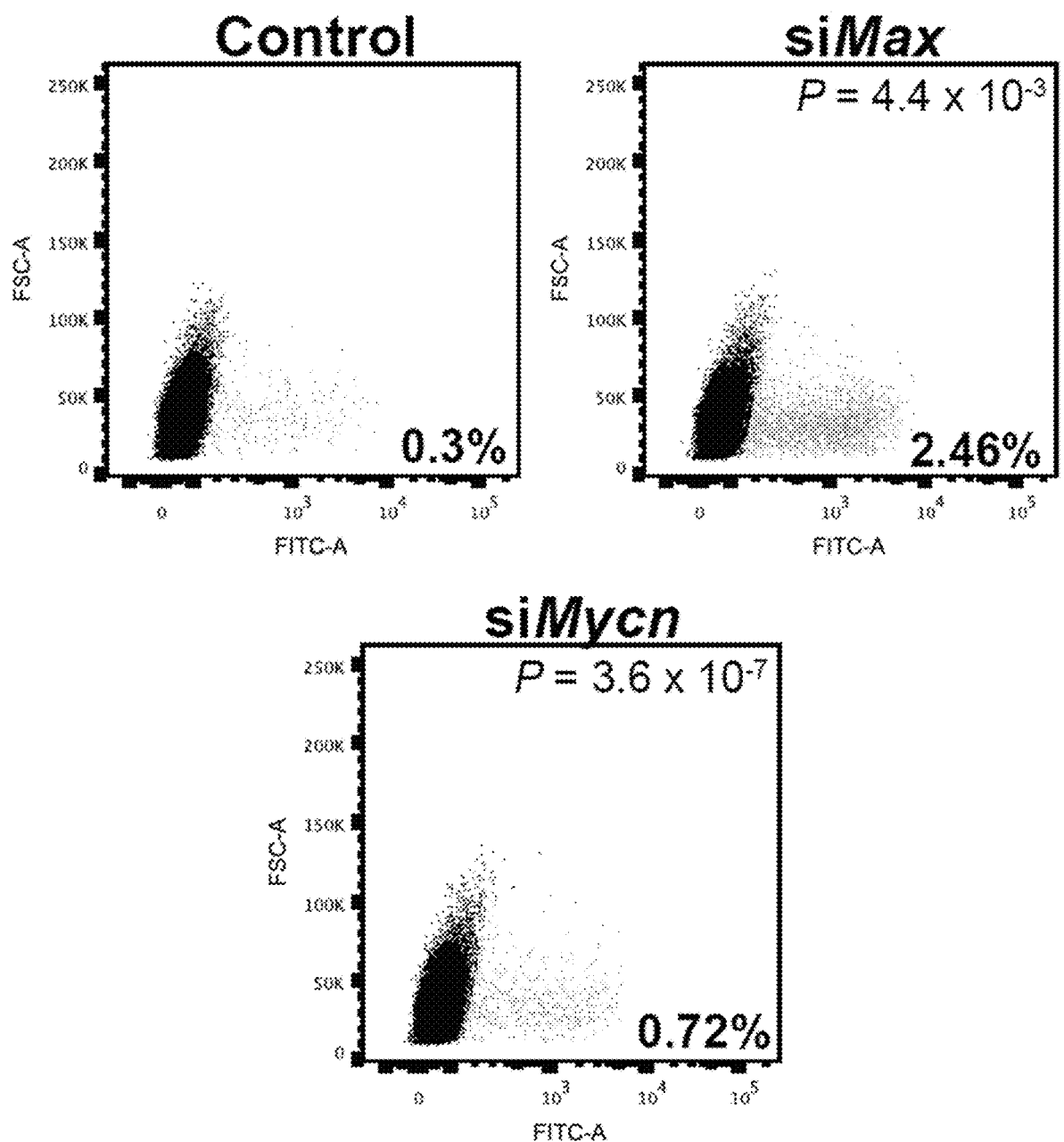
FIG. 7b is a set of plots depicting flow cytometry analysis of NELFA$^{high}$ mESCs after knockdown of various glycolytic regulators showed that abrogation of Max, N-Myc, and Esrrb gave the largest increases in the NELFA$^{high}$ population. Representative data from 5 independent experiments is shown here. P value determined by paired two-sided Student's T-test.
Figure 7B:
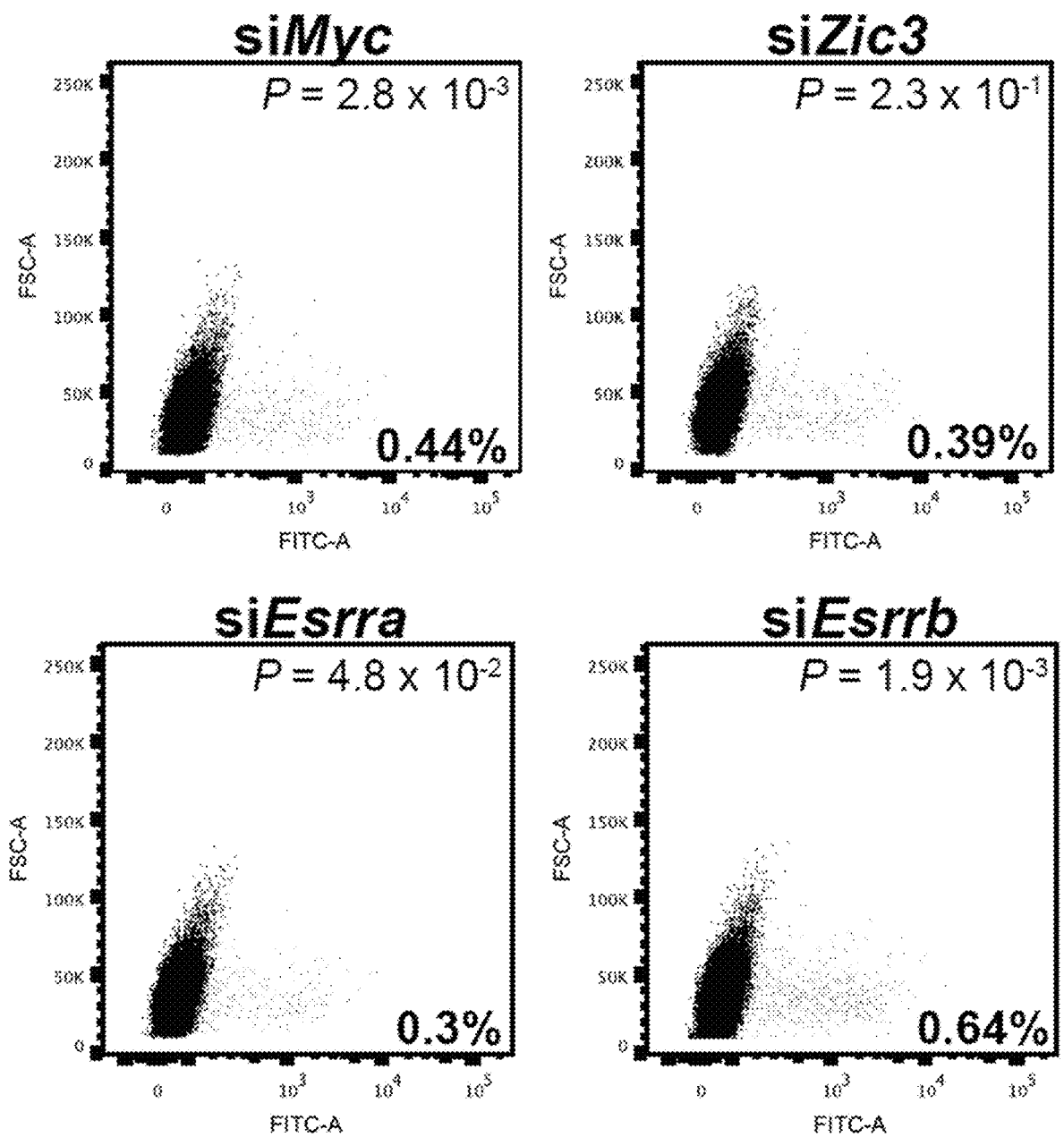
Figure 7B:
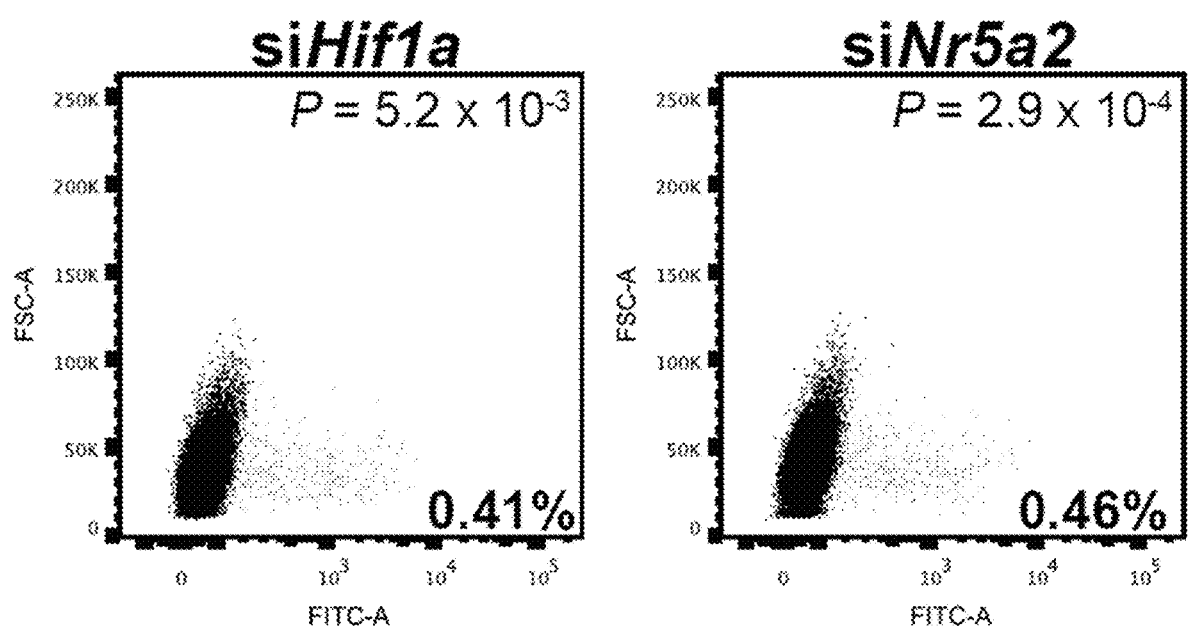
Figure 7C:
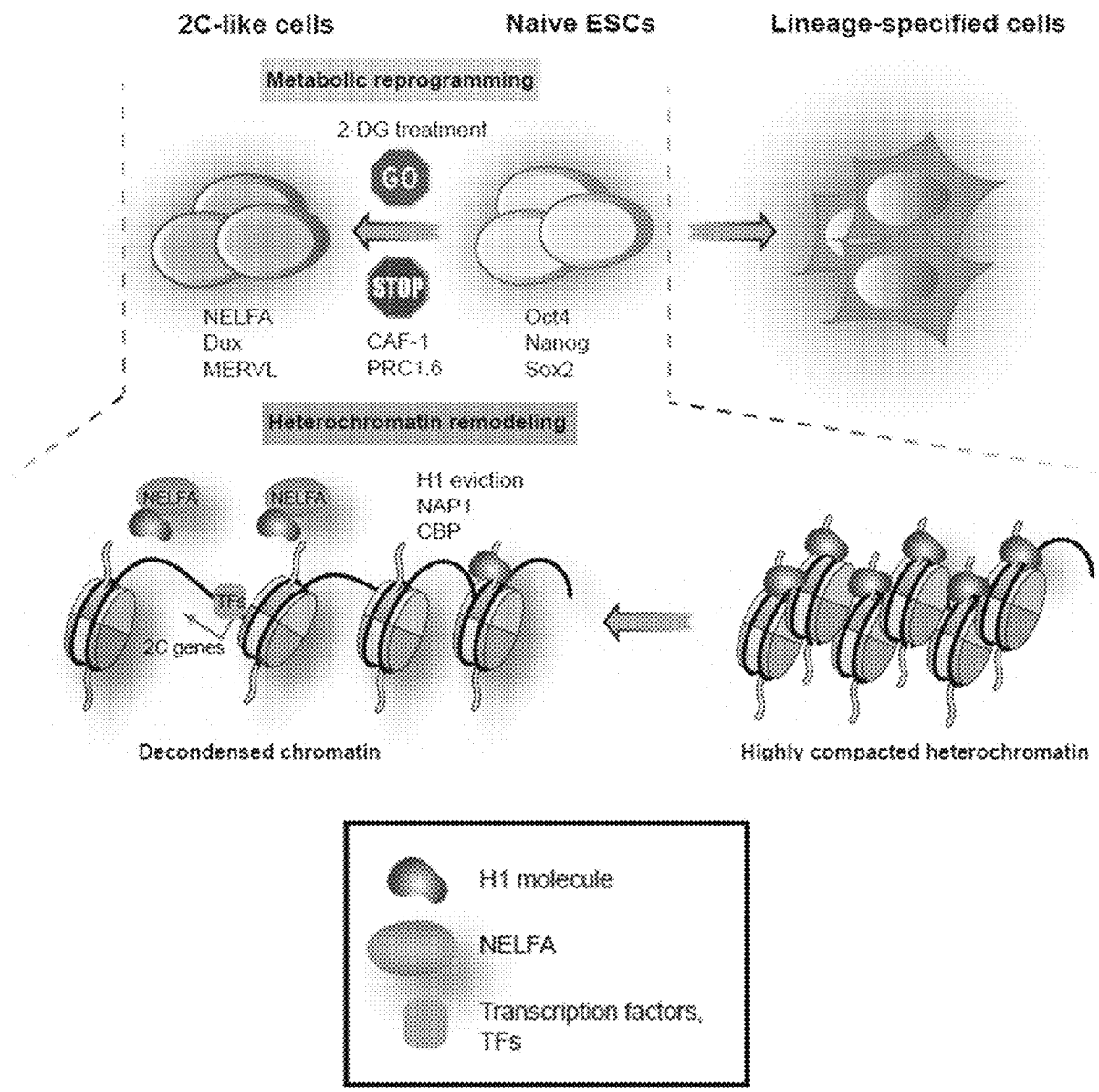
FIG. 7c is a diagram depicting working model of how NELFA induction can promote the ESC to 2C-like transition. The activation of 2C-stage gene expression in NELFA upregulated mESCs is characterized by both chromatin decompaction and metabolic reprogramming. NELFA contributes toward chromatin decompaction through robust H1 eviction along with the actions of NAP1 and CBP. This process generates a transcriptionally permissive chromatin that may allow access to a myriad of 2C-stage transcription factors to activate cleavage stage specific transcriptional program. It was further shown that the metabolic manipulation, particularly the suppression of glycolysis by small molecule supplementation (2-DG) or by knockdown of key glycolysis regulators, can evoke the emergence of 2C-like mESCs in a NELFA dependent manner and chromatin decompaction remains a central event.
Figure 7D:
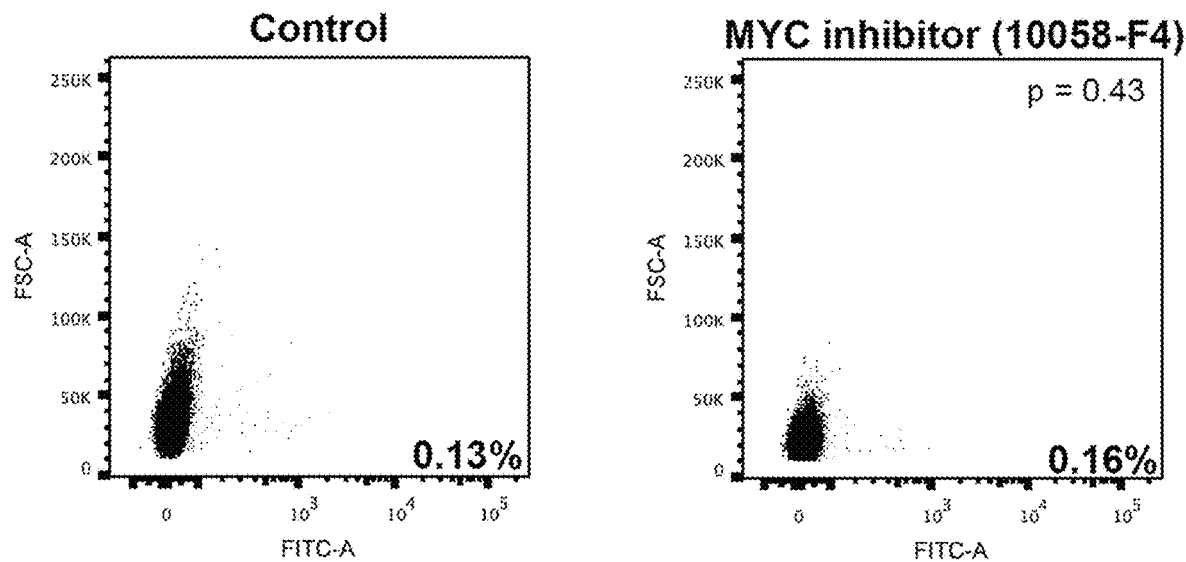
FIG. 7d is a pair of plots depicting result of flow cytometry analysis of NELFA-StrepHA-P2A-EGFP mESCs cultured in the presence of MYC inhibitor, 10058-F4. Representative data from 5 independent experiments is shown here. P value determined by paired two-sided Student's T-test.
Figure 7E:
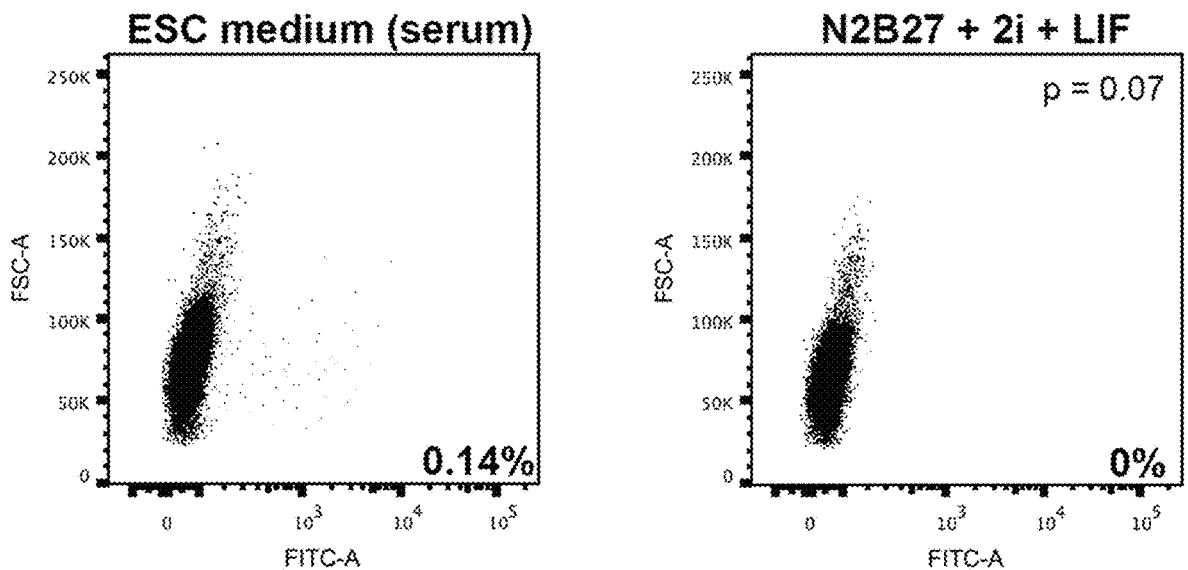
FIG. 7e is a pair of plots depicting result of flow cytometry analysis of NELFA-StrepHA-P2A-EGFP mESCs cultured in naïve, serum-free ESC condition (N2B27+2i+LIF). Representative data from 2 independent experiments is shown here. P value determined by paired two-sided Student's T-test. Representative phase contrast and EGFP fluorescence images are also shown.
Figure 7E:
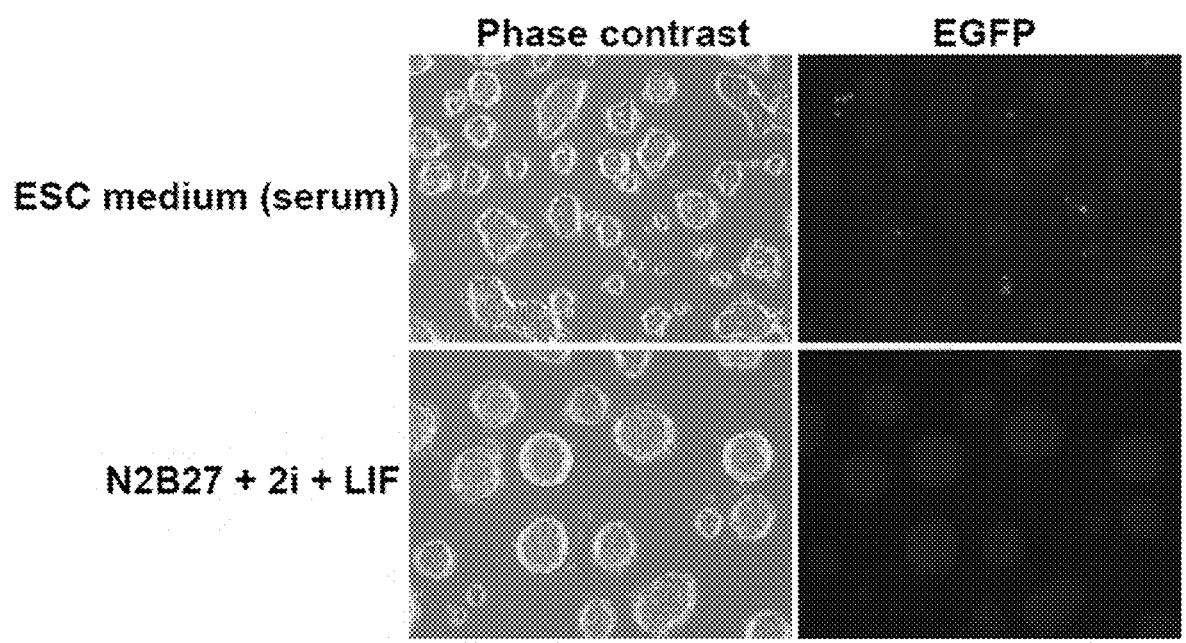

Selecting 8 candidate factors for further analysis, each of these glycolytic regulators was systematically knocked down, and then assayed for the changes in the population of NELFA$^{high}$ cells in the NELFA reporter mESCs. The results revealed that depletion of Max led to the greatest increase in the NELFA$^{high}$ population, followed by N-Myc and Esrrb knockdown (FIG. 7b). Peculiarly, c-Myc knockdown did not give any significant increase in NELFA$^{high}$ cells, raising the possibility that the effect seen in Max depletion may not have been mediated through the canonical MYC-MAX complex (FIG. 7b). To test this hypothesis, the NELFA reporter mESCs was treated with the pan-MYC inhibitor 10058-F4, which is known to affect MYC-MAX dimerization, and no increase in NELFA$^{high}$ population was observed (FIG. 7d). Two key insights can thus be derived from these findings. First, MAX is likely to operate independently of the canonical MYC-MAX complex to regulate the 2C gene expression program. Second, the pan-inhibition of Myc is known to induce a dormant pluripotent state in mESCs, akin to the diapaused epiblast in vivo, wherein pluripotency capacity is preserved against a backdrop of metabolic quiescence. ESCs in a dormant pluripotent state would block the acquisition of any alternative fates, including the 2C-like state. In agreement with this idea, a near-complete elimination of the NELFA$^{high}$ population was observed when cells were cultured under the ground state 'naïve' ESC condition (FIG. 7e). This reinforces the earlier hypothesis that regulated dissolution of the pluripotency network may be necessary for entry into the 2C-like state (FIG. 2e). In summary, this work has identified a maternally expressed factor NELFA as a novel driver of the 2C gene expression program. In the process, it was also uncovered for the first time the importance of metabolic regulation in controlling the transition between pluripotent and 2C-like states, and further demonstrated a surprisingly facile method of inducing a 2C-like state without the need for any genetic manipulation (FIG. 7c; model).

Discussion

Figure 7F:
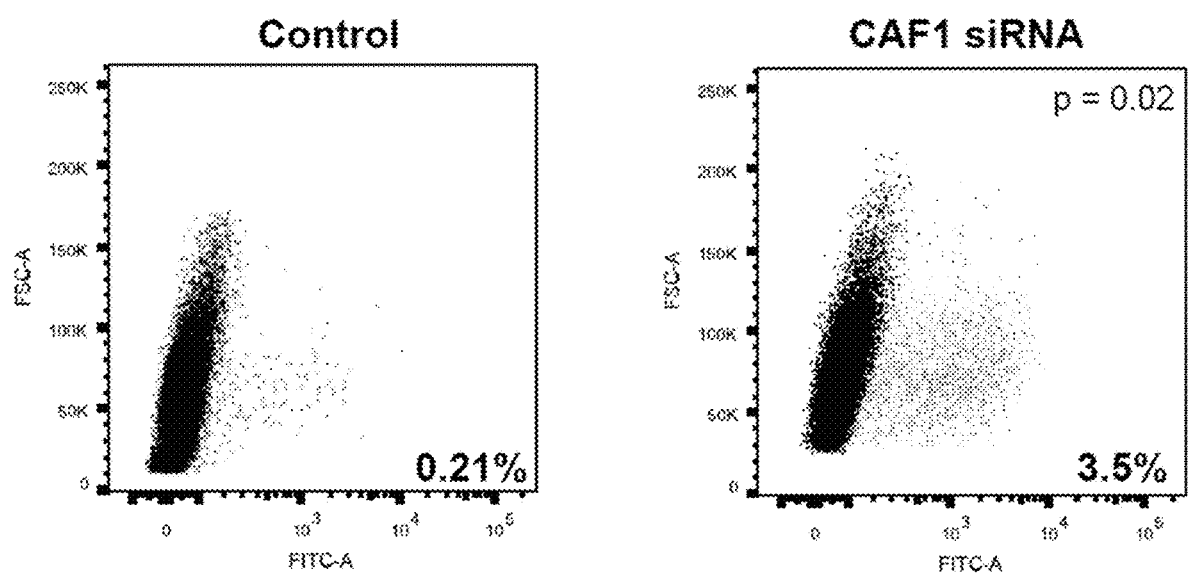
FIG. 7f is a pair of plots depicting result of flow cytometry analysis of NELFA-StrepHA-P2A-EGFP mESCs after knockdown of CAF1. Representative data from 3 independent experiments is shown here. P value determined by paired two-sided Student's T-test. Thus.

Mechanistically, it was shown that NELFA drives 2C program activation by creating a transcriptionally permissive chromatin though H1 displacement in both the Dox-induced and 2-DG treated NELFA$^{high}$ mESCs, which may facilitate the access of key transcription factors to activate 2C genes (Model; FIG. 7c). The work adds NELFA to the increasing panel of factors that is involved in H1 eviction. Additionally, the data suggests that the unusual nuclear localization of NAP1 and the enrichment of CBP on heterochromatin may cooperate with NELFA to ensure robust H1 eviction and chromatin decondensation for the activation of 2C program. Indeed, a two-step mechanism involving both histone acetylation and linker histone H1 eviction had been demonstrated to be critical for chromatin decompaction in vitro, in excellent agreement with the in vivo findings. Notably, the redistribution of CBP onto heterochromatin was also previously observed in Zscan4-Em positive cells. This study therefore highlights that chromatin decompaction may occur through multiple mechanisms that is key for the robust activation of 2C program in mESCs. Consistent with this idea, a recent study showed that the expression of the endogenous chromatin assembly factor, CAF-1, is mutually exclusive with 2C-like mESCs, and that depletion of CAF-1 could promote the emergence of 2C-like mESCs. Indeed, the loss of CAF-1 in the reporter mESCs gave rise to a robust increase in the NELFA$^{high}$ subpopulation (FIG. 7f). Furthermore, any overt loss of DNA methylation in our NOMe-Seq analysis in the NELFA$^{high}$ subpopulation was not detected. These results reinforce the notion that the modulation of chromatin structure is critical to regulating 2C genes. However, it is also plausible that a longer 2-DG treatment may be required in order to observe global loss of DNA methylation as DNA demethylation was previously reported to occur after chromatin decompaction, and is a late event in the pluripotent to 2C-like transition.

It is interesting to note that the nuclear organizational changes observed in NELFA-upregulated mESCs are strikingly similar to the epigenetic reprogramming events occurring in PGCs. However, the RNA-seq analysis of these cells did not detect significant upregulation of germ cell markers, arguing against their specification into the germ lineage. Rather, the data suggest that select epigenetic reprogramming mechanisms operating in the germ line may also be utilized in NELFA-upregulated cells to promote the pluripotent to 2C-like transition. Developing germ cells are indeed enroute to the formation of a totipotent zygote; in this view, the molecular changes occurring in PGCs are intimately tied to the acquisition of totipotency, and hence it might not be too unexpected that epigenetic mechanisms are shared between the different cell types transiting to a common state. An additional point of interest relates to CAF-1. Although CAF-1 is not downregulated in PGCs, it is specifically localized to the cytoplasm at the time of epigenetic reprogramming and should thus be inactive. The apparent lack of CAF-1 activity in PGCs and 2C-like mESCs further highlights that common chromatin-based mechanisms can be deployed in disparate contexts, the understanding of which may help to elucidate unifying principles of cellular plasticity.

Another important finding that emerged from the study was that NELFA-induced mESCs exhibited a suppressed metabolic state, a finding that dovetails neatly with decades-old embryological studies documenting that early cleavage-stage embryos as well as PGCs are metabolically less active, with lower oxygen and glucose consumption compared to blastocysts and ESCs. In particular, deliberate blockage of glycolysis is required for development of the totipotent embryo. Building on these pioneering studies, additional evidence that suppression of glycolysis governs the transition between pluripotency and early embryonic fate was provided. In this respect, the majority of studies to date on 2C gene regulation are largely centered on chromatin regulation, and multiple epigenetic repressors such as SETDB1, KAP1, G9A, LSD1, CAF-1, and PRC1 have been implicated as negatively correlated with the 2C-like state.

Encouraged by the finding that 2-DG-based suppression of glycolysis could activate the 2C gene program, it was found that Max knockdown elicited the greatest effect that is comparable to that of 2-DG treatment, whereas c-Myc depletion proved ineffectual. The results further corroborate two recent studies showing that the loss of Max can activate 2C genes. Whether NELFA-induced effects are mechanistically coupled to Max remains to be investigated. In summary, it was reported that NELFA is a novel driver of 2C-like mESCs and that the manipulation of the metabolic state by small molecule supplementation or by knockdown of key glycolysis regulators can instruct the reversion of ESCs into an earlier 2C-like state refreshingly provides a different dimension to 2C gene regulation, which may potentially be translated into novel cellular reprogramming strategies.

REFERENCES

1. Akiyama, T. et al. Transient bursts of Zscan4 expression are accompanied by the rapid derepression of heterochromatin in mouse embryonic stem cells. *DNA research: an international journal for rapid publication of reports on genes and genomes* 22, 307-318, doi:10.1093/dnares/dsv013 (2015).
2. Hendrickson, P. G. et al. Conserved roles of mouse DUX and human DUX4 in activating cleavage-stage genes and MERVL/HERVL retrotransposons. *Nature genetics* 49, 925-934, doi:10.1038/ng.3844 (2017).

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of isolating a totipotent-like embryonic stem cell (ESC) in a culture comprising:
   a) measuring the expression level of Negative Elongation Factor Complex Member A (Nelfa) in said ESC;
   b) correlating the expression level of Nelfa in said ESC with that of a reference sample,
   wherein an increased level of Nelfa expression in the ESC of at least 2-fold relative to that of the reference sample indicates that said ESC is a totipotent-like ESC; and
   c) isolating said totipotent-like ESC from said culture.

2. The method of claim 1 wherein the ESC is a mammalian ESC.

3. The method of claim 1, wherein the expression level of Nelfa is gene expression level, protein expression level or combinations thereof.

4. The method of claim 3, wherein the step of measuring the protein expression level of Nelfa is by immunohistochemistry or flow cytometry.

5. The method of claim 3, wherein the step of measuring the gene expression level of Nelfa comprises:
   a) contacting a nucleic acid sequence obtained or derived from said ESC with at least one primer and/or at least one probe for amplification of the Nelfa sequence;
   b) amplifying said nucleic acid sequence using said at least one primer and/or said at least one probe, and
   c) detecting the gene expression level of Nelfa.

6. The method of claim 5 wherein said amplification step is performed by polymerase chain reaction (PCR).

7. The method of claim 1, wherein the totipotent-like ESC is characterized by the Nelfa induced expression of Zinc Finger and SCAN Domain Containing 4 (Zscan4), 2-cell-stage, variable group, member 3 (Tcstv3), predicted gene 4340 (Gm4340), murine endogenous retrovirus-L/human endogenous retrovirus-L (MERVL/HERVL) family of retrotransposons, gamma-satellites mouse major repeat (gsat_mm), double homeobox (Dux) or combinations thereof in said ESC.

8. The method of claim 7, wherein the totipotent-like ESC is further characterized in that Nelfa acts upstream of Zscan4 and MERVL/HERVL family of retrotransposons in said ESC.

9. The method of claim 7, wherein the Nelfa induced expression of MERVL/HERVL family of retrotransposons comprises the retrotransposons solo long terminal repeat promotors of murine endogenous retrovirus-L (mt2_mm), murine endogenous retrovirus-L b4 internal regions (Mervl-b4-int), murine endogenous retrovirus-L_group-specific antigen (MERVL_gag) and murine endogenous retrovirus-L internal regions (Mervl-int).

10. The method of claim 1, wherein the totipotent-like ESC is further characterized by transient nuclear import of Nucleosome Assembly Protein 1 (NAP1) in said ESC.

11. The method of claim 1, wherein the totipotent-like ESC is further characterized by chromatin decondensation and expression of MERVL/HERVL family of retrotransposons and Zscan4 in said ESC.

12. A method of selecting totipotent-like embryonic stem cells (ESCs) from a population of embryonic stem cells in culture, comprising:
   (i)
   a) providing a population of ESCs that displays a predetermined phenotype when Nelfa is expressed;
   b) identifying the ESCs that express the predetermined phenotype; and
   c) selecting the ESCs that express the predetermined phenotype; or
   (ii)
   a) contacting said population of ESCs with an anti-Nelfa antigen binding protein;
   b) selecting the ESCs binding to said anti-Nelfa antigen binding protein; and
   c) optionally isolating the ESCs from said anti-Nelfa antigen binding protein.

13. The method of claim 12, wherein the predetermined phenotype is expression of a reporter gene; optionally wherein the reporter gene is green fluorescent protein (GFP).

14. The method of claim 12, wherein said cells are selected using single cell sorting, fluorescent activated cell sorting or magnetic cell sorting.

15. The method of claim 12, wherein the antigen binding protein is selected from the group consisting of a monoclonal antibody, a recombinant antibody, a polyclonal antibody, chimeric, a humanised antibody, a bispecific antibody, a heteroconjugate antibody, a single variable domain, a domain antibody, an antigen binding fragment, an immunologically effective fragment, a single chain Fv, a single chain antibody, a univalent antibody lacking a hinge region, a minibody, a diabody, and a tandem antibody.

16. A method of inducing totipotency in an embryonic stem cell (ESC) in culture, comprising contacting and incubating said ESC with one or more of a metabolic regulator, a small molecule compound, a chemical, a virus, a nucleic acid or a polypeptide, to induce expression of Nelfa.

17. The method of claim 16, wherein the metabolic regulator is selected from the group consisting of metabolites, metabolic intermediates, purines and pyrimidines, fatty acids, metabolic enzyme activators and inhibitors, glycolytic inhibitors, FDA approved drugs, dehydroepiandrosterone, L-buthionine sulfoximine, 3-bromopyruvate, 2-deoxy-D-glucose, dichloroacetate, GW9662, acetate, lactate, glucose, pyruvate, imatinib and amino acids; optionally wherein the metabolic regulator is selected from the group consisting of 2-deoxy-D-glucose, 3-bromopyruvate and imatinib.

18. The method of claim 16, wherein the nucleic acid is selected from the group consisting of microRNA, siRNA, RNA and cDNA.

19. The method of claim 2, wherein the mammalian ESC is a human ESC.

20. The method of claim 6, wherein said PCR is quantitative RT-PCR.

* * * * *

UNITED STATES PATENT AND TRADEMARK OFFICE
CERTIFICATE OF CORRECTION

| | |
|---|---|
| PATENT NO. | : 12,428,681 B2 |
| APPLICATION NO. | : 16/616523 |
| DATED | : September 30, 2025 |
| INVENTOR(S) | : Wee Wei Tee |

It is certified that error appears in the above-identified patent and that said Letters Patent is hereby corrected as shown below:

In the Claims

At Column 77, Line 49, "probe, and" should be -- probe; and --.

Signed and Sealed this
Tenth Day of February, 2026

John A. Squires
*Director of the United States Patent and Trademark Office*

```
                           SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: sgRNA sequence

<400> SEQUENCE: 1
gctgaccctc atcagaccag                                              20

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
cccttcctag tggtcgtgaa tgtcttt                                      27

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ctgctgtgaa gccattgtgg tgac                                         24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tttctcaagg cccaccaata gt                                           22

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5 gacaccttt ttaactatgc gagct                                         25

<210> SEQ ID NO 6
<211> LENGTH: 24
```

```
<212> TYPE: DNA
<213> ORGANISM: Artificial Sequence
<220> FEATURE:
<223> OTHER INFORMATION: Primer

<400> SEQUENCE: 6
gcccagagta caaggtgttc taat                                    24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
attcaatctt cggtaggatc tcag                                    24

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
accagctgaa acatccatcc                                         20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccatggatcc ctgaaggtaa                                         20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aacaggcgca gaggtaaaaa                                         20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcacagcctc cttacaccat                                         20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
```
cgaggcactg ggtctaagag                                           20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccaatgaaca ggtcatgctg                                           20

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tgctagtgga cacagtgttc ga                                        22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ttgaagcgtg tccactggcc                                           20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
agccatgtac gtagccatcc                                           20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gctgtggtgg tgaagctgta                                           20

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
agcgcactct ctttctctag gat                                       23

<210> SEQ ID NO 19
<211> LENGTH: 23
<212> TYPE: DNA
<213> ORGANISM: Artificial Sequence

```
<220> FEATURE:
<223> OTHER INFORMATION: Primer

<400> SEQUENCE: 19
ctgtggaagt gaagaggcag att                                              23

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ctggattcct tgtgcctcat                                                  20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aactccaatc ccaagtgctg                                                  20

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ggccctgcta tcaactttca aga                                              23

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gagcctctga tggacctctt tg                                               22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
aggaggaaaa ctgtctggca                                                  20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cctattctgg aaccagactc                                                  20
```

```
<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gggttcggat gtaagtcgag                                              20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccacagtggg gtagaggttg                                              20
```